(12) United States Patent
Dharmasiri et al.

(10) Patent No.: US 11,091,769 B2
(45) Date of Patent: Aug. 17, 2021

(54) DEVELOPMENT AND USE OF MODIFIED PLANTS AND SEEDS THAT ARE RESISTANT TO HERBICIDES AND ENVIRONMENTAL STRESS

(71) Applicant: Texas State University, San Marcos, TX (US)

(72) Inventors: Nihal Dharmasiri, San Marcos, TX (US); Sunethra Dharmasiri, San Marcos, TX (US); Praveen Kumar Kathare, Austin, TX (US)

(73) Assignee: TEXAS STATE UNIVERSITY, San Marcos, TX (US)

( * ) Notice: Subject to any disclaimer, the term of this patent is extended or adjusted under 35 U.S.C. 154(b) by 88 days.

(21) Appl. No.: 16/196,973

(22) Filed: Nov. 20, 2018

(65) Prior Publication Data
US 2019/0153466 A1    May 23, 2019

Related U.S. Application Data

(60) Provisional application No. 62/589,315, filed on Nov. 21, 2017.

(51) Int. Cl.
*A01H 1/00* (2006.01)
*C12N 15/82* (2006.01)
*A01H 1/04* (2006.01)

(52) U.S. Cl.
CPC ......... *C12N 15/8274* (2013.01); *A01H 1/045* (2021.01); *A01H 1/123* (2021.01); *A01H 1/1225* (2021.01); *C12N 15/8279* (2013.01)

(58) Field of Classification Search
None
See application file for complete search history.

(56) References Cited

U.S. PATENT DOCUMENTS 7,569,389 B2  8/2009  Feldmann et al.
7,820,883 B2  10/2010  Walsh et al.
8,603,755 B2  12/2013  Walsh et al.
(Continued)

OTHER PUBLICATIONS

Minter. Characterization of AFB5 in *Arabidopsis* auxin signaling. Thesis submitted to Texas State University. 2015. pp. 1-71.*
(Continued)

*Primary Examiner* — Ashley K Buran
(74) *Attorney, Agent, or Firm* — Winstead PC

(57) ABSTRACT

Embodiments of the present disclosure pertain to modified plants or seeds that contain a mutated gene. The mutated gene includes, without limitation, a pic30 mutant, a mutant homolog of pic30, and combinations thereof. The modified plant or seed is resistant to at least one herbicide, such as picloram. The modified plant or seed may also be resistant to one or more sources of environmental stress, such as drought, plant pathogenesis, biotic stress, and abiotic stress. Additional embodiments of the present disclosure pertain to methods of controlling the growth of weeds in a field by applying at least one herbicide to the field that includes the aforementioned modified plants or seeds. Additional embodiments of the present disclosure pertain to methods of developing the aforementioned modified plants or seeds by introducing one or more of the aforementioned mutated genes to a plant or seed.

Figure 1A:
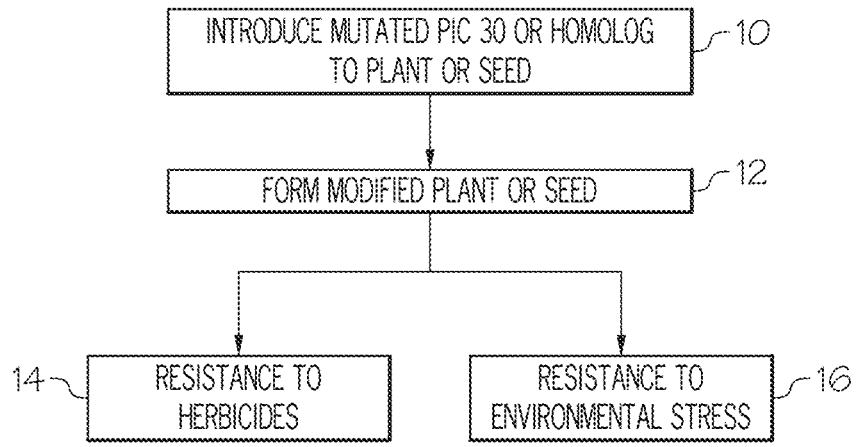

20 Claims, 41 Drawing Sheets
Specification includes a Sequence Listing.

(56) References Cited

U.S. PATENT DOCUMENTS

2014/0208463 A1* 7/2014 Deall .................... A01N 47/06
800/298

OTHER PUBLICATIONS

Miller et al. Cross-resistance in and chemical control of auxinic herbicide-resistant yellow starthistle (*Centaurea solstitialis*) 1. Weed Technology. 2001. 15: 293-299.*
Kathare et al. *Arabidopsis* PIC30 encodes a major facilitator superfamily transporter responsible for the uptake of picolinate herbicides. The Plant Journal. 2020. 102:18-33.*
Dharmasiri et al. Characterization of the *Arabidopsis* mtuant PIC30, that is specifically resistant to auxinic herbicide picloram. 19th Internation Conference on *Arabidopsis* Research. 2008. excerpt pp. 1 and 116. Full copy available https://www.arabidopsis.org/news/19th_ICAR_AbstractBook_2008.pdf.*
Friedberg et al. Automated protein function prediction—the genomic challenge. Briefings in Bioinformatics. 2006. 7(3):225-242.*
"Synthetic Auxin Resistance Fact Sheet Jun. 2016," *Herbicide Resistance Action Committee,* downloaded from <https://hracglobal.com/files/Synthetic-Auxin-Fact-Sheet-June-2016.pdf>.
Chrisoffoleti et al., "Auxinic herbicides, mechanisms of action, and weed resistance: A look into recent plant science advances," Sci. Agric. v.72, n.4, p. 356-362, Jul./Aug. 2015.
Green et al., "Herbicide-Resistant Crops: Utilities and Limitations for Herbicide-Resistant Weed Management," J. Agric. Food Chem. 2011, 59, 5819-5829.
John F. Egan et al., 2,4-Dichlorophenoxyacetic acid (2,4-D)-resistant crops and the potential for evolution of 2,4-D-resistant weeds, PNAS Mar. 15, 2011 108 (11) E37.
Terry R. Wright et al., Robust crop resistance to broadleaf and grass herbicides provided by aryloxyalkanoate dioxygenase transgenes, PNAS Nov. 23, 2010 107 (47) 20240-20245.
Kai Xun Chan et al., Sensing and signaling of oxidative stress in chloroplasts by inactivation of the SAL1 phosphoadenosine phosphatase. Proceedings of the National Academy of Sciences, 2016; 201604936 DOI: 10.1073/pnas.1604936113 <http://dx.doi.org/10.1073/pnas.1604936113>.
Preston et al., Inheritance of Resistance to the Auxinic Herbicide Dicamba in Kochia (Kochia scoparia), Weed Science <http://www.bioone.org/loi/wees> Jan. 2009 : vol. 57, Issue 1, pp. 43-47.
Emily Waltz, Beating the Heat, Nature Biotechnology, 32, 610-613, 2014.
Büttner M (2007) The monosaccharide transporter(-like) gene family in *Arabidopsis*. FEBS Lett 581: 2318-2324.
Dharmasiri N., Dharmasiri S., Jones A.M., and Estelle M. 2003. "Auxin action in a cell-free system" Current Biology, 13:1418-1422.
Dharmasiri N., Dharmasiri S. and Estelle M. (2005) The F-box protein TIR1 is an auxin receptor. Nature 435: 441-445.

Haydon MJ, Cobbett CS (2007) A novel major facilitator superfamily protein at the tonoplast influences zinc tolerance and accumulation in *Arabidopsis*. Plant Physiol 143: 1705-1719.
Kanno Y, Hanada A, Chiba Y, Ichikawa T, Nakazawa M, Matsui M, Koshiba T, Kamiya Y, Seo M (2012) Identification of an abscisic acid transporter by functional screening using the receptor complex as a sensor. Proc Natl Acad Sci U S A 109: 9653-9658.
Krouk G, Crawford NM, Coruzzi GM, Tsay YF (2010) Nitrate signaling: adaptation to fluctuating environments. Curr Opin Plant Biol 13: 266-273.
Peng H, Han S, Luo M, Gao J, Liu X, Zhao M (2011) Roles of multidrug transporters of MFS in plant stress responses. International journal of bioscience, biochemistry and bioinformatics 1: 109-113.
Reinders A, Panshyshyn JA, Ward JM (2005) Analysis of transport activity of *Arabidopsis* sugar alcohol permease homolog AtPLT5. J Biol Chem 280: 1594-1602.
Remy E, Cabrito TR, Baster P, Batista RA, Teixeira MC, Friml J, Sá-Correia I, Duque P (2013) A major facilitator superfamily transporter plays a dual role in polar auxin transport and drought stress tolerance in *Arabidopsis*. Plant Cell 25: 901-926.
Wang YY, Tsay YF (2011) Arabidopsis nitrate transporter NRT1.9 is important in phloem nitrate transport. Plant Cell 23: 1945-1957.
Grossmann K., Kwiatkowski J. & Tresch S. (2001) Auxin herbicides induce H2O2 overproduction and tissue damage in cleavers (*Galium aparine* L.). Journal of Experimental Botany 52, 1811-1816.
Hagen G. & Guilfoyle T. (2002) Auxin-responsive gene expression: genes, promoters and regulatory factors. Plant Molecular Biology 49, 373-385.
Haydon M.J. & Cobbett C.S. (2007) A novel major facilitator superfamily protein at the tonoplast influences zinc tolerance and accumulation in *Arabidopsis*. Plant Physiology 143, 1705-1719.
Ito H. & Gray W.M. (2006) A gain-of-function mutation in the *Arabidopsis* pleiotropic drug resistance transporter PDR9 confers resistance to auxinic herbicides. Plant Physiology 142, 63-74.
Kanno Y., Hanada A., Chiba Y., Ichikawa T., Nakazawa M., Matsui M., Seo M. (2012) Identification of an abscisic acid transporter by functional screening using the receptor complex as a sensor. Proceedings of the National Academy of Sciences, USA 109, 9653-9658.
Mithila J., Hall J.C., Johnson W.G., Kelley K.B. & Riechers D.E. (2011) Evolution of resistance to auxinic herbicides: Historical perspectives, mechanisms of resistance, and implications for broadleaf weed management in agronomic crops. Weed Science 59, 445-457.
Parry G., Ward S., Cernac A., Dharmasiri S. & Estelle M. (2006) The *Arabidopsis* Suppressor of Auxin Resistance proteins are nucleoporins with an important role in hormone signaling and development. The Plant Cell 18, 1590-15603.
Walsh T.A., Neal R., Merlo A.O., Honma M., Hicks G.R., Wolff K., Davies J.P. (2006) Mutations in an auxin receptor homolog AFB5 and in SGT1b confer resistance to synthetic picolinate auxins and not to 2,4-dichlorophenoxyacetic acid or indole-3-acetic acid in *Arabidopsis*. Plant Physiology 142, 542-552.

* cited by examiner

|      |            |            |            |            |            |            |
|------|------------|------------|------------|------------|------------|------------|
| 1    | ATGGTGGCTG | CAAGTCCCGG | TGGCTCAATG | AAGAGTTAA  | CCATCCAAAT | AGATGGTTCA |
| 71   | TGTTCTTTGG | AAGTCTCTTA | ATCATGTCGA | CAGCTGGAGC | CACTTACATG | ACTCAGGCGA |
| 141  | TATCAAGGAA | ACCTTAGGCT | ACGACCAAAC | CACTCTTAAT | CTCCTAAGT  | TCTCGGAGCC |
| 211  | AACGTTGGAG | TCCTCGCGGG | TCTACTCAAT | GAGGTAACTC | CTCCTTGGTT | ATCGGAGCCA |
| 281  | TCCTTAACTT | CTTTGGATAC | TTCATGATTT | GGCTCGCCGT | CACGAACCGG | CTCAAGTTTG |
| 351  | GCACATGTGT | CTCTATATCT | GCGTTGGAGC | CAACTCGCAG | TCGTTCGCTA | TCTCGTCACG | pic30-1
| 421  | TGCGTTAAGA | ACTTCCCGGA | GTCAGGTGGG | GTTGTCTTGG | GGATTCTCAA | GGTCTTAGTG |
| 491  | GCGCCATTAT | TACACAGTC  | TACCGTGCCT | TTATGGTGA  | AGACACAAAA | GAGCTCATCT | TGATGATTGg |
| 561  | taagcacaat | ttctaaaatt | attcatgaga | ctatatggtt | aatgcatga  | acagagtaaa |
| 631  | aacagagcaa | aacagagtaa | atcttggata | gaaacacata | ctaattgtat | gagtgattgt | pic30-3
| 701  | TGGTTGCCGG | CTATAGTCTC | GTTTGGGTTT | TTGAGAACGA | TAAGAATAAT | GAAAGTGAAA | AGACAGACAA |
| 771  | ACGAACTAAA | GGTGTTCTAT | AACTTCCTCT | ACATATGGCT | CGGGCTTGCG | ACGTTCTCA  | TGGTGGTCAT |
| 841  | CATCATCAAC | AAACTCTCGG | GCTTACACA  | AAGCGAGTTT | GGAGGTAGCG | CCGCGGTAGT | GATCGTCTTA |
| 911  | CTTCTTTGC  | CCATTATAGT | CGTCATCTTG | CGTCATCTTG | GGAGAAACAA | GGAGGTAGCG | GTGCCTTAA  |
| 981  | ACGATCCAGC | ACCCATCAAT | GTCGTAACTG | GTTAGATTCA | TCAGAGTTCA | AAGATGATGA |
| 1051 | TGGTGAAGAG | TCAAGGAGG  | TAGTGGAGAA | GGTGAAAACA | CCGTCCGTGT | GGACGACTGT | GTTAATCCA  |
| 1121 | CCGGAGAGAG | GAGATGACTA | TACAATCTTG | CAAGCGGTGT | TTAGGTAGA  | CATGTGATT  | TTGTCTTAG  |
| 1191 | CAACGATATG | TGGGTAGGA  | GGGACTTTGA | CGGCGATAGA | CAATTGGGT  | CAAATGGAA  | ACTCGTTGGG |
| 1261 | TTACCCGAAG | AGAGGGTAA  | GCACGTTTGT | GTCACTCGTA | AGCATATGGA | ATTACTATGG | TGTGTGGTT  |
| 1331 | TCAGTGTGG  | TCTCTGAGAT | CTTCTTGATC | AATATACAAT | TTCCAAGGCC | TTTAATGCTC | ACGATGGTCC |
| 1401 | TCCTCTTGTC | CTGCGGGGT  | CACCCTCCTA | TGTCCCCGGT | TTTGCTATAA | GGACTTTATG | TGCATCGGT  |
| 1471 | CATCATAGGG | TTTTGTTG   | GTGGCAATG  | GCCTCTCTCA | TTTGCTATAA | TATCTGAGAT | TTTCGGCTT  |
| 1541 | AAGTACTACT | CGACATTGTA | TAACTTCGGG | TCAGTCGGA  | GCCCGATCGG | GTCTTACTTG | CTAAAGTTC  |
| 1611 | GGGTCGCAGG | GTATTTGTAC | GACGTGGAAG | CGGGTAAGCA | ATATAAGGCA | TTAGGAAAA  | CGAGAGTAGA |
| 1681 | AGGGCAAGAT | TTGAATTGCA | TAGGCACGTC | TTGTTTTAA  | TGTCTTTTA  | TAATAATTGC | CGCTGTAACT |
| 1751 | TGTTCGGTG  | TATTGGTCTC | GATGGTTTTG | GTGATCCGGA | TGTCTTTTA  | CCAAGAAGT  | TTACAAGAGT | pic30-2
| 1821 | AAAAGTTTAG | AGAAAAAGCG | TTAGCTGCCG | AGATGGAGAT | CCAAGCGGG  | GCCAGCGCCG | GCTGCAGCCA | DATATCTACA |
| 1891 | GGCTAAGGAA | GACAAGGATG | ATGTTAAAGG | CAAAGTAATA | GGAAAAGGAG | GGTAA      |            |

FIG. 2A

|     |          |          |          |          |          |         |
|-----|----------|----------|----------|----------|----------|---------|
| 1   | MVAASPGGSM | KSLTIQILTG | RWFMFFGSLL | IMSTAGATYM | FGIYSGDIKE |         |
| 51  | TLGYDQTTLN | LLSFFKDLGA | NVGVLAGLLN | EVTPPWFILL | IGAILNFFGY |         |
| 101 | FMIWLAVTER | ISKPQVWHMC | LYICVGANSQ | SFANTGSLVT | CVKNFPESRG | pic30-1 |
| 151 | VVLGILKGYV | GLSGAIITQL | YRAFYGEDTK | ELILMIGWLP | AIVSFAFLRT |         |
| 201 | IRIMKVKRQT | NELKVFYNFL | YISLGLATFL | MVVIINKLS | GFTQSEFGGS |         |
| 251 | AAVVIVLLLL | PIIVVILEEK | KLWKEKQVAL | NDPAPINVVT | EKPKLDSSEF |         |
| 301 | KDDDGEESKE | VVEKVKTPSC | WTTVFNPPER | GDDYTILQAL | FSVDMLILFL |         |
| 351 | ATICGVGGTL | TAIDNLGQIG | NSLGYPKRSV | STFVSLVSIW | NYYGRVVSGV |         |
| 401 | VSEIFLIKYK | FPRPLMLTMV | LLLSCAGHLL | IAFNVPGGLY | VASVIIGFCF |         |
| 451 | GAQWPLLFAI | ISEIFGLKYY | STLYNFGSVA | SPIGSYLLNV | RVAGYLYDVE | pic30-2 |
| 501 | AGKQYKALGK | TRVEGQDLNC | IGTSCFKLSF | IIIAAVTLFG | VLVSMVLVIR |         |
| 551 | TKKFYKSDIY | KKFREKALAA | EMEMAAPAAA | RSTVAKEDKD | DVKGKVIGKG |         |
| 601 | G          |            |            |            |            |         |

FIG. 2B

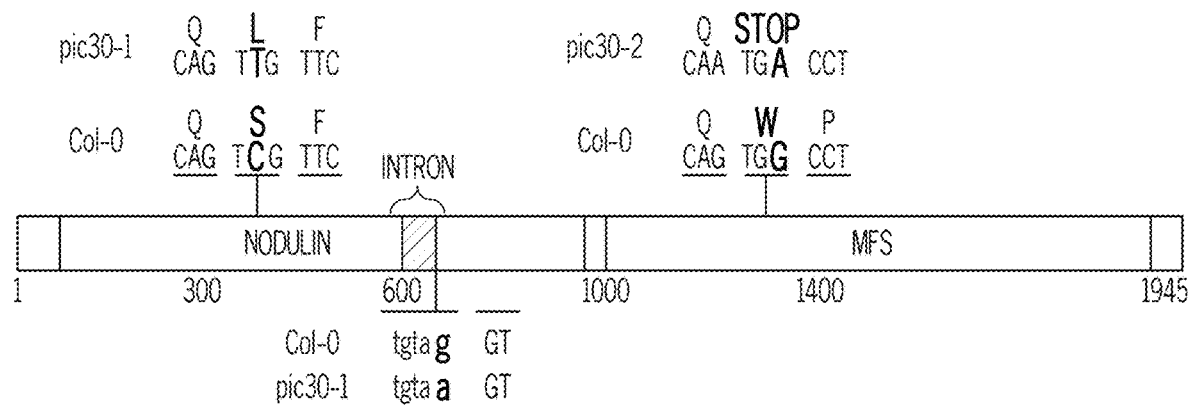

FIG. 2C

FIG. 10

DEVELOPMENT AND USE OF MODIFIED PLANTS AND SEEDS THAT ARE RESISTANT TO HERBICIDES AND ENVIRONMENTAL STRESS

CROSS-REFERENCE TO RELATED APPLICATIONS

This application claims priority to U.S. Provisional Patent Application No. 62/589,315, filed on Nov. 21, 2017. The entirety of the aforementioned application is incorporated herein by reference.

STATEMENT REGARDING FEDERALLY SPONSORED RESEARCH

This invention was made with government support under Grant No. IOS-0845305, awarded by the National Science Foundation. The government has certain rights in the invention.

BACKGROUND

Herbicides are widely used across the globe to protect various crops and promote their growth. However, many herbicides (e.g., auxinic herbicides) act non-specifically against various crops (e.g., a broad range of dicots), thereby limiting their use and applicability. At the same time, various sources of environmental stress (e.g., drought, high temperature, and UV radiation) cause heavy damages to crops and thereby reduce their yields. Embodiments of the present disclosure address the aforementioned problems.

SUMMARY

In some embodiments, the present disclosure pertains to a modified plant or seed that contains a mutated gene. The mutated gene includes, without limitation, a pic30 mutant, a mutant homolog of pic30, and combinations thereof. The modified plant or seed is resistant to at least one herbicide, such as picloram. In some embodiments, the modified plant or seed may also be resistant to one or more sources of environmental stress, such as drought. In some embodiments, the modified plant or seed is a dicot, such as a tomato.

In further embodiments, the present disclosure pertains to methods of controlling the growth of weeds in a field that contains a modified plant or seed of the present disclosure. The methods involve applying at least one herbicide to the field, where the modified plant or seed in the field shows resistance to the herbicide.

In some embodiments, the weed growth control methods of the present disclosure also include a step of applying the modified plant or seed to the field. In some embodiments, the weed growth control methods of the present disclosure also include a step of growing the modified plant or seed in the field. In various embodiments, the applying or growing steps can occur before, during or after applying the herbicide to the field.

In additional embodiments, the present disclosure pertains to methods of developing the modified plants or seeds of the present disclosure. In some embodiments, such methods include a step of introducing a mutated gene to a plant or seed, where the mutated gene includes, without limitation, a pic30 mutant, a mutant homolog of pic30, and combinations thereof. In some embodiments, the mutated gene is a transgene (e.g., a transgene of a pic30 mutant and/or its homolog) that is introduced into the plant or seed by various methods, such as floral-dip transformation, callus transformation, tissue transformation, and other similar methods. In some embodiments, the mutated gene is an endogenous gene that is introduced into the plant or seed by various methods, such as chemical mutation.

FIGURES

Figure 1B:
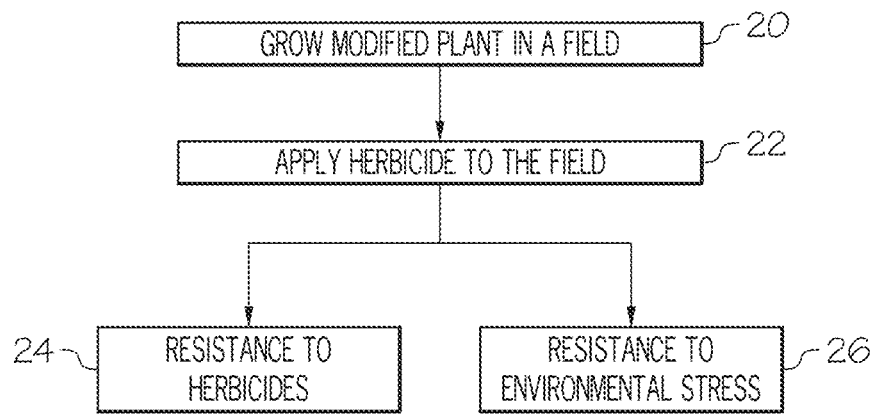

FIGS. 1A and 1B provide schemes of methods of forming modified plants or seeds that are resistant to herbicides and environmental stress (FIG. 1A), and methods of controlling the growth of weeds in a field that contains the modified plants or seeds (FIG. 1B).

Figure 2D:
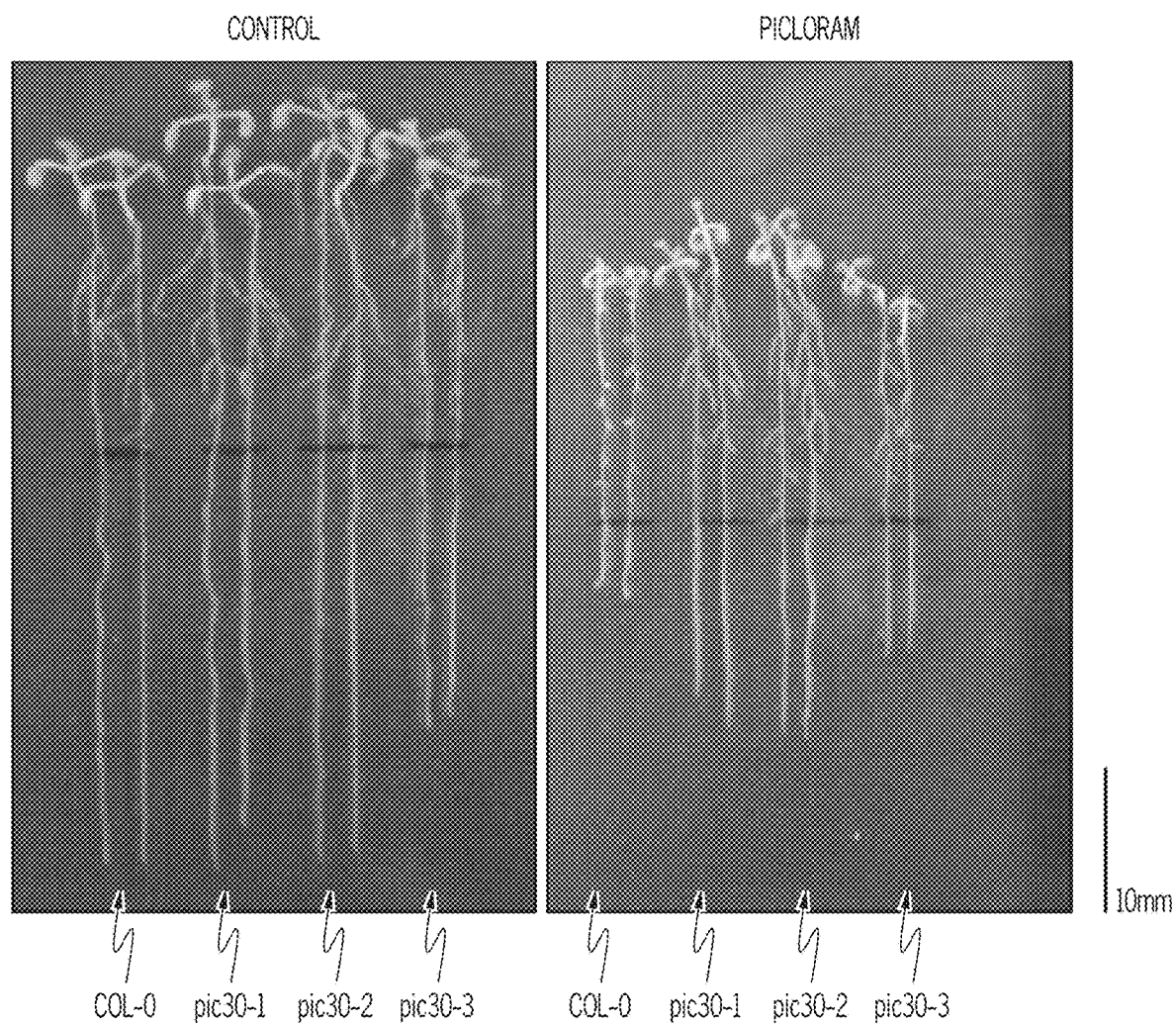
Figure 2E:
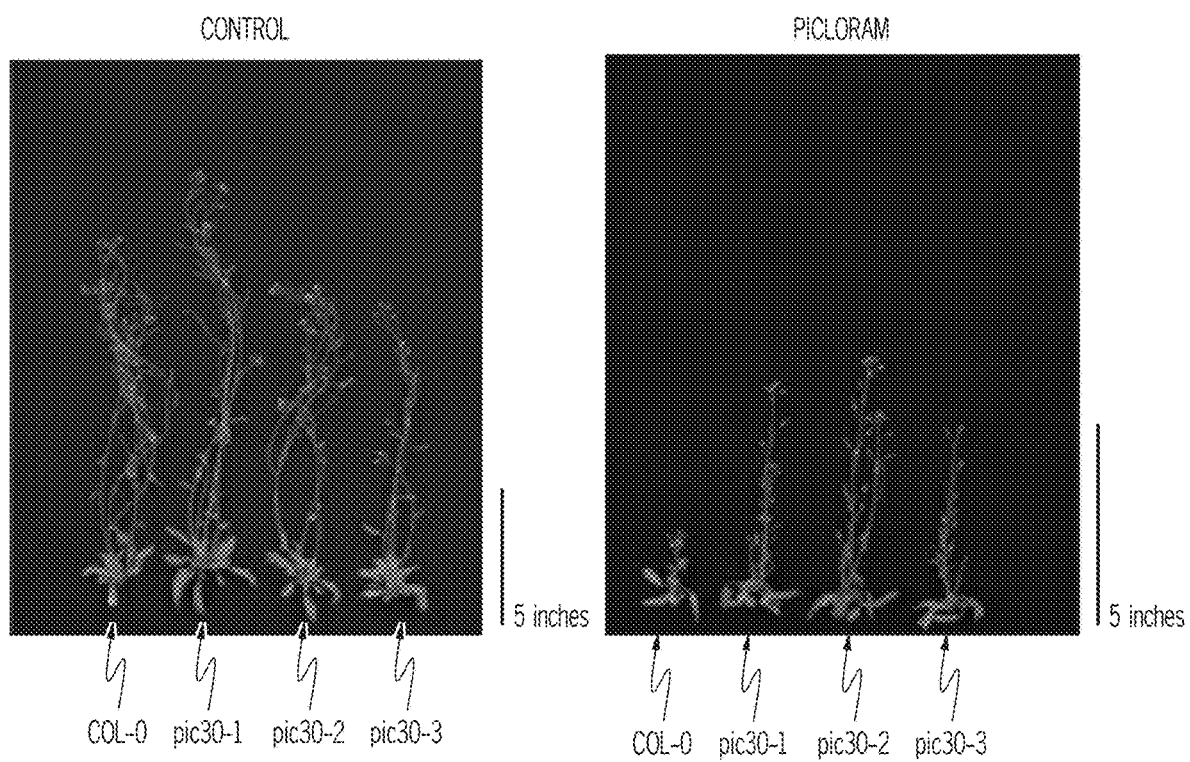
Figure 2F:
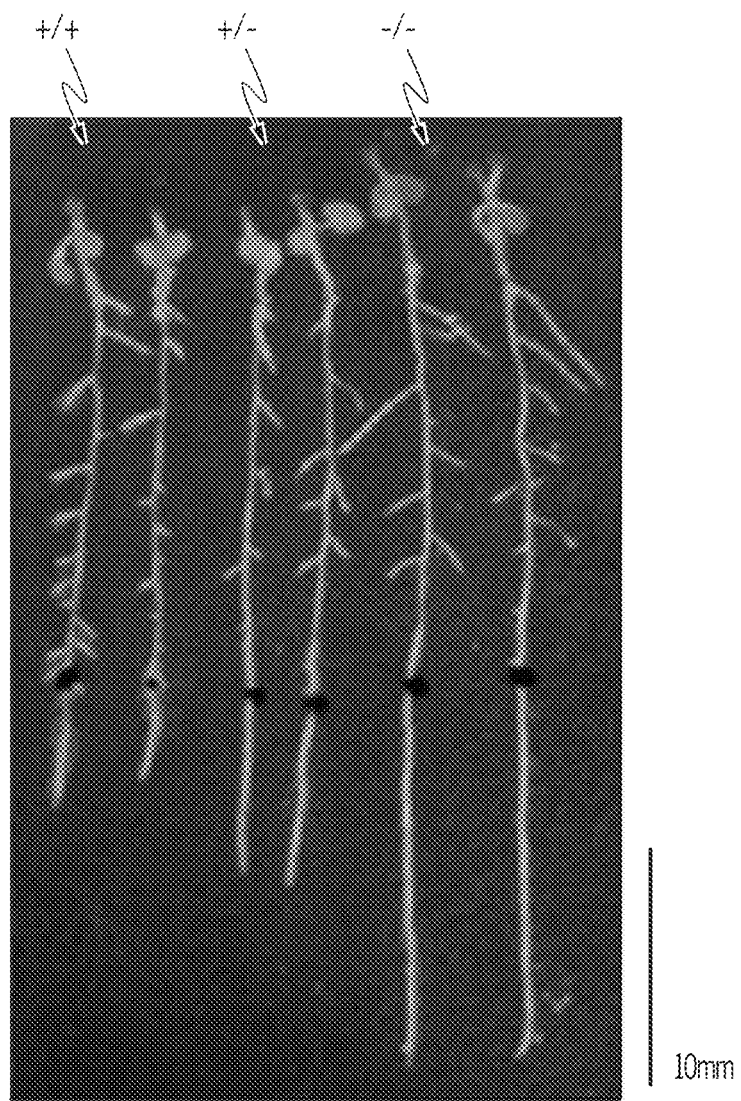

FIGS. 2A, 2B, 2C, 2D, 2E and 2F show that pic30 mutant plants are insensitive to picloram. FIG. 2A shows the nucleotide sequence of wild type PIC30 with nucleotides that have been changed in pic30 mutants highlighted to represent pic 30-1 (SEQ ID NO: 1), pic 30-2 (SEQ ID NO: 2), and pic 30-3 (SEQ ID NO: 3). Lowercase letters represent intron sequences. FIG. 2B shows the predicted wild type protein sequence of PIC30 with amino acid residues that have been changed in pic30 mutants highlighted, including PIC 30-1 (SEQ ID NO: 4), PIC 30-2 (SEQ ID NO: 5), and PIC 30-3 (SEQ ID NO: 6) (PIC 30-3 cannot be shown here as the mutation is in the intron sequence). FIG. 2C shows a schematic representation of wild type PIC30 gene (Col-0) and pic30 mutations. Changes in both nucleotide and corresponding amino acid residues are highlighted in red. The PIC30 gene contains an $NH_2$-terminal nodulin-like (NOD)-domain and a COOH-terminal major facilitator superfamily (MFS) domain. pic30-1 is a missense mutation in the NOD-domain, pic30-2 is non-sense mutation in the MFS domain, and pic30-3 is a splice site mutation. Mutations in nucleotide sequence and related changes in amino acid residues are given in bold letters. FIG. 2D shows that the primary root growth of pic30-1, pic30-2 and pic30-3 mutants are insensitive to picloram. FIG. 2E shows that all three pic30 allelic mutants are insensitive to foliar application of picloram. FIG. 2F shows that picloram insensitive phenotype of pic30 mutants inherits as a semi-dominant trait (only pic30-3 is shown). For the root growth assay, 5 day-old seedlings were transferred on to the ATS media (for mock treatment) or ATS with 12.5 pM picloram. After 4 days of incubation, images were acquired using NIKON SMZ1500 stereomicroscope. For foliar picloram application, approximately 3 week-old plants were homogenously sprayed with 200 g/ha of picloram. Images were acquired 18 days after the treatment.

Figure 3A:
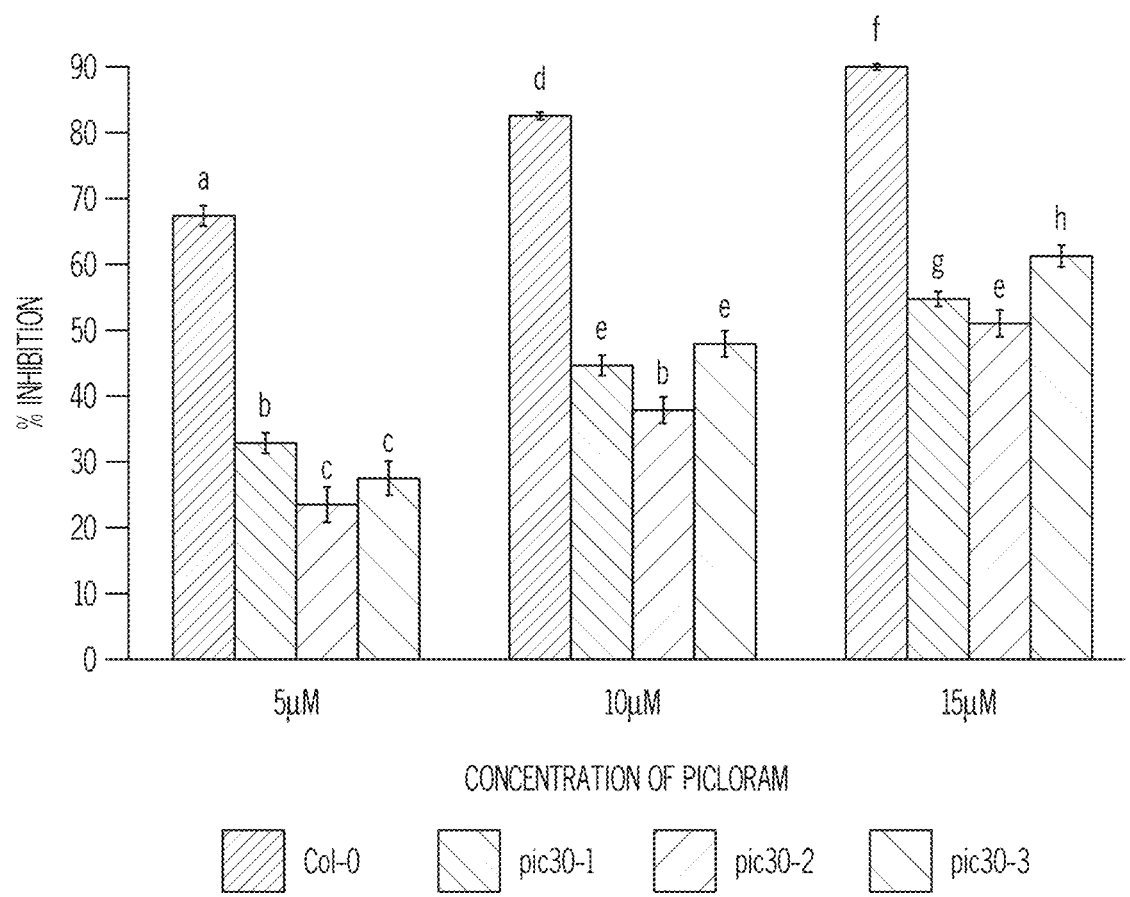
Figure 3B:
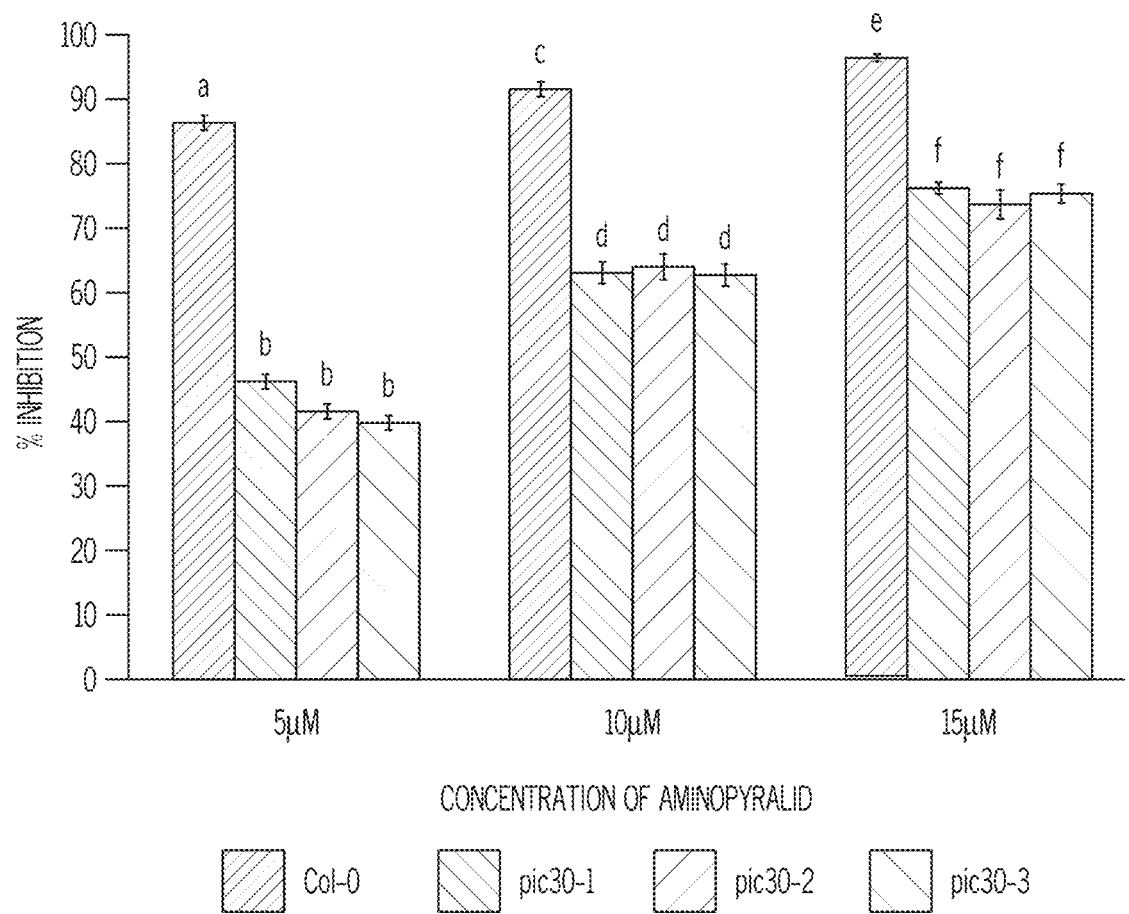
Figure 3C:
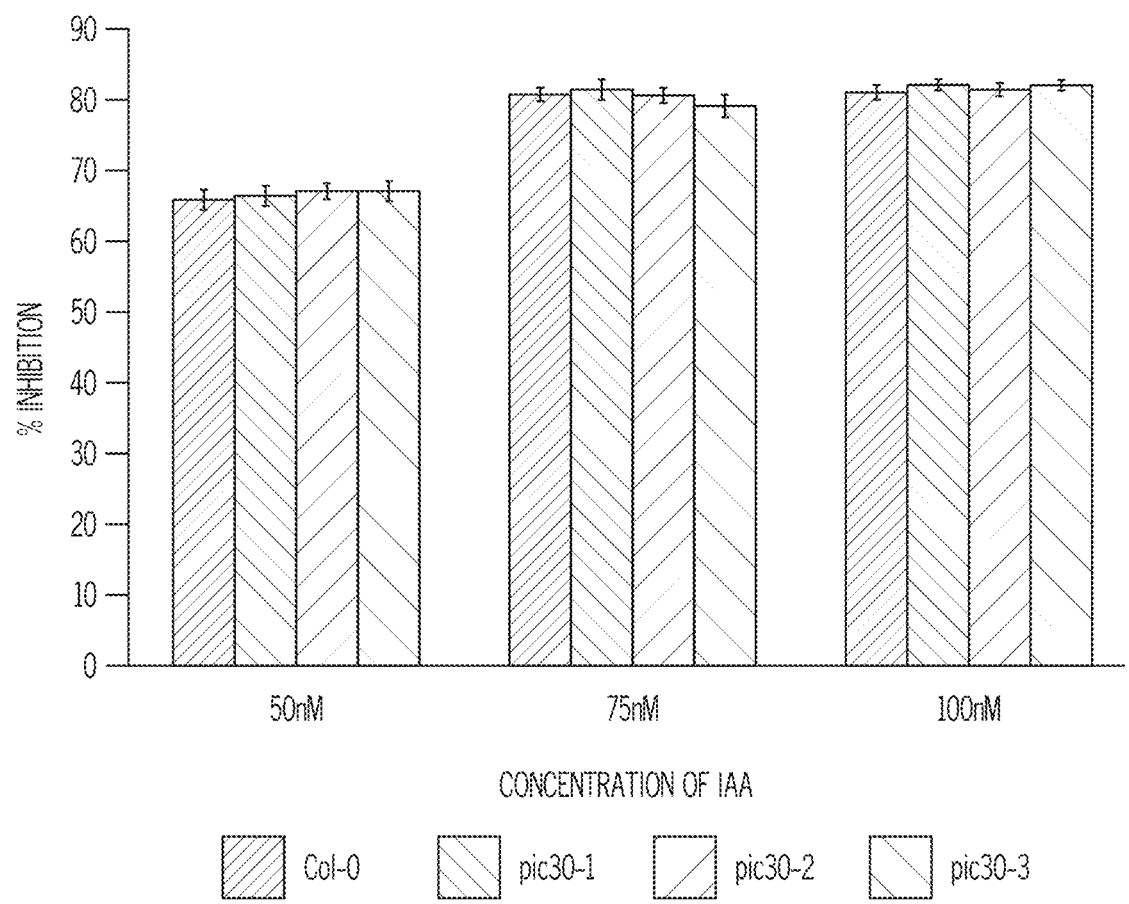
Figure 3D:
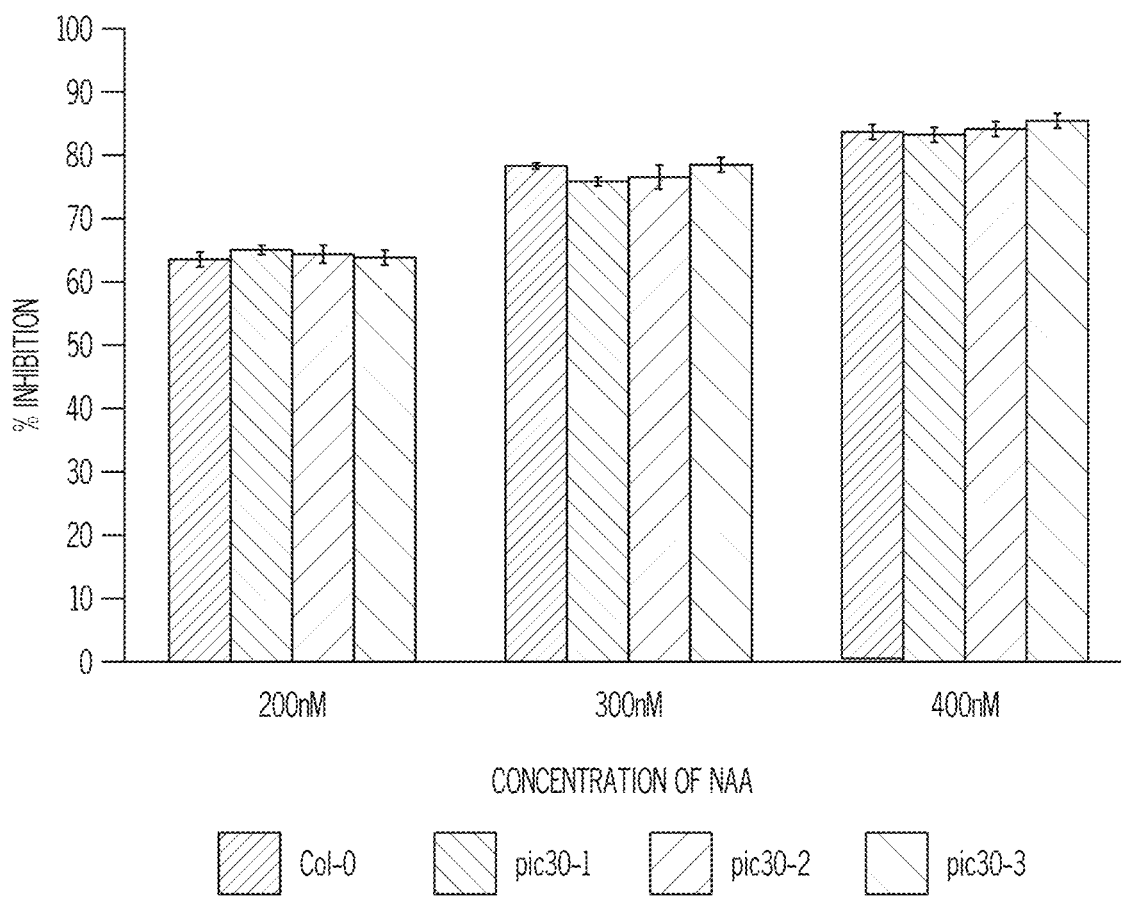
Figure 3E:
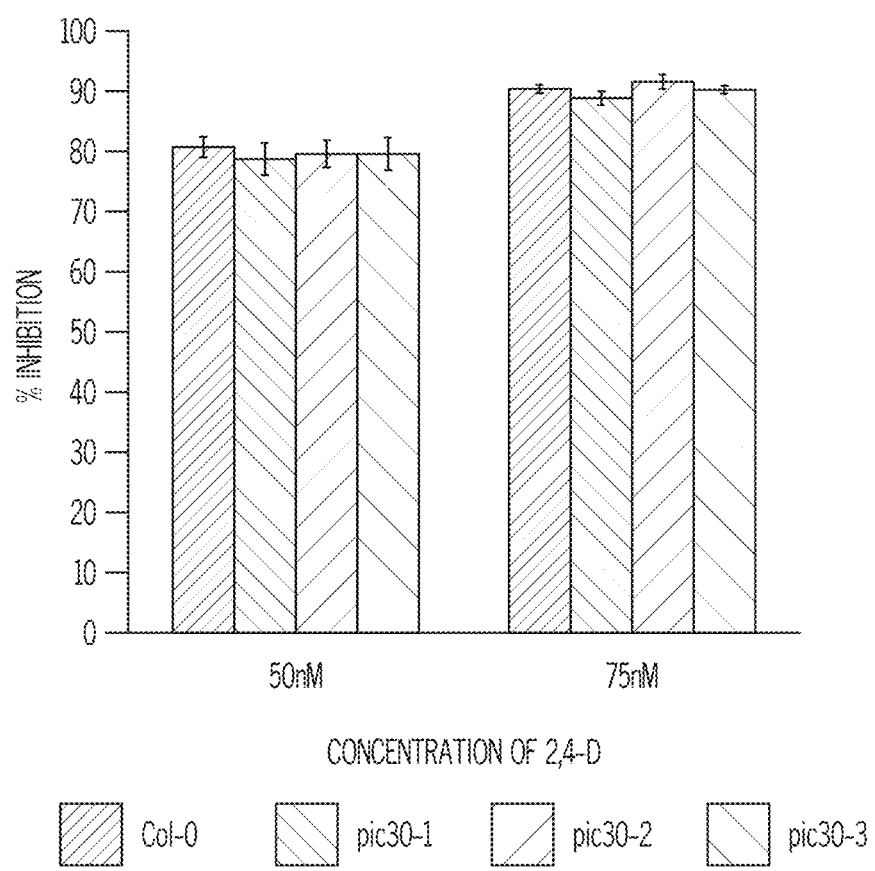
Figure 3F:
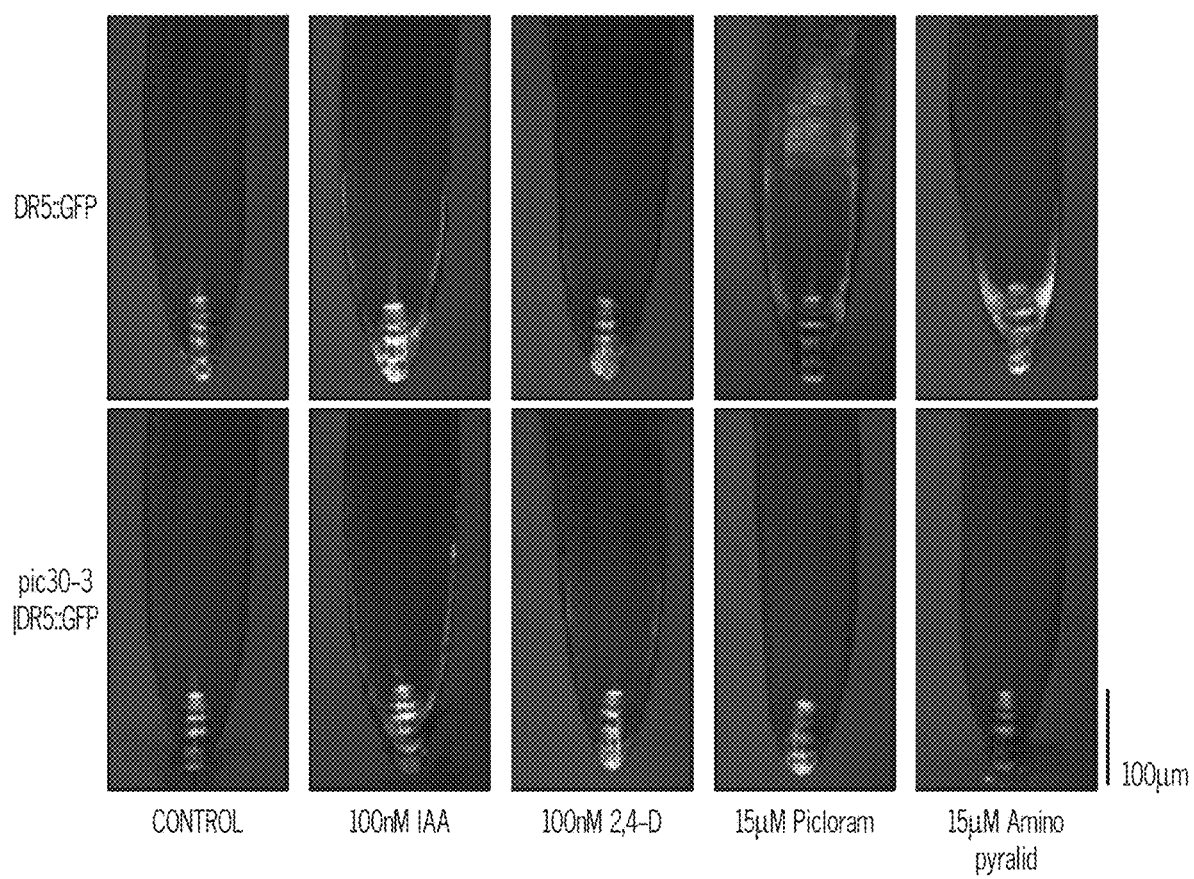

FIGS. 3A, 3B, 3C, 3D, 3E and 3F show that pic30 mutant plants are selectively insensitive to picolinate class of auxinic herbicides. The data show that the primary root growth of pic30 mutants is insensitive to picloram (FIG. 3A) and aminopyralid (FIG. 3B), but shows wild type sensitivity to IAA (FIG. 3C), 1-NAA (FIG. 3D) and 2,4-D (FIG. 3E). Four day-old seedlings were transferred to ATS media (control) or ATS containing indicated concentrations of different auxins. Root lengths were measured after 4 days of incubation. Each data point reflects the mean percentage inhibition (MPI), and bars represent standard percentage error (SPE). In pic30-3, auxin induced DR5::GFP expression is selectively insensitive to picloram and aminopyralid (FIG. 3F). Five day-old seedlings were transferred on to ATS media (control) or ATS media with indicated concentrations of different auxinic chemicals. Confocal images were acquired 20 hours after the incubation.

Figure 4A:
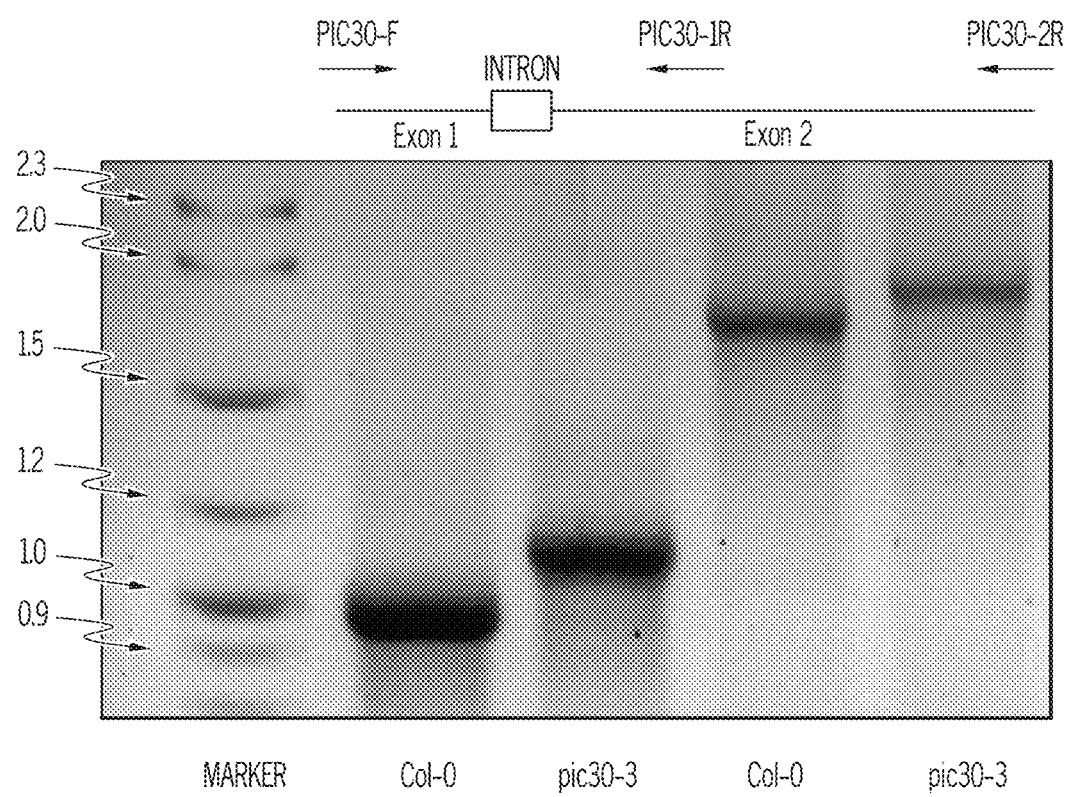
Figure 4B:
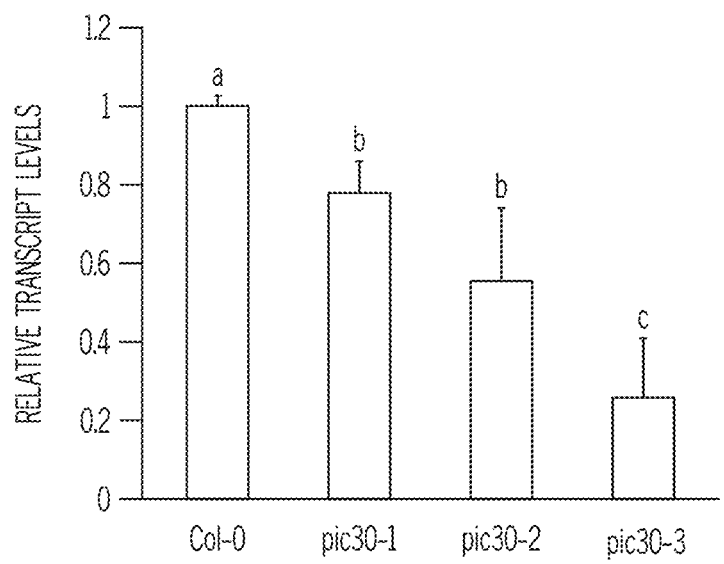
Figure 4C:
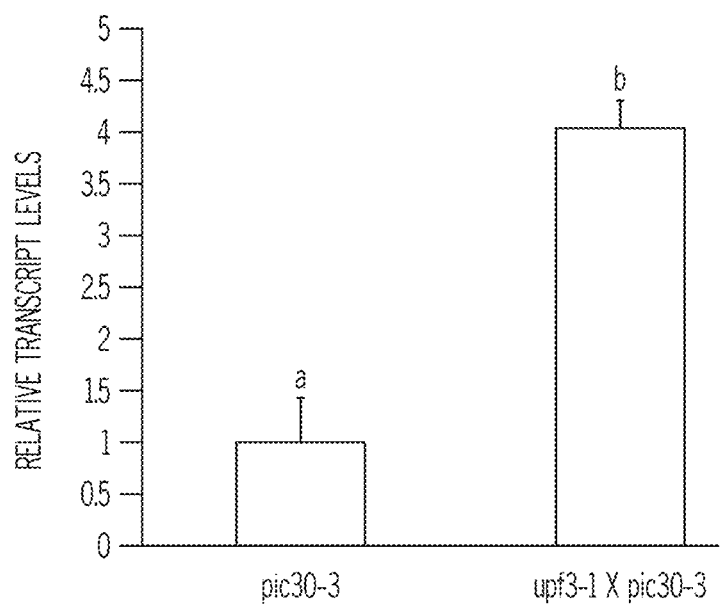
Figures 5D, 5E, 5F:
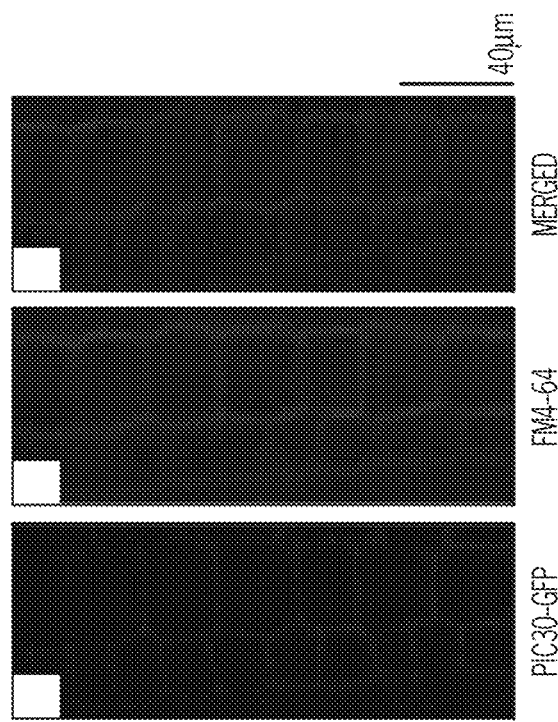
Figures 5A, 5B, 5C:
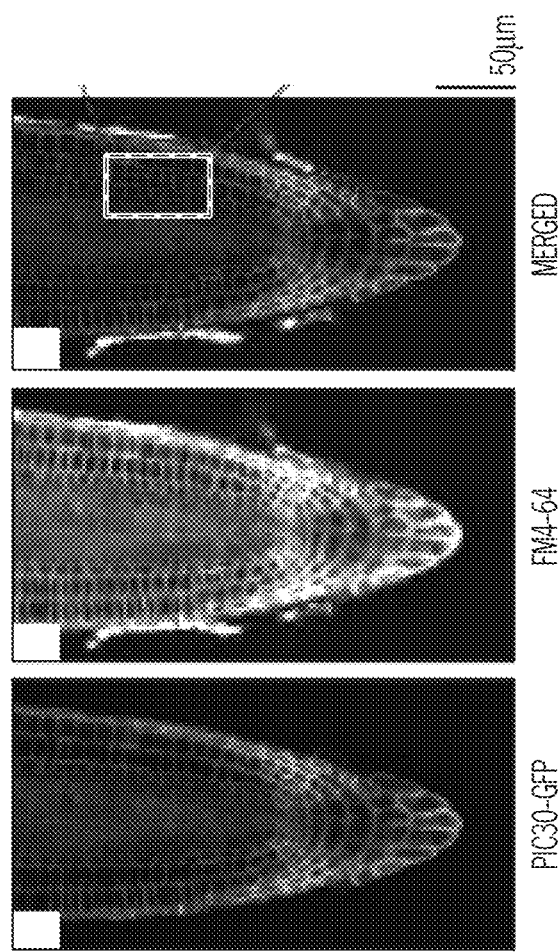

FIGS. 4A, 4B, and 4C show that the pic30 transcript is degraded through the NMD pathway. FIG. 4A shows that the pic30-3 transcript is defective in splicing. RT-PCR were performed with two different primer combinations, and the resulting PCR products were separated on 1% agarose gel. FIG. 4B shows that the abundance of pic30 transcript in pic30-1, pic30-2 and pic30-3 is significantly lower than that of the PIC30 in wild type. FIG. 4C shows that the pic30-3 transcript is stabilized in NMD mutant upf3-1. qRT-PCR was performed with cDNA prepared from total RNA extracted from 7 day old seedlings. Relative expression was normalized to the expression of either PIC30 in wild type (FIG. 4B) or pic30 in pic30-3 (FIG. 4C). Each data point represents the mean of three values and the bar represents standard deviation (SD).

FIGS. 5A, 5B, 5C, 5D, 5E, and 5F show that PIC30-GFP localizes to the plasma membrane. PIC30-GFP preferentially localizes to plasma membrane in root cells (FIGS. 5A-F). Five day-old transgenic seedlings carrying 35S$_{pro}$:: PIC30-GFP were imaged using either a 20× water lens (FIGS. 5A-C) or a 60× oil lens (FIGS. 5D-F) using a confocal microscope.

Figure 6A:
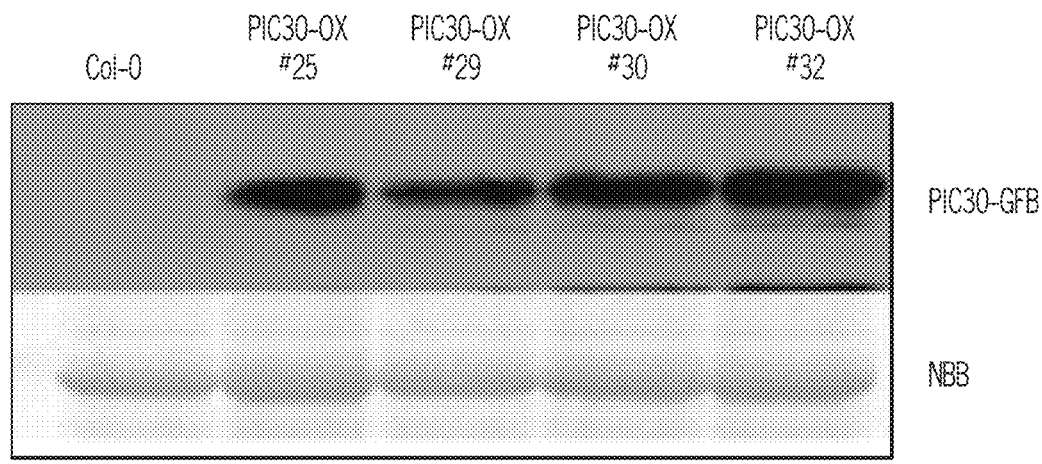
Figure 6B:
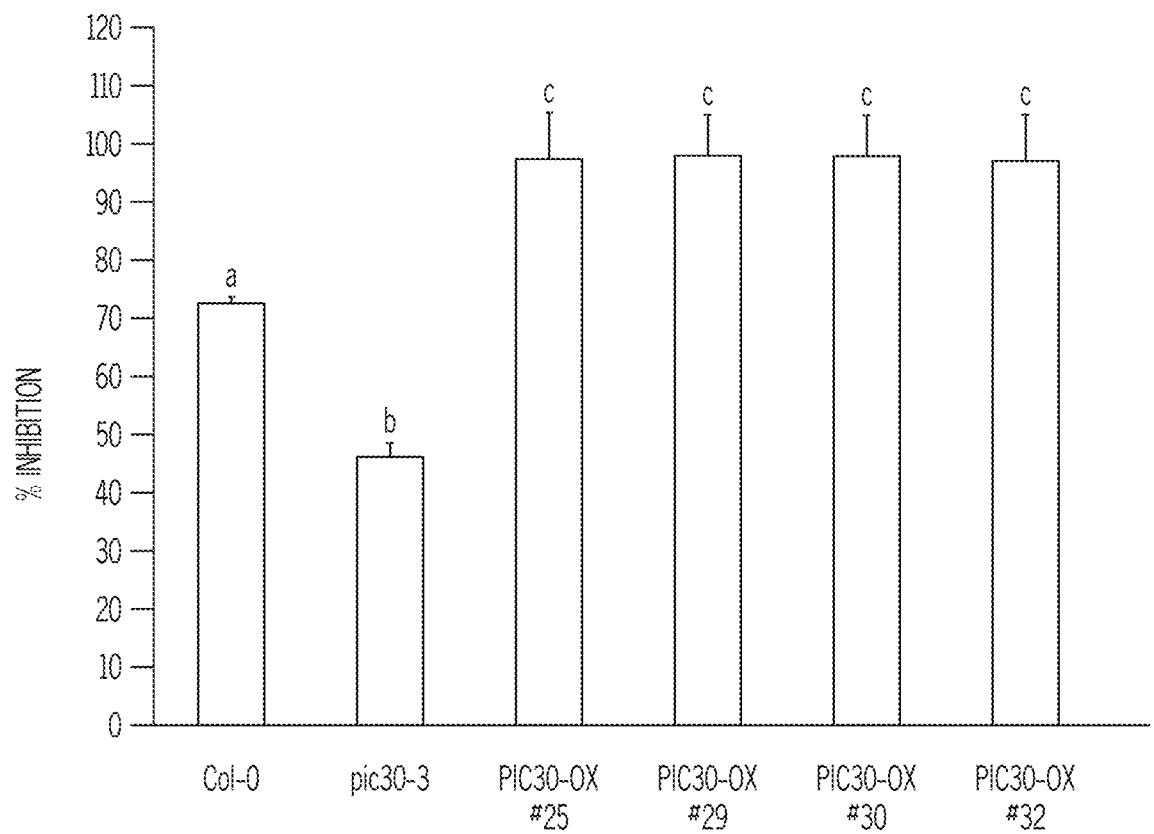
Figure 6C:
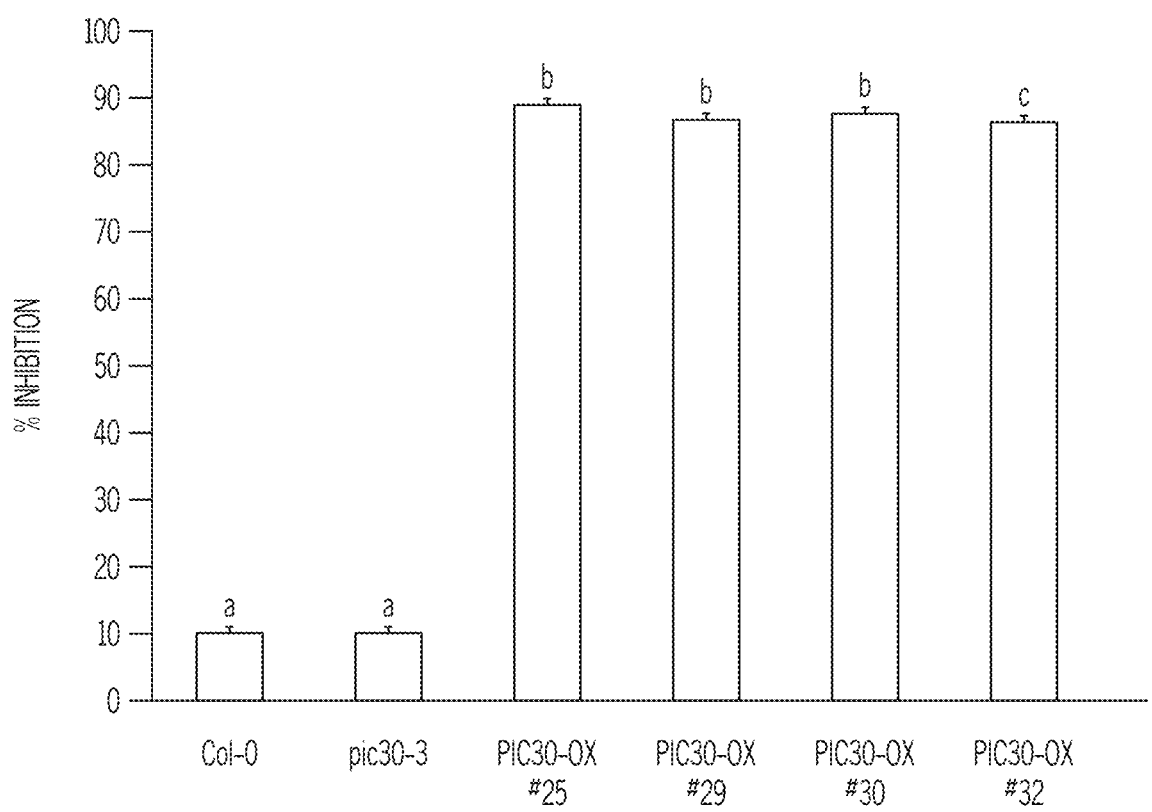
Figure 6D:
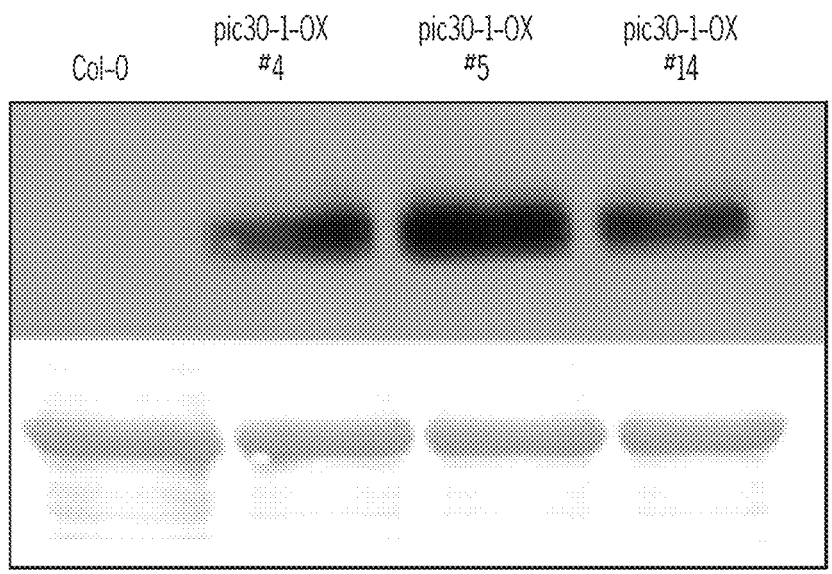
Figure 6E:
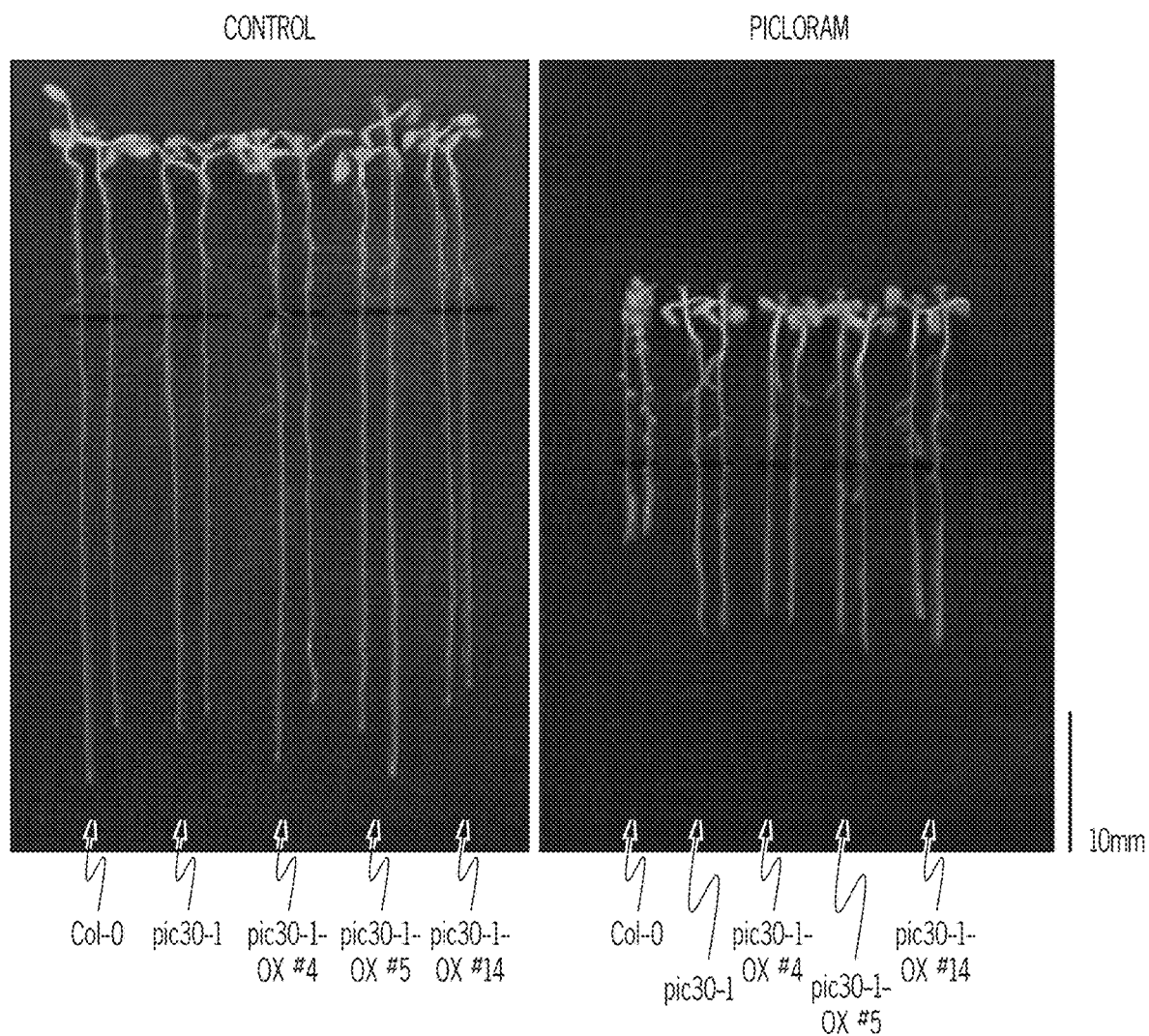

FIGS. 6A, 6B, 6C, 6D, and 6E show that the ectopic expression of PIC30 complements picloram sensitivity. FIG. 6A shows the expression of PIC30-GFP in four independent PIC30-OX transgenic lines. It is also shown that PIC30-OX lines are hypersensitive at micromolar (FIG. 6B) and nanomolar (FIG. 6C) concentrations of picloram. FIG. 6D shows the expression of pic30-1-myc in three independent pic30-1-OX transgenic lines. FIG. 6E shows that pic30-1-OX lines are insensitive to picloram. For immunoblotting, equal amounts (40 pg) of total protein was separated and transferred to PVDF membrane. Immunoblotting was done using either anti-GFP or anti-Myc antibodies. For root growth assay, 4 day-old seedlings were transferred to ATS (control) media and ATS media containing either 10 pM (FIG. 6B) or 100 nM (FIG. 6C) of picloram and root lengths were measured after 4 days of incubation. Each data point reflects the mean MPI, and bars represent SPE.

Figure 7A:
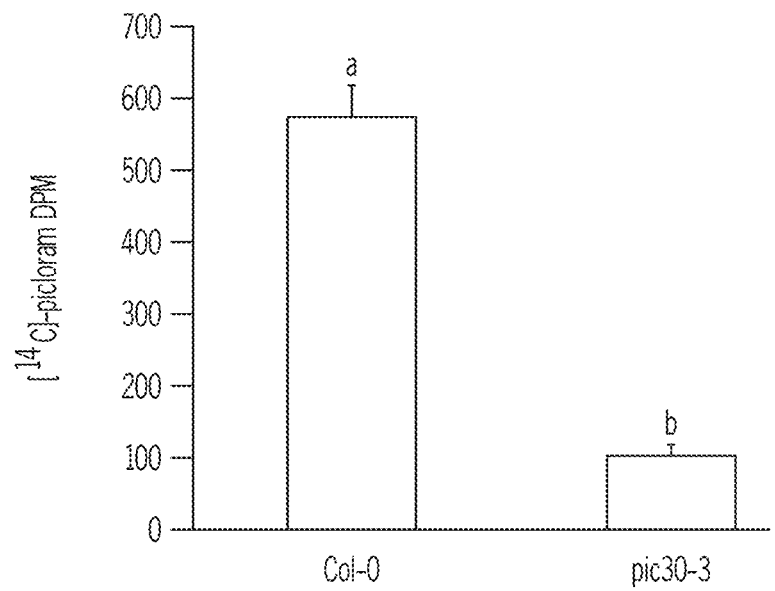
Figure 7B:
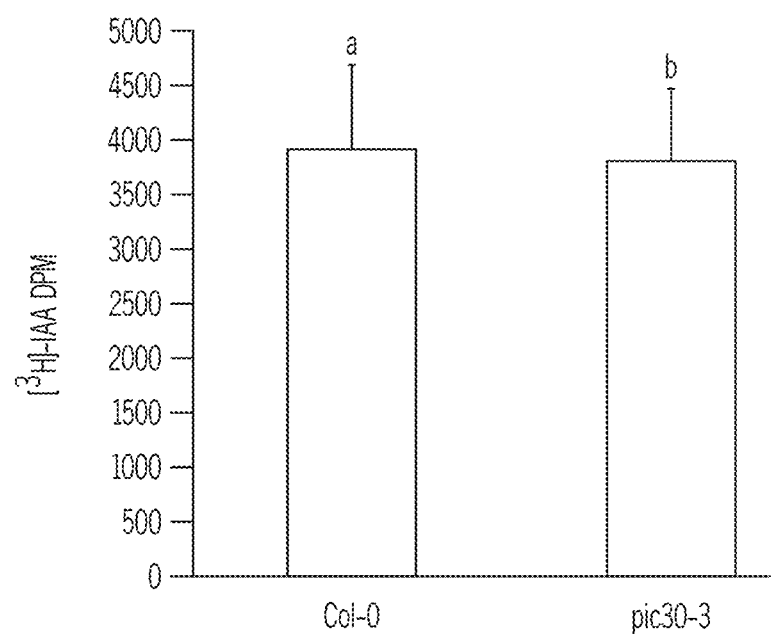
Figure 7C:
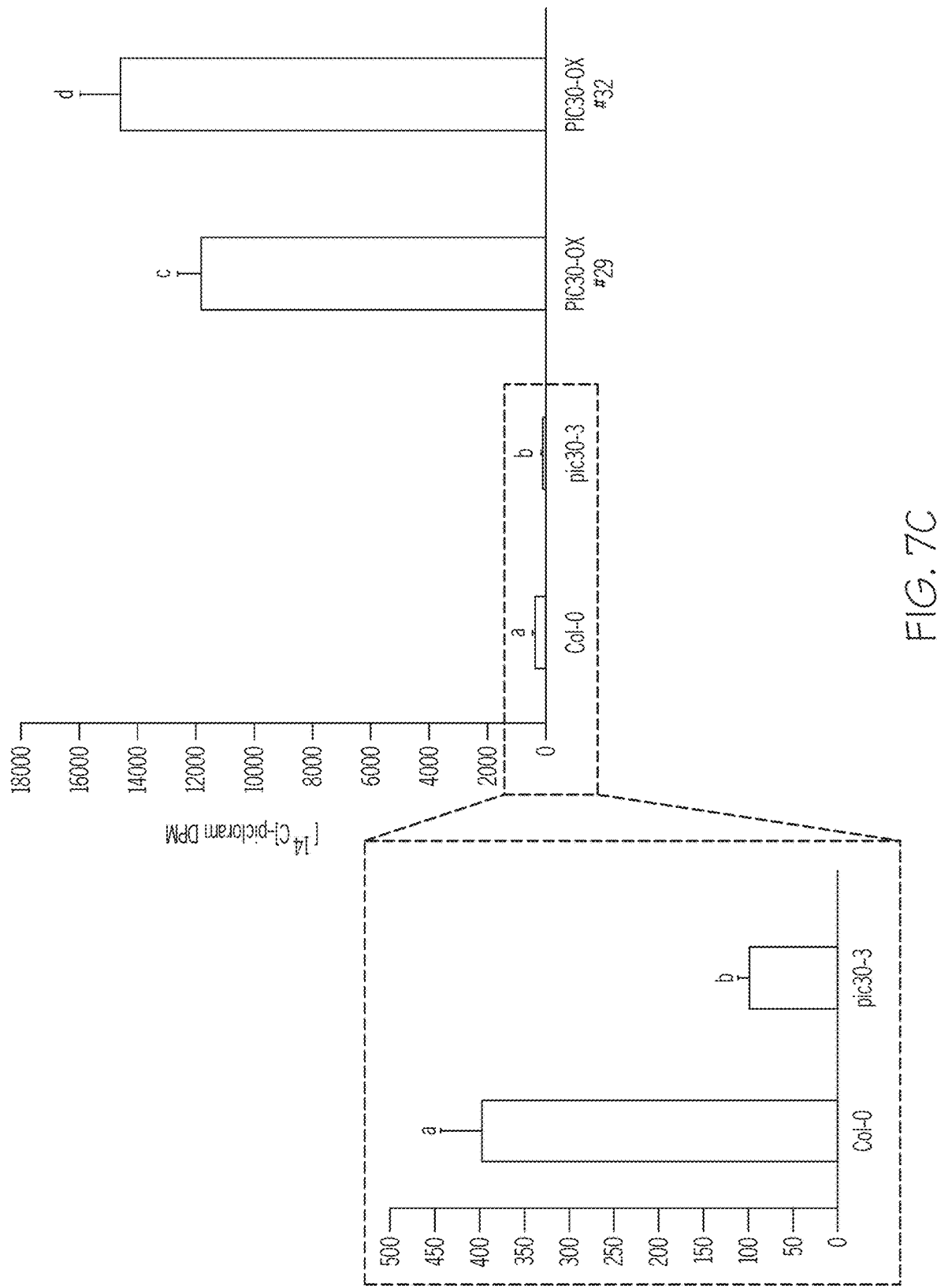

FIGS. 7A, 7B, and 7C show that the pic30-3 mutant is defective in picloram uptake. FIGS. 7A-B show that the pic30-3 mutant is defective in uptake of picloram (FIG. 7A), but not IAA (FIG. 7B). FIG. 7C shows that picloram uptake is enhanced in PIC30-OX transgenic lines. Apical root sections (15 mm) were incubated in transport assay buffer (TAB) containing radioactive $^{14}$C-picloram or $^{3}$H-IAA. After incubation, root sections were rinsed thoroughly using ice-cold TAB buffer and radioactivity was measured using the scintillation counter. Each data point show mean of three independent values, and bar represents SD.

Figure 8A:
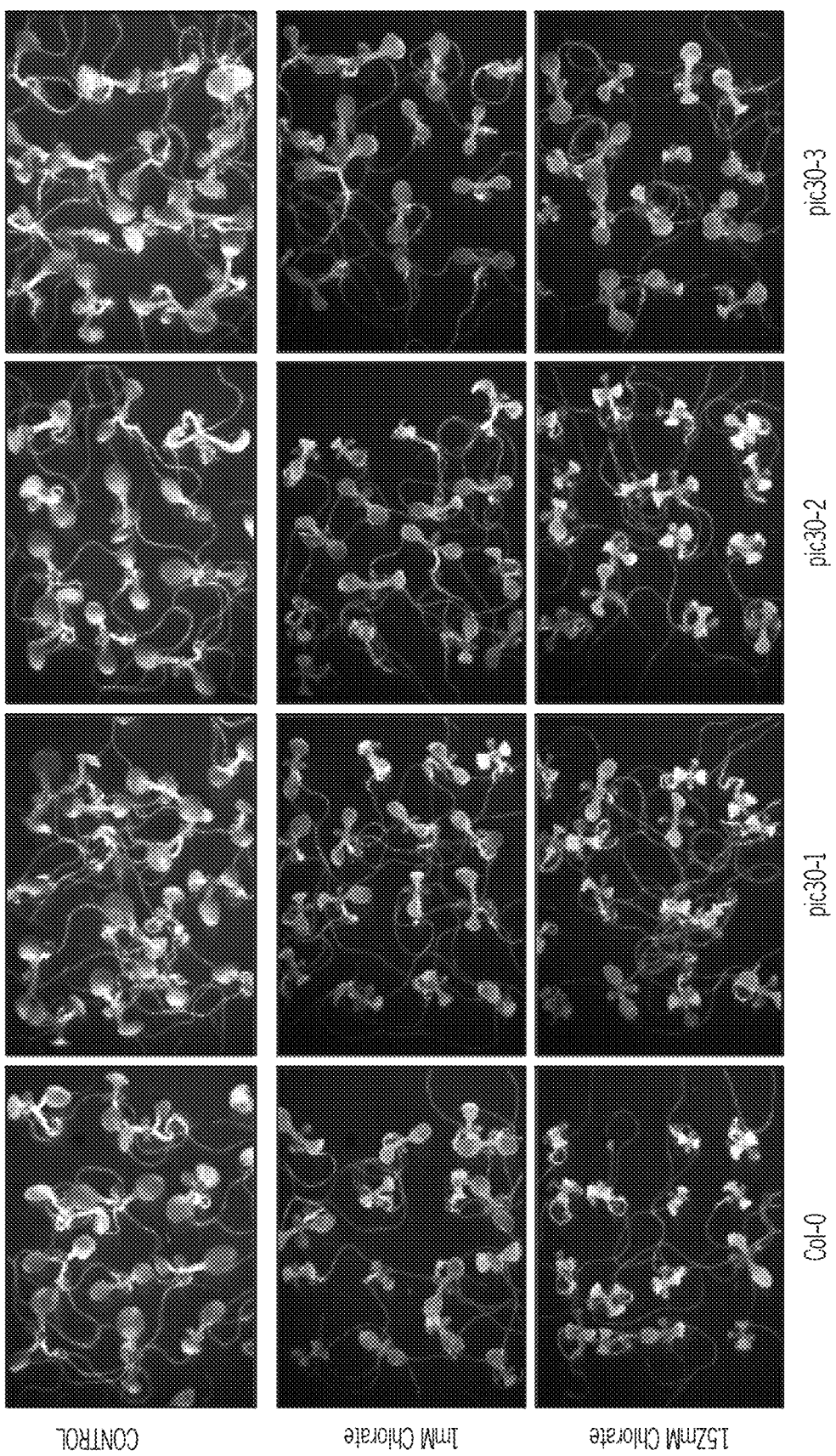
Figure 8B:
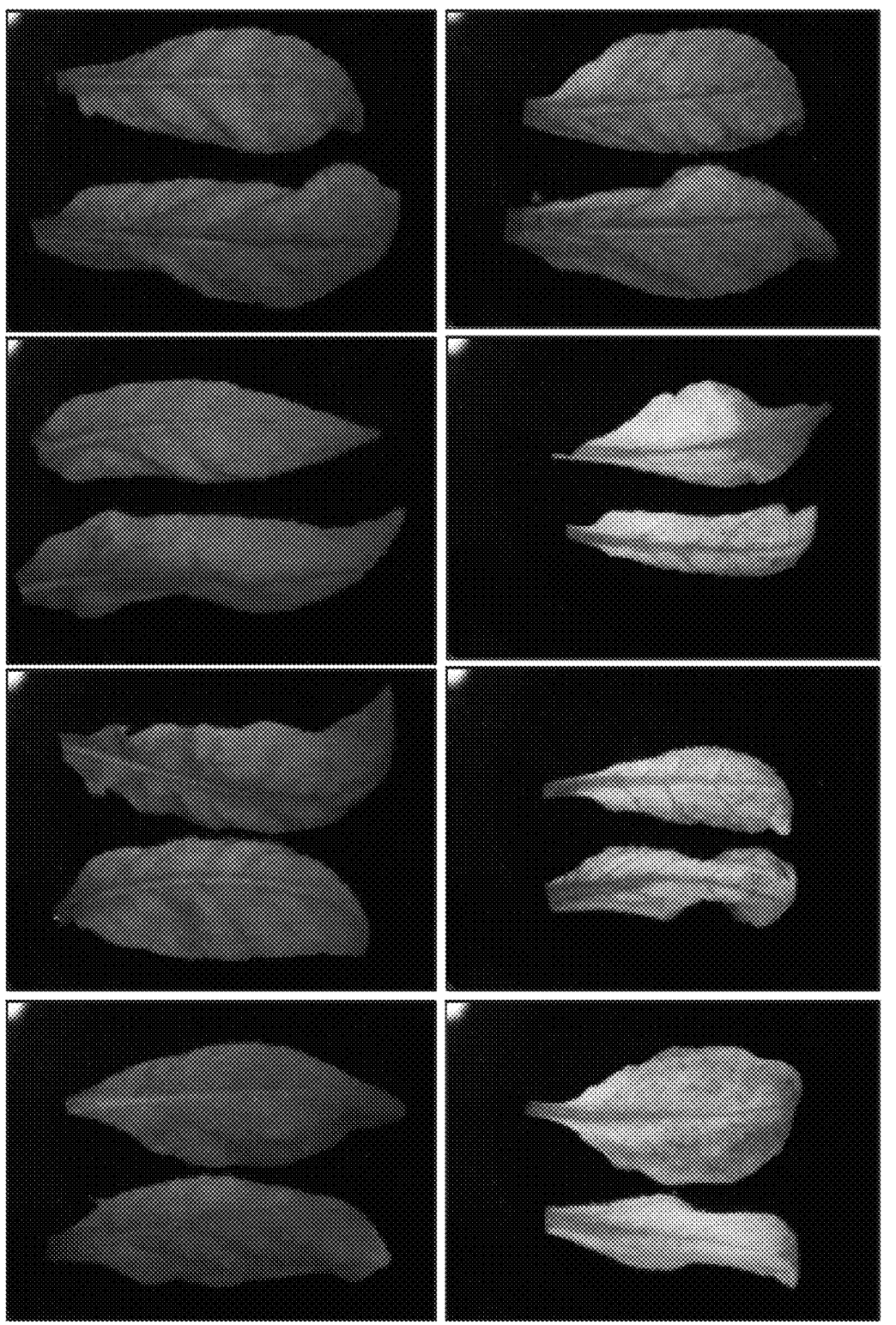
Figure 8C:
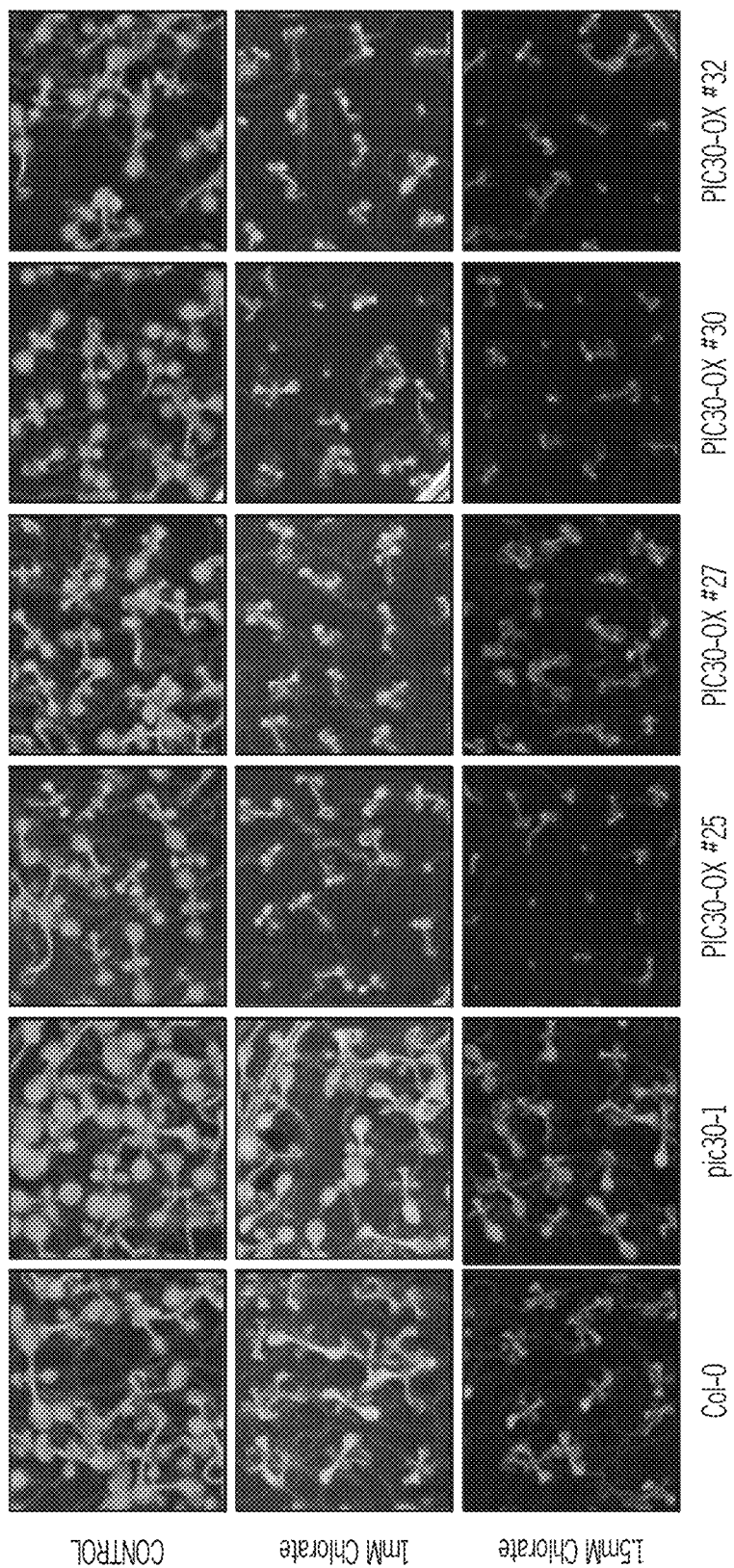
Figure 8D:
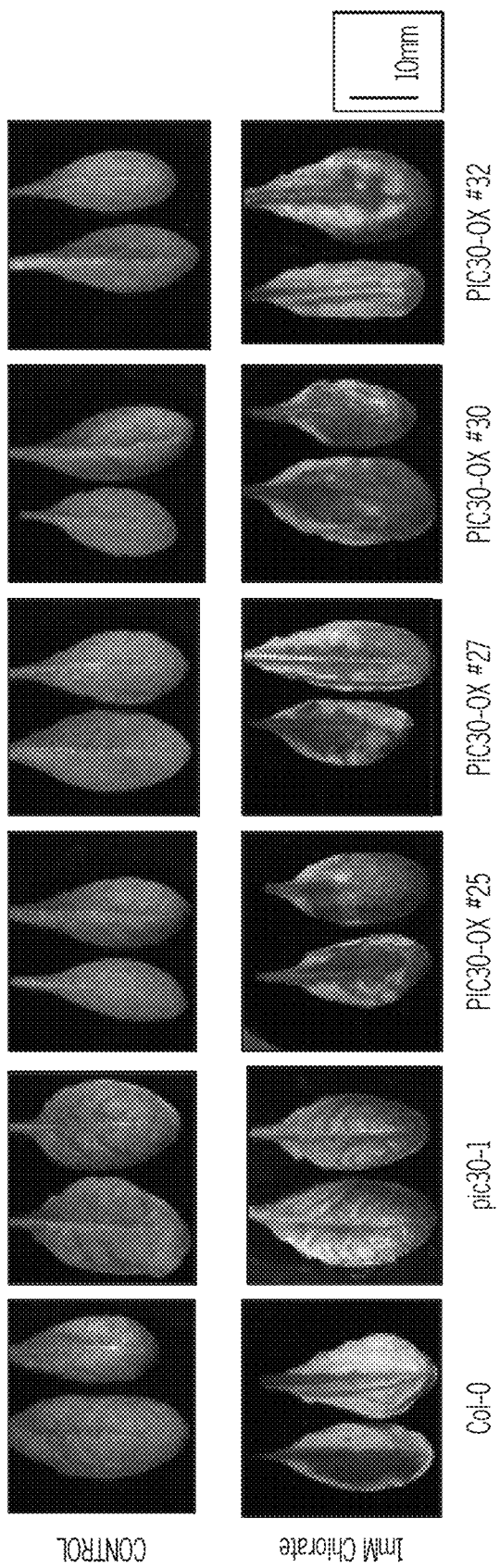

FIGS. 8A, 8B, 8C, and 8D show that pic30-3 is insensitive to chlorate ions. pic30-3 but not pic30-1 or pic30-2 mutant seedlings (FIG. 8A) or plants (FIG. 8B) are insensitive to chlorate induced necrosis and bleaching. Overexpression of PIC30 in pic30-3 complements chlorate sensitivity at both seedling (FIG. 8C) and adult stages (FIG. 8D). For the chlorate sensitivity assay during seedling stage, seeds were plated either on ATS (control) or ATS containing indicated concentrations of sodium chlorate and incubated for 9 days. For chlorate sensitivity test during the adult stage, approximately 3 week old plants were irrigated with 1 mM sodium chlorate on every alternative day. Images were acquired 12 days after the first sodium chlorate treatment.

Figure 9A:
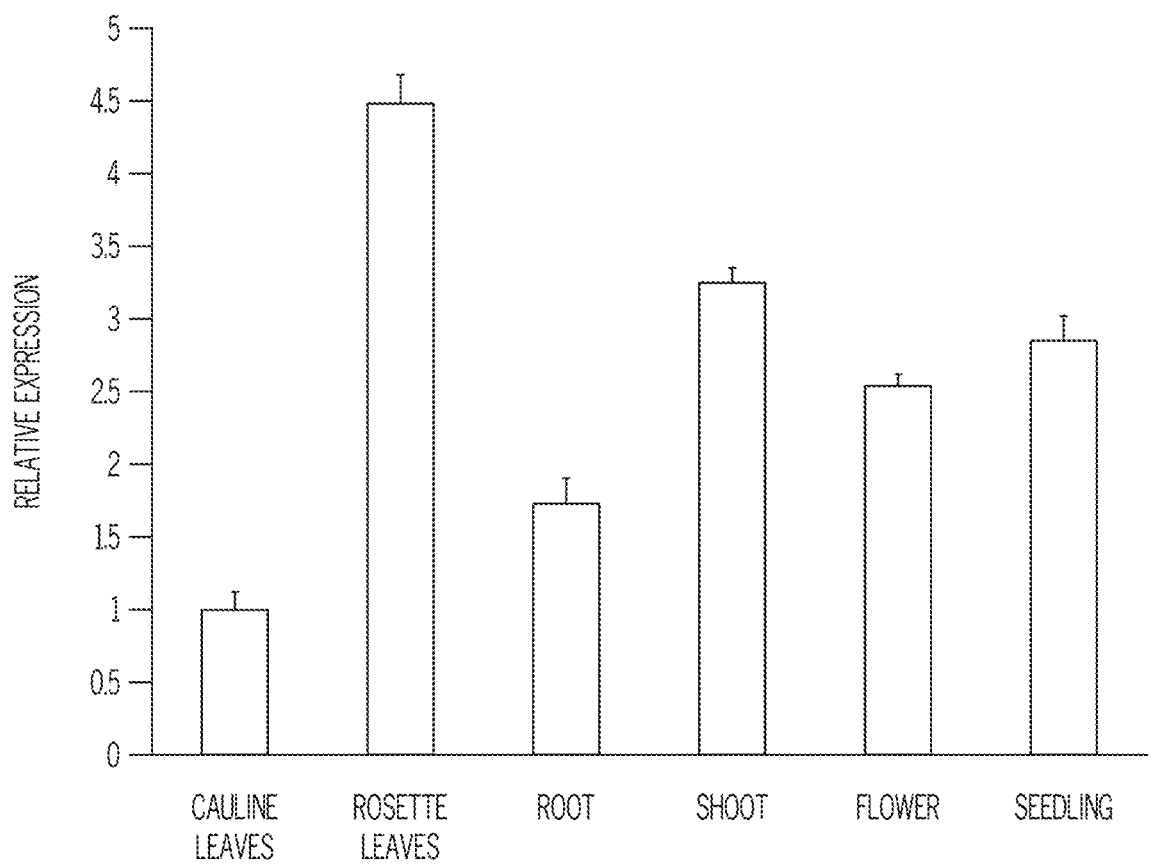
Figure 9B:
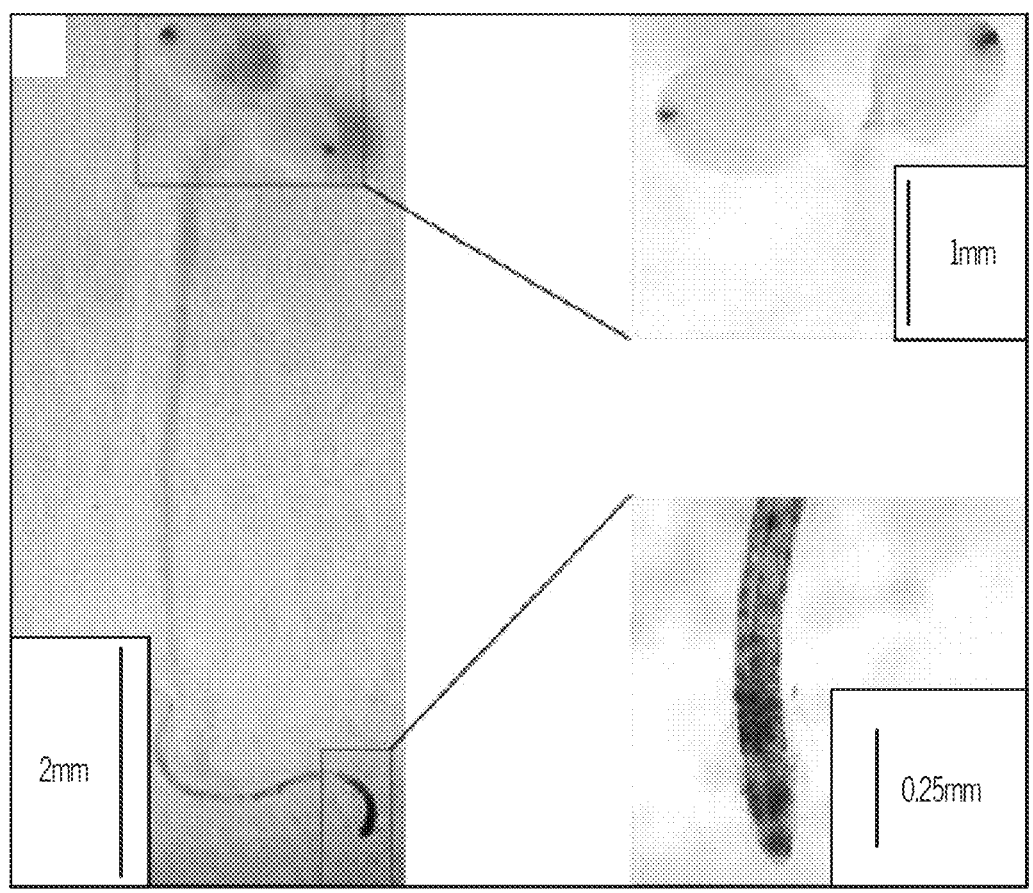
Figure 9C:
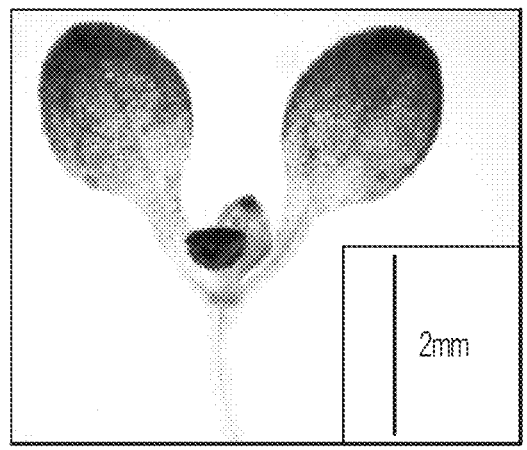
Figure 9D:
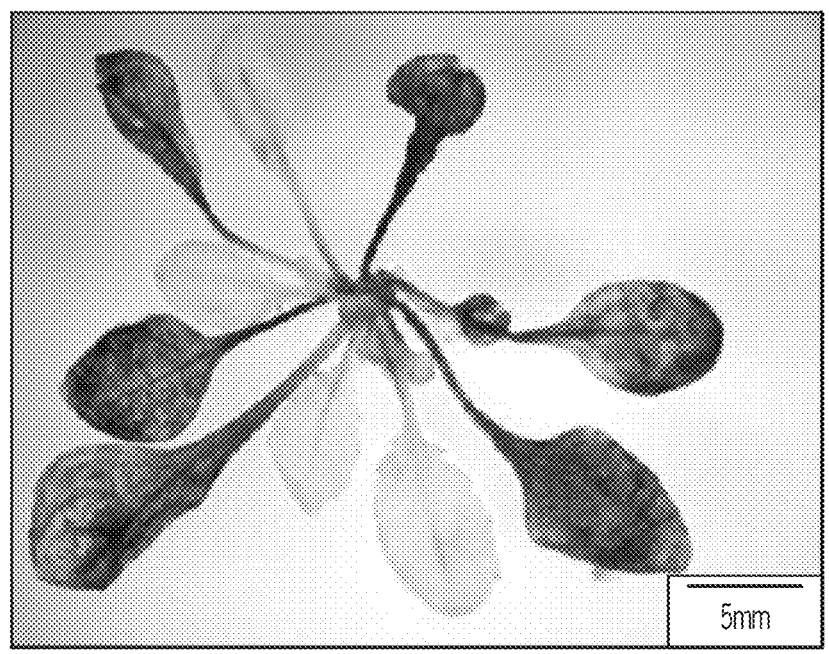
Figure 9E:
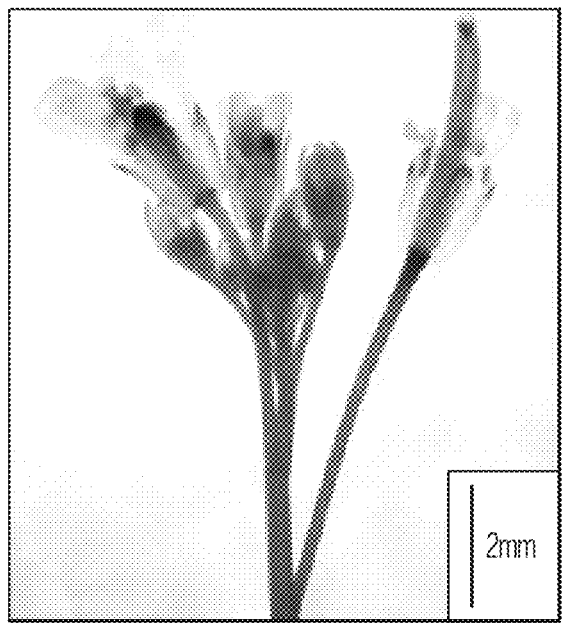
Figure 9F:
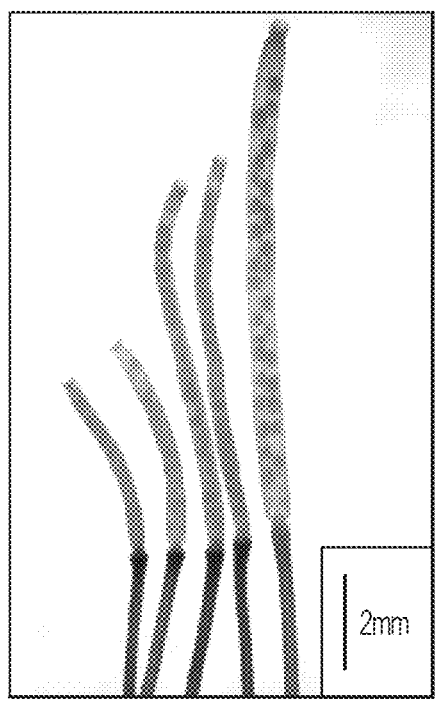
Figure 9G:
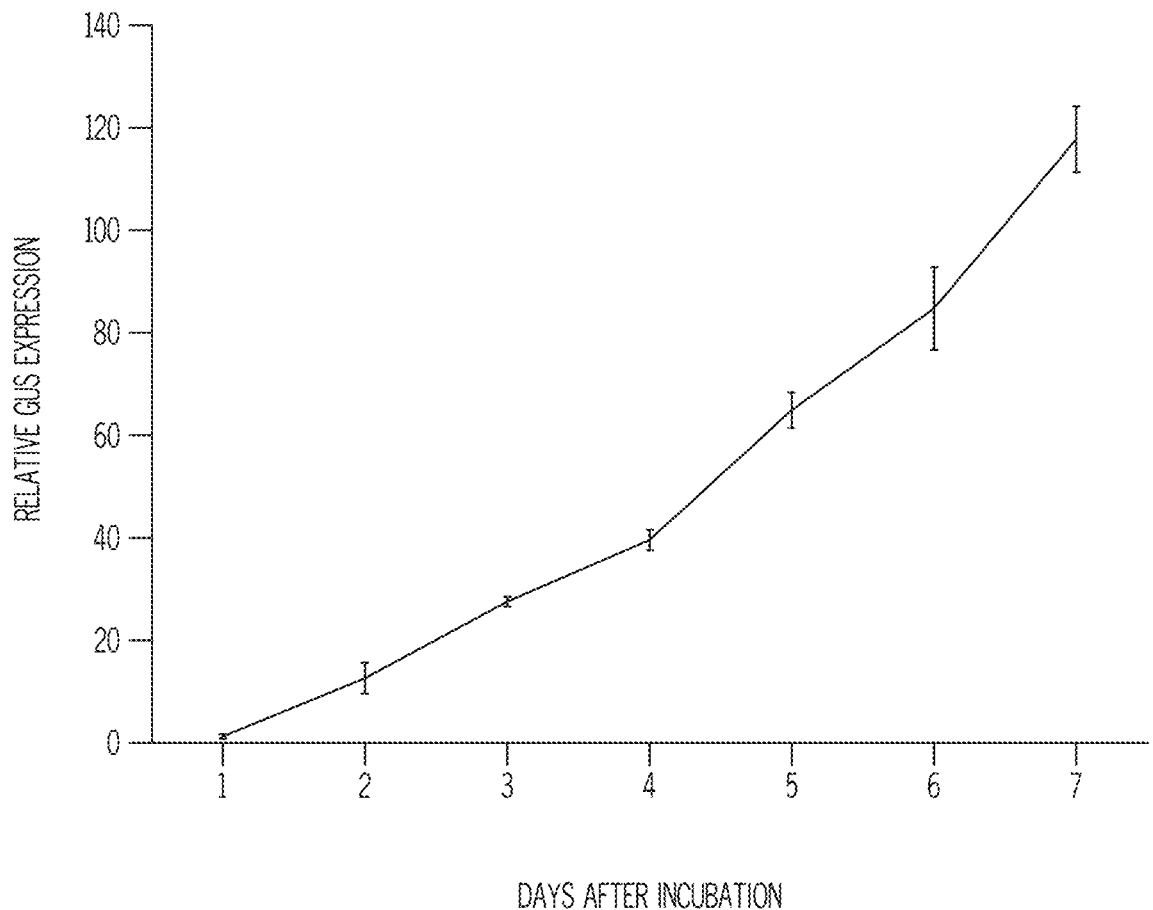
Figure 9H:
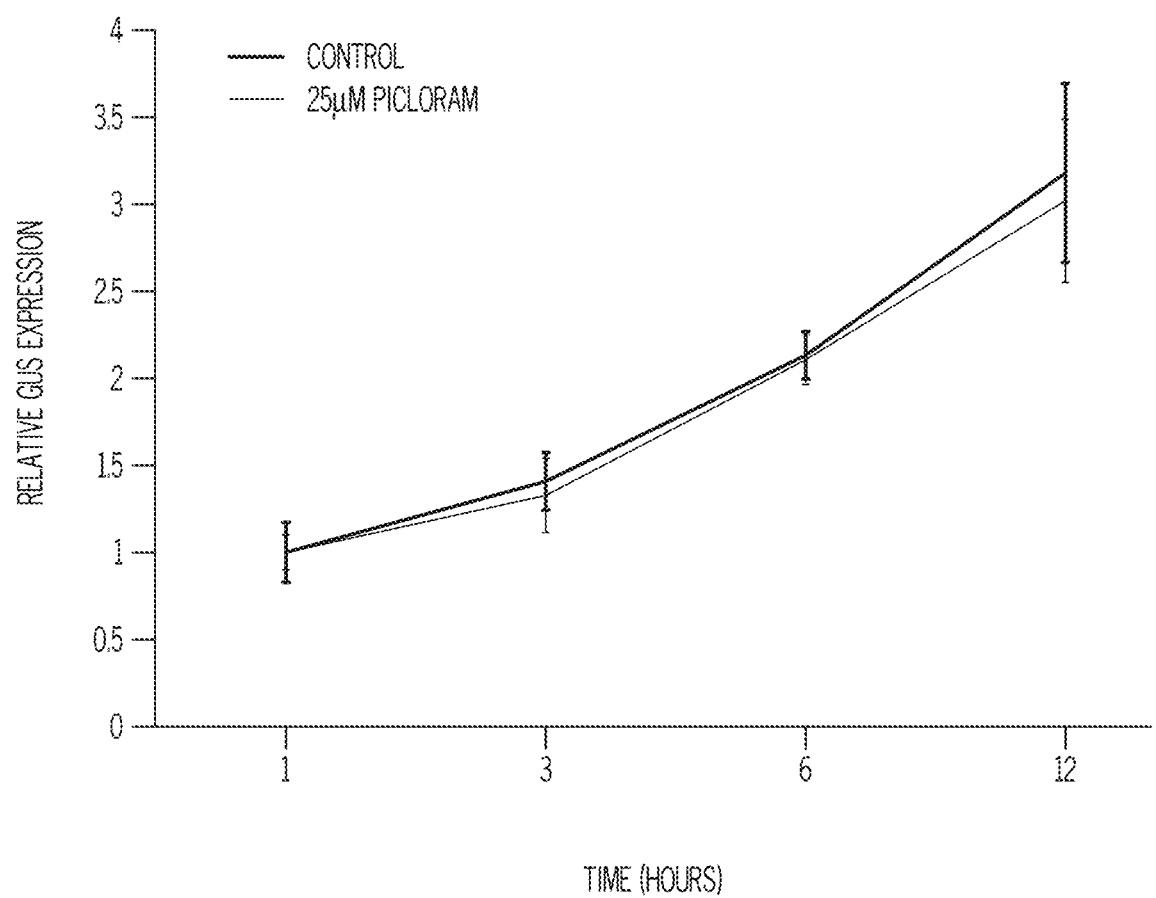
Figure 9I:
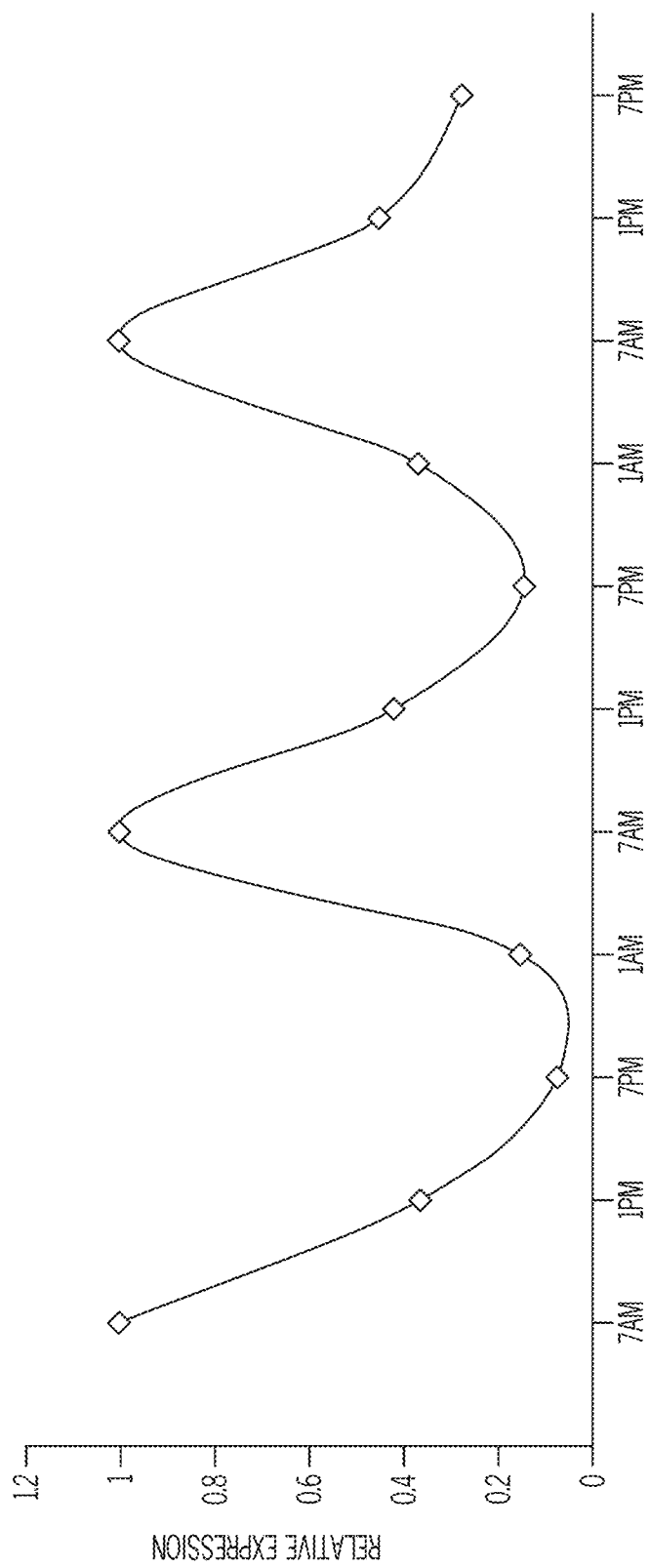

FIGS. 9A, 9B, 9C, 9D, 9E, 9F, 9G, 9H, and 9I show that PIC30 expression is developmentally regulated. FIG. 9A shows tissue specific expression of PIC30. qRT-PCR was performed with PIC30 specific primers. Relative expression was normalized to the expression of PIC30 in cauline leaves. The expression of PIC30$_{pro}$::PIC30-GUS in 4 day-old (FIG. 9B), 8 day-old (FIG. 9C) seedlings and in different tissues of 4 week-old plants (FIGS. 9D-F) are also shown. Seedlings and tissue samples were stained in phosphate buffer containing X-gluc at 37° C. for 12 hours. FIG. 9G shows that the expression of PIC30 increases with the age of the plant. Seeds were plated on nutrient media and incubated at 21° C. Samples were collected for seven consecutive days at 24 hour intervals and the expression of PIC30-GUS was analyzed by quantitative MUG assay. The fold increase in reference to 32 days was calculated. Each data point represents the mean of three independent replicates and the bar shows SD. FIG. 9H shows that picloram does not affect the expression of PIC30. 5 day old PIC30$_{pro}$::PIC30-GUS seedlings were either mock treated or treated with 25 pM picloram for indicated time intervals. The MUG assay was then performed. Each data point represents the mean of three independent replicates. The bar shows SD. FIG. 9I shows that the expression of PIC30 is diurnally regulated with high expression during dawn compared to dusk. Seedlings were grown in a 12 hour light/12 hour dark regime at 21° C. Seedlings were collected at designated time periods and frozen immediately. PIC30 expression was analyzed through qRT-PCR and relative expression was normalized to 7 AM sample for each day.

Figure 10:
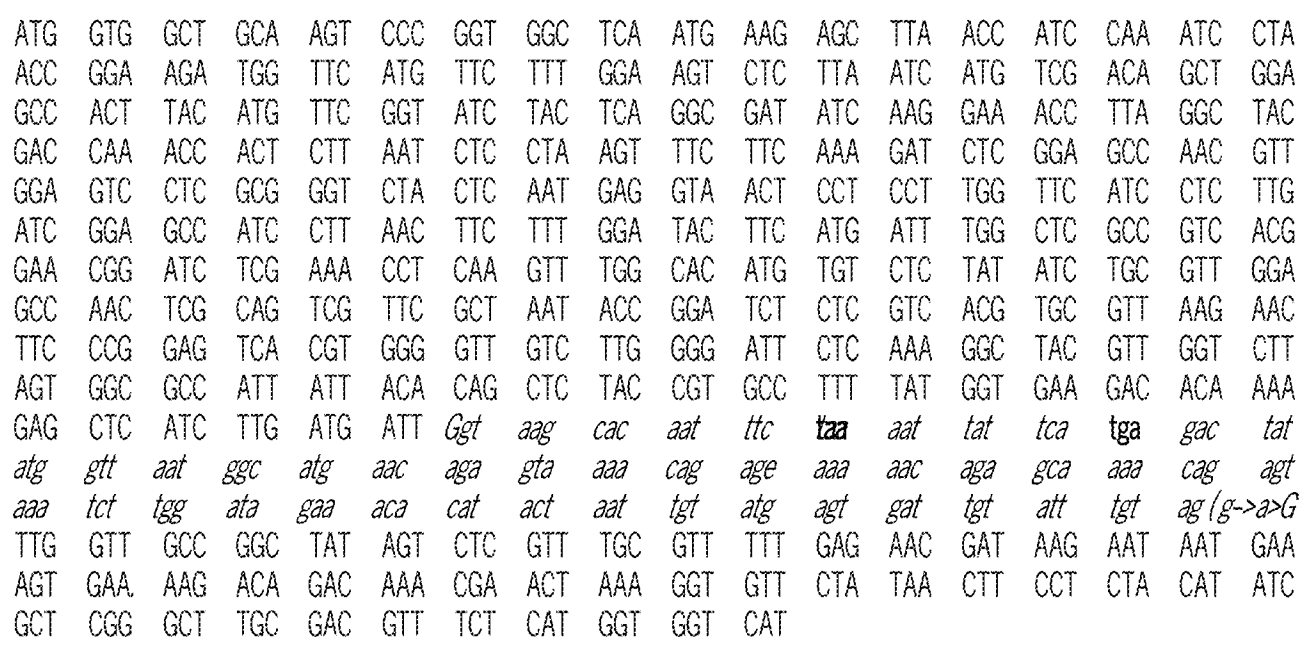

FIG. 10 shows the nucleotide sequence of the pic 30-3 mutant (SEQ ID NO: 3). Two stop codons in the intron are in-frame with a translation start codon in the pic30-3 mutant transcript. The upper case letters correspond to exon sequences. The lower case letters are intron sequences. The bold triplets are two stop codons which are in-frame with the first ATG of the translation start site. Within the intron sequence, g→a reflects the mutation in pic30-3.

Figure 11:
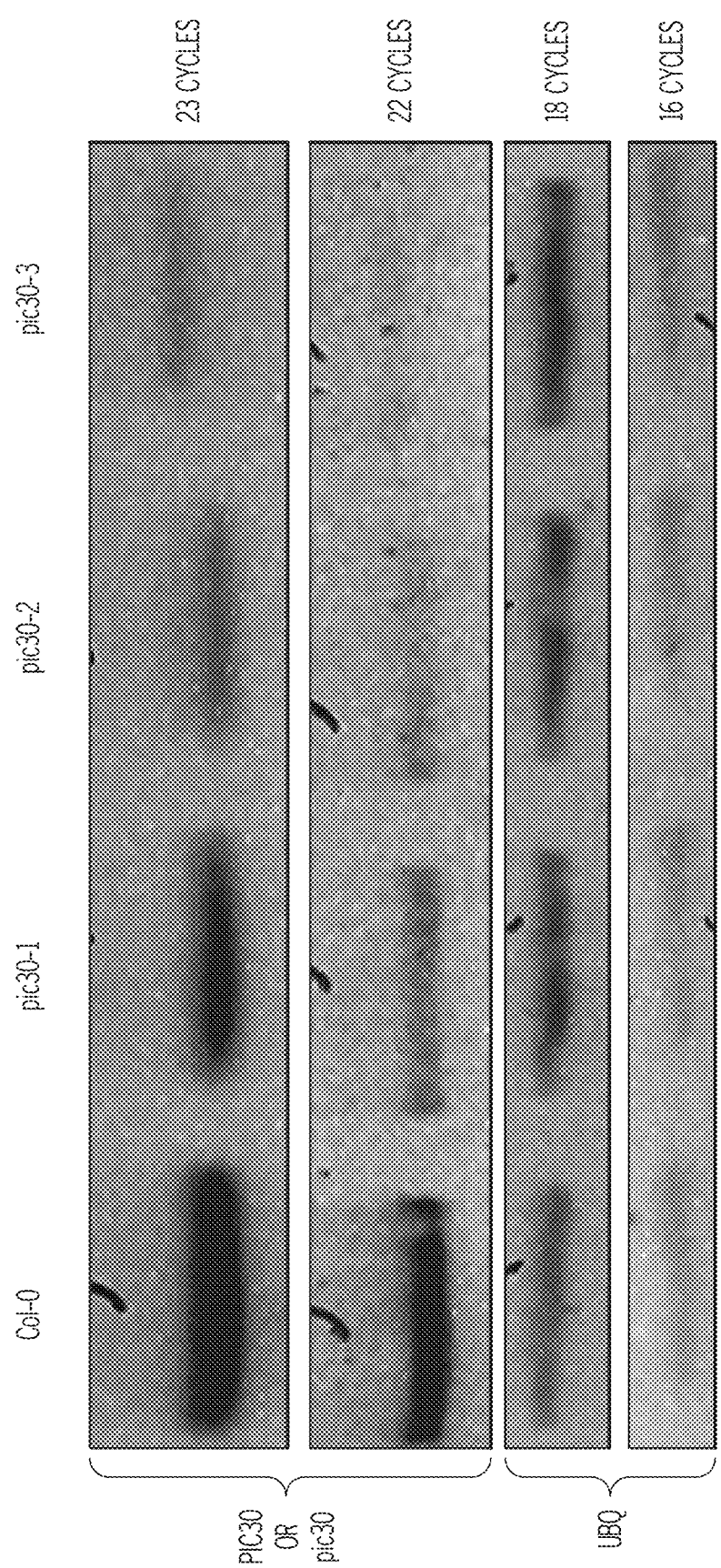

FIG. 11 is an agarose gel showing that an abundance of pic30 mutant transcripts is relatively lower than that of PIC30 in wild type. Total RNA was isolated from 7 day old seedlings and cDNA was synthesized after DNase treatment. cDNA was normalized using ubiquitin (UBQ) as a reference and RT-PCR was performed with PIC30 specific primers.

Figure 12:
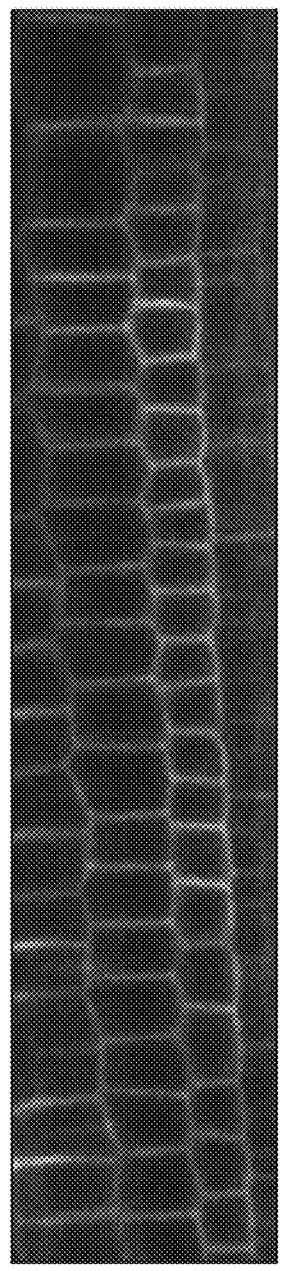
Figure 12:
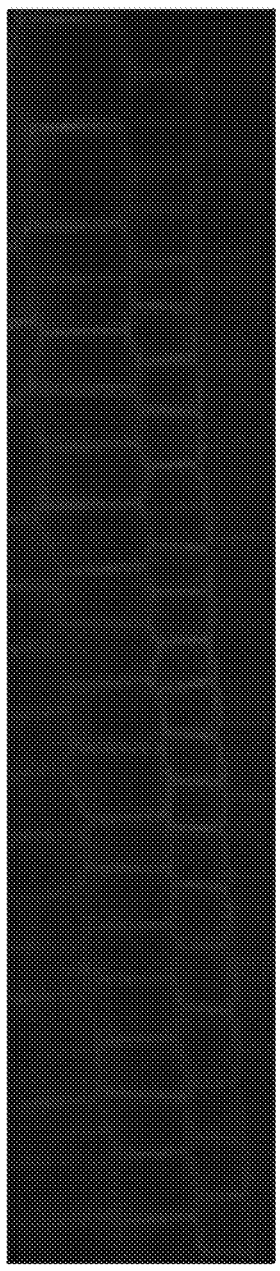
Figure 12:
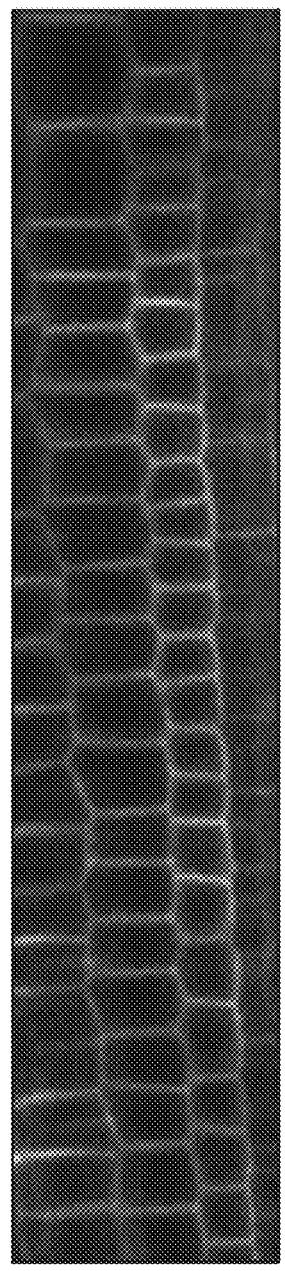
Figure 12:
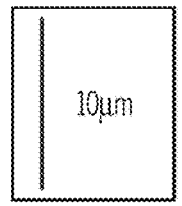

FIG. 12 are images showing that PIC30-GFP co-localizes with the plasma membrane marker PM-RK (CD3-1007). Green fluorescence of PIC30-GFP and red fluorescence of plasma membrane marker PM-RK were superimposed to produce merged image. Five day old transgenic seedlings expressing PIC30-GFP and PM-RK were imaged using laser scanning confocal microscope.

Figure 13A:
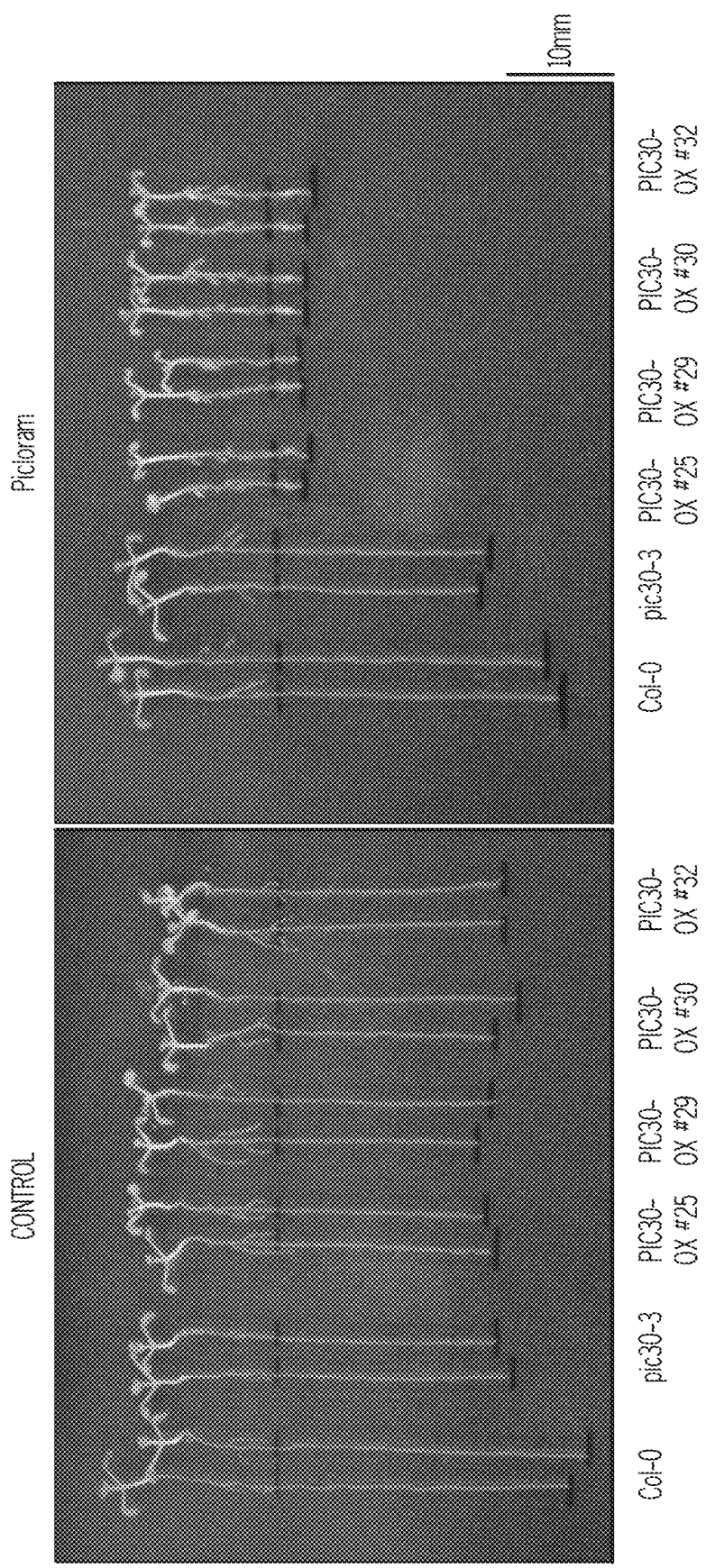
Figure 13B:
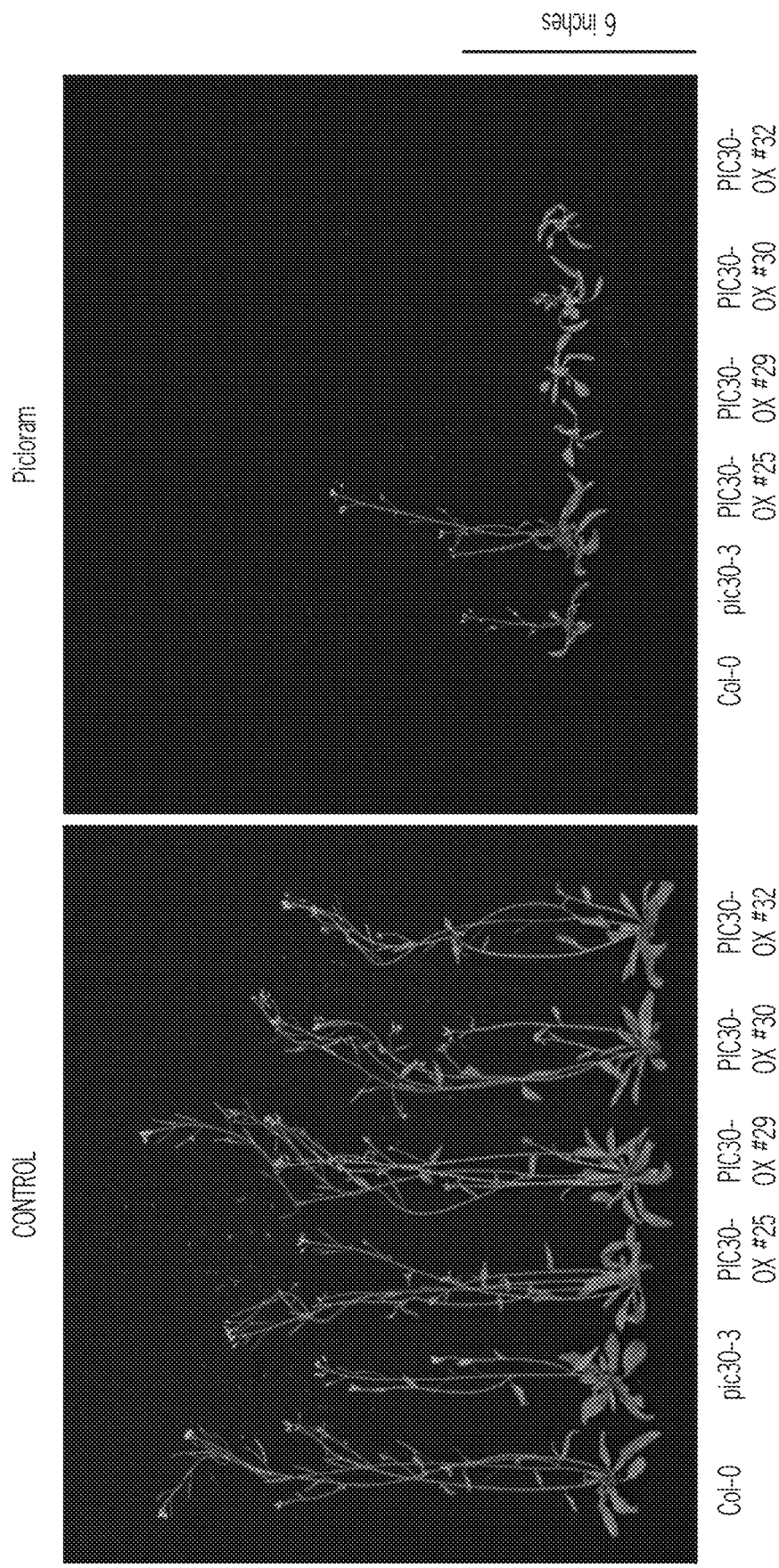
Figure 13C:
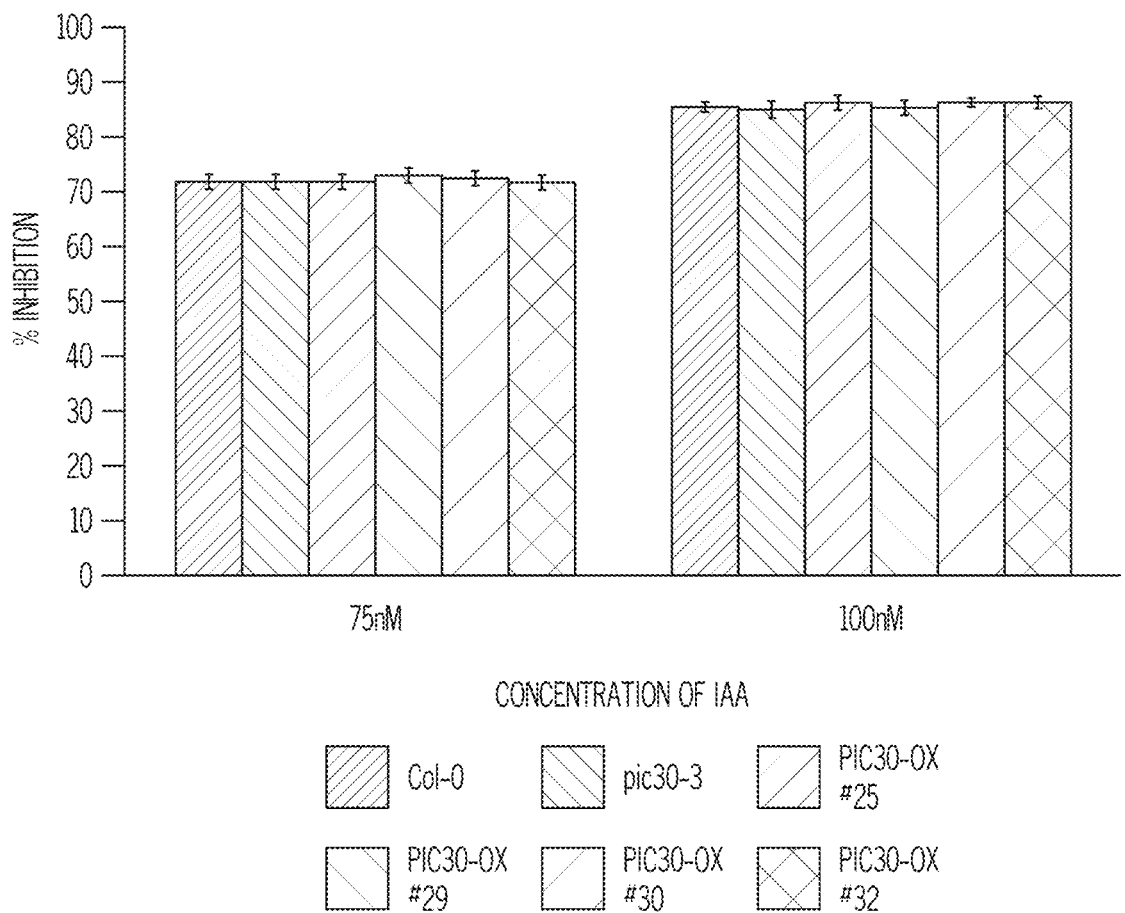
Figure 13D:
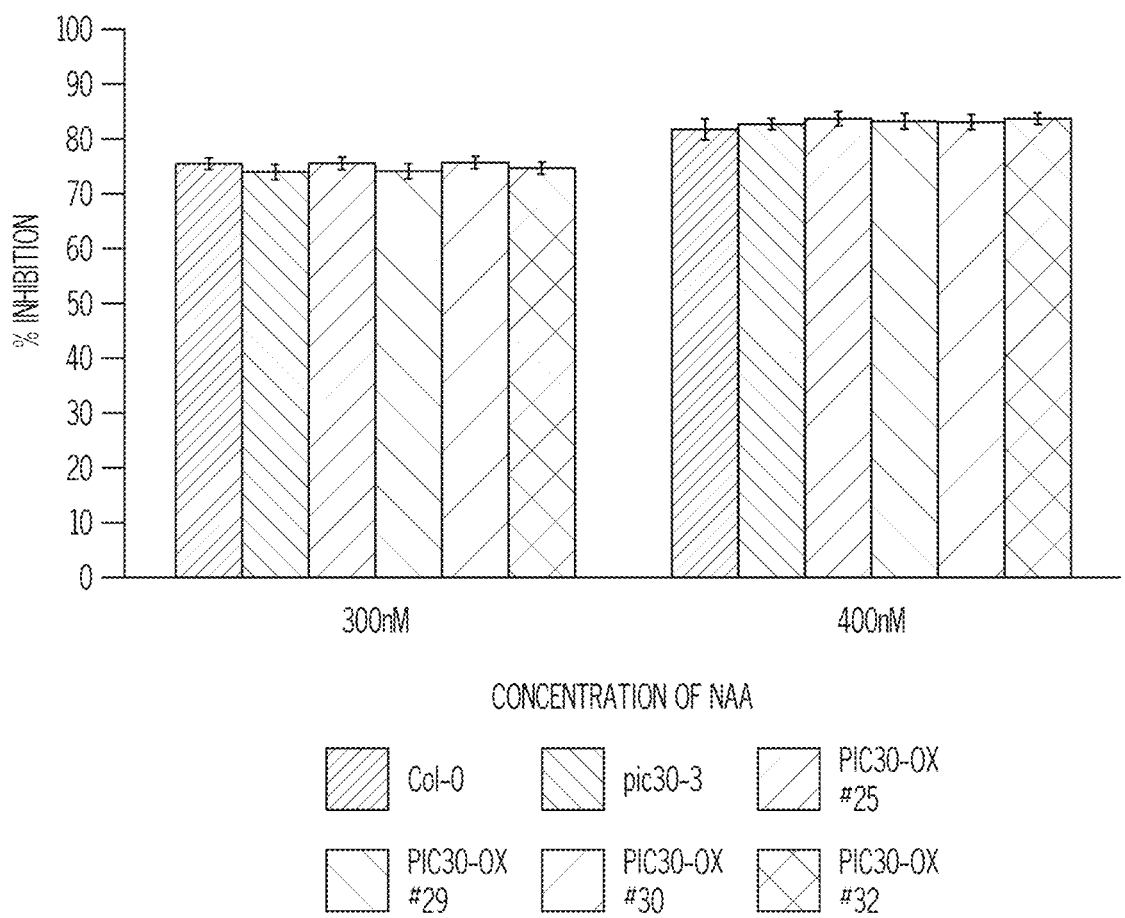

FIGS. 13A, 13B, 13C, and 13D show that PIC30-OX lines are hypersensitive to picloram. FIG. 13A shows that root growths of PIC30-OX lines are hypersensitive to picloram. Four day old seedlings were transferred to either ATS media (for mock treatment) or ATS with 100 nM picloram. After 4 days of incubation, primary root length was measured and images were acquired with representative seedlings. FIG. 13B shows that PIC30-OX lines are hypersensitive to foliar treatment of picloram. For foliar picloram application, approximately 3 week old plants were homogenously sprayed with 100 g/ha of picloram. Images were acquired 14 days after the treatment. PIC30-OX lines show wild-type sensitivity to IAA (FIG. 13C) and 1-NAA (FIG. 13D). Four day old seedlings were transferred to either ATS media (for mock treatment) or ATS with indicated concentrations of IAA and 1-NAA. Root lengths were measured four days after incubation. Each data point represents the MPI, and bars represent SPE.

Figure 14A:
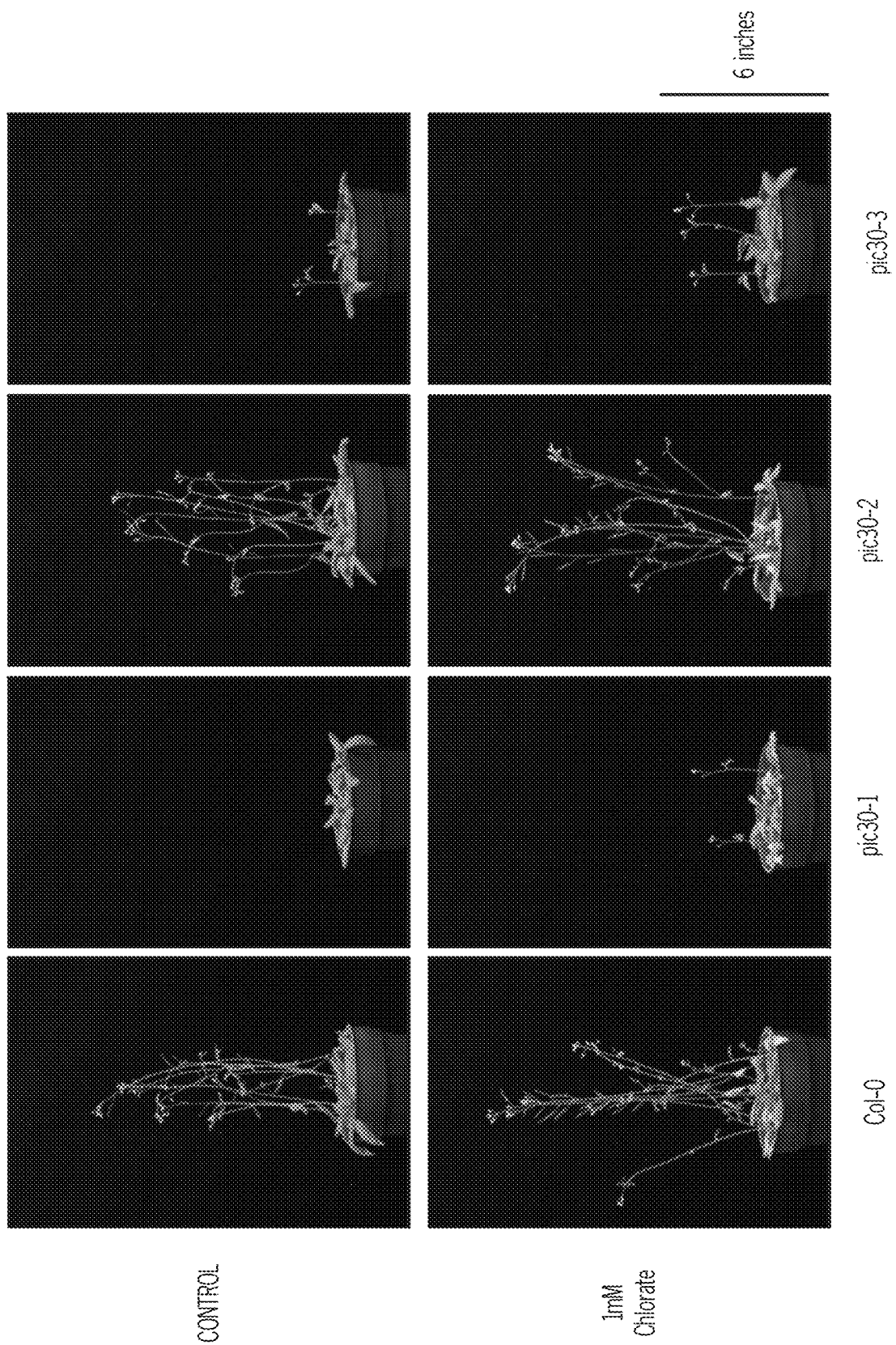
Figure 14B:
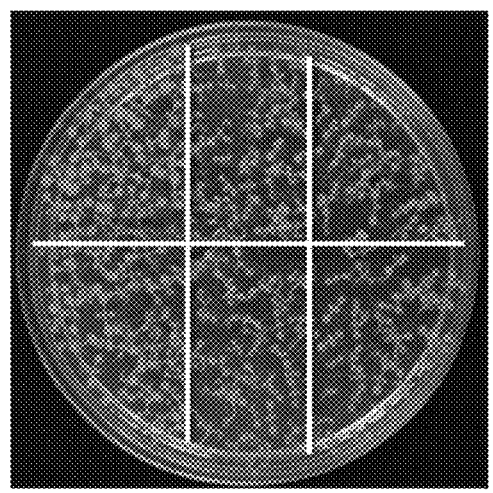
Figure 14B:
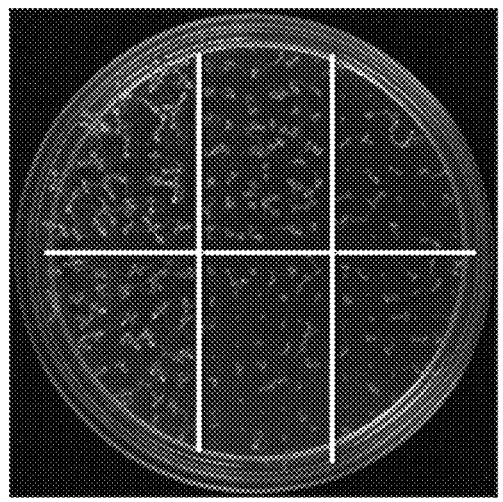
Figure 14B:
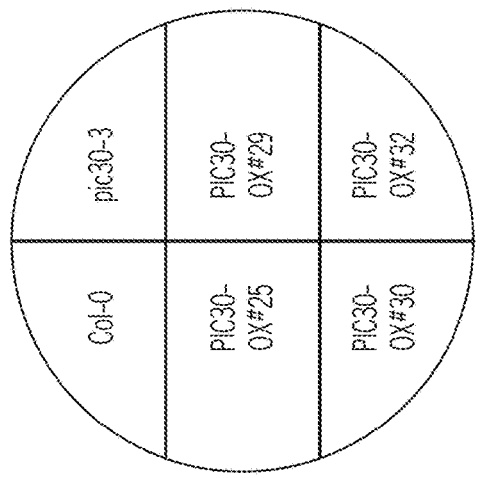
Figure 14B:
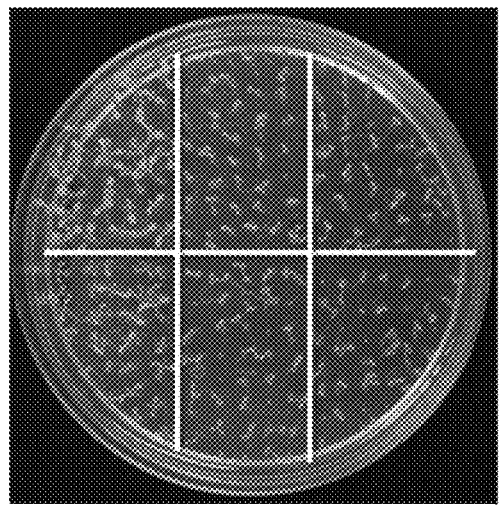
Figure 14C:
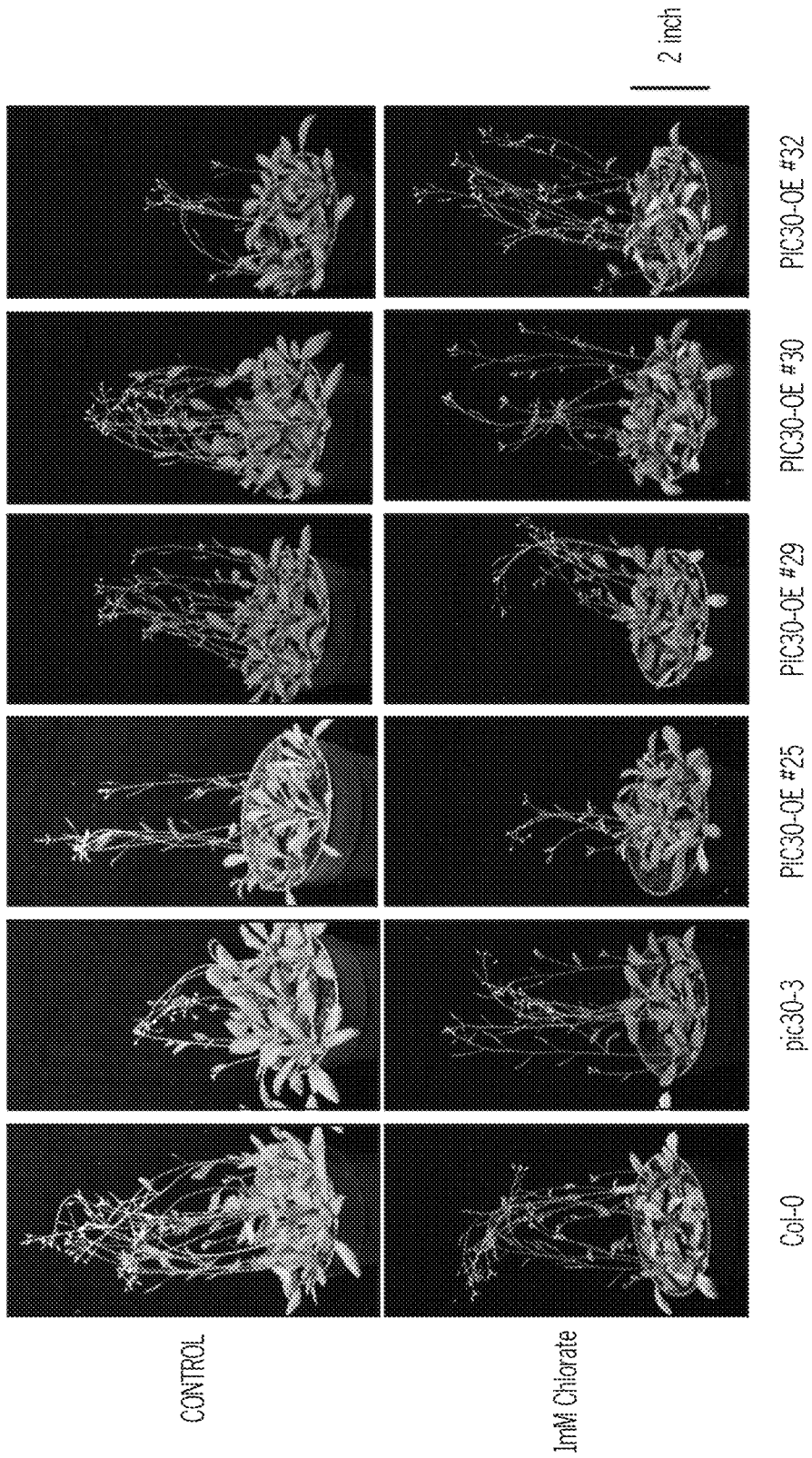

FIGS. 14A, 14B, and 14C show that pic30-3 is insensitive to chlorate ions. FIG. 14A shows that pic30-3 but not pic30-1 or pic30-2 plants are insensitive to chlorate induced necrosis and leaf bleaching. Overexpression of PIC30 in pic30-3 complements chlorate sensitivity at both seedling (FIG. 14B) and adult stages (FIG. 14C). For chlorate sensitivity assay during seedling stage, seeds were plated on either ATS (control) media or ATS media containing indicated concentration of sodium chlorate and subsequently incubated for 9 days. For chlorate sensitivity test of adult plants, 7 day old seedlings were transferred to soil and grown in pots under continuous light for 12 days. Plants were irrigated with 1 mM sodium chlorate on every alternative day. Images were acquired 12 days after first sodium chlorate treatment.

DETAILED DESCRIPTION

It is to be understood that both the foregoing general description and the following detailed description are illustrative and explanatory, and are not restrictive of the subject matter, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that include more than one unit unless specifically stated otherwise.

The section headings used herein are for organizational purposes and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

The plant hormone auxin essentially regulates all aspects of plant growth and development, including root and shoot growth, organ patterning and flower development. While an optimal concentration of auxin stimulates growth and development, hyper-accumulation of auxin promotes abnormal metabolic activities leading to the plant death. Based on this property, several synthetic auxinic chemicals, including 2,4-D (2,4-dichlorophenoxyacetic acid), dicamba and picloram, have been developed as herbicides.

Auxinic chemicals specifically act against a broad range of dicots. As a result, their use is limited to eradicating broad leaf weeds from monocot crops. One of many ways in which this problem can be solved is to create herbicide resistant crop varieties. However, current knowledge on the mechanism of herbicide transport and its subsequent signaling mechanism is very limited.

Among the synthetic auxinic herbicides presently in use, details of the molecular mechanisms of action and transporter proteins responsible for the cellular influx and efflux are known only for 2,4-D. Although some of the genes involved in picloram response have been described previously, none of the proteins involved in the transport of picloram have been characterized so far. Therefore, identifying the genes involved in picloram transport and signaling may help to understand the genetic basis of herbicide action and lead to the generation of genetically modified plants or seeds that are resistant to herbicides.

Similar to auxin, nitrogen is also essential for plant growth and survival. Plants uptake nitrogen either as ammonia or nitrate ions. In addition to serving as a nutritional source, nitrate ions also behave as signaling molecules. Several low and high-affinity nitrate transporter proteins facilitate the flow of environmental nitrate into the plant. Within the plant, a set of specific nitrate influx and efflux transporters mediates the transport of nitrate to the target organs and tissues.

Nitrate metabolism is an energy consuming process, and expression of most of the genes coding for nitrate transporters and nitrate assimilating enzymes are diurnally regulated, showing elevated expression during daytime compared to night. Nevertheless, it has been shown that NRT1.7, which is involved in nitrate mobilization from source-to-sink, behaves in an entirely opposite manner where NRT1.7 expression increases at night compared to day.

A majority of the plant nitrate transporters identified so far are members of the major facilitator superfamily (MFS). This is one of the largest families of membrane transporter proteins found in almost all types of organisms. Most members of this family contain 12 transmembrane domains and are localized to either the plasma membrane or organelle membranes.

During the last decade, extensive research has been done to understand the cellular functions of MFS proteins, and their physiological implications. In *Arabidopsis*, members of this superfamily have been implicated in transport of a wide variety of substrates, including hormones, nutrients and various heavy metal ions. Because of their abilities to transport many different classes of substrates, they are considered to be important players in plant growth and development.

Despite the extensive knowledge on MFS transporters, the individual functions of most members of the MFS have yet to be determined. Furthermore, a need exists for the development of crops that are resistant to herbicides and environmental stress, such as drought. Embodiments of the present disclosure address this need by at least expanding on the discovery that pic30 encodes a major facilitator transporter protein involved in picloram transport.

In some embodiments, the present disclosure pertains to a modified plant or seed that includes a mutated gene. The mutated gene includes, without limitation, a pic30 mutant, a mutant homolog of pic30, and combinations thereof. The modified plant or seed is resistant to at least one herbicide, such as a picolinate herbicide. In some embodiments, the modified plant or seed is resistant to more than one herbicide. In some embodiments, the modified plant or seed is also resistant to one or more sources of environmental stress.

In additional embodiments, the present disclosure pertains to methods of developing a modified plant or seed that is resistant to at least one herbicide. In some embodiments illustrated in FIG. 1A, the method includes a step of introducing at least one of a pic30 mutant or a mutant homolog of pic30 to the plant or seed. The introduction of the at least one mutated gene results in the formation of the modified plant or seed (step 12) and the development of resistance to herbicides (step 14). In some embodiments, the introduction of the mutant gene also results in the development of resistance to one or more sources of environmental stress (step 16).

As set forth in more detail herein, the present disclosure can have various embodiments. In particular, various methods may be utilized to introduce various types of mutated pic30 genes and their homologs into various plants and seeds in order to form various types of modified plants and seeds that have resistance to various herbicides and sources of environmental stress.

Plants and Seeds

The present disclosure can be utilized to introduce mutated genes into various types of plants and seeds and thereby form various types of modified plants and seeds. For instance, in some embodiments, the modified plant or seed is a dicot. In some embodiments, the dicot includes, without limitation, soybean, lettuce, tomato, potato, legumes, cotton, and combinations thereof. In some embodiments, the modified plant is a dicot crop, such as tomato. In some embodiments, the modified seed is a dicot seed, such as a tomato seed.

In some embodiments, the modified plant or seed is a legume. In some embodiments, the legume includes, without limitation, peas, beans, lentils, peanuts, and combinations thereof.

In some embodiments, the plant or seed is a monocot. In some embodiments, the monocot includes, without limitation, wheat, corn, rice, millet, maize, sorghum, barley, sweetcorn, oats, and combinations thereof.

In some embodiments, the modified plants of the present disclosure can be utilized to generate the modified seeds of the present disclosure. As such, in some embodiments, the modified seeds of the present disclosure are derived from the modified plants of the present disclosure. Additional plants and seeds not listed here can also fall within the scope of the present disclosure.

Mutated Genes

The modified plants and seeds of the present disclosure may include various types of pic30 mutants and mutant homologs of pic30. Furthermore, the mutated genes may be in various forms.

For instance, in some embodiments, the mutated gene is in the form of an endogenous gene. In some embodiments, the mutated gene is in the form of a transgene. In some embodiments, the mutated gene is in the form of an over-expressed gene. In some embodiments, the mutated gene is in the form of an under-expressed gene (e.g., a knock-down gene or a knockout gene).

The pic30 mutants and mutant homologs of pic30 may also have various types of mutations. For instance, in some embodiments, the mutation includes, without limitation, a point mutation, a missense mutation, a non-sense mutation, a frame shift mutation, a null mutation, a splice site mutation, and combinations thereof. In some embodiments, the mutation includes a point mutation. In some embodiments, the mutation includes, without limitation, a dominant mutation, a semi-dominant mutation, a homozygous mutation, a heterozygous mutation, and combinations thereof.

The pic30 mutants and mutant homologs of pic30 may have mutations in various gene regions. For instance, in some embodiments, the mutated gene includes a mutation in a nodulin-like (NOD) domain of the gene. In some embodiments, the mutated gene includes a mutation in a major facilitator (MFS) domain of the gene. Mutations in other gene regions can also be envisioned.

In some embodiments, the mutated gene is pic 30-1 (i.e., SEQ ID NO: 1). As illustrated in FIGS. 2A-C, pic 30-1 contains a missense mutation in the nodulin-like (NOD) domain of pic 30 (i.e., a $C^{392}T$ change in its first exon) that results in a change in a single amino acid of the gene product (i.e., SEQ ID NO: 4).

In some embodiments, the mutated gene is pic 30-2 (i.e., SEQ ID NO: 2). As illustrated in FIGS. 2A-C, pic 30-2 contains a non-sense mutation in the major facilitator (MFS) domain of pic 30 (i.e., a $G^{1501}A$ change in its second exon) that results in a premature stop codon and the formation of a truncated gene product (i.e., SEQ ID NO: 5).

In some embodiments, the mutated gene is pic 30-3 (i.e., SEQ ID NO: 3). As illustrated in FIGS. 2A-C, pic 30-3 contains a $G^{698}A$ change in its intron, altering the conserved G within the 3" splice site consensus sequence and thereby expressing the intron (i.e., SEQ ID NO: 6).

Introduction of Mutated Genes into Plants or Seeds

Various methods may be utilized to introduce pic30 mutants and mutant homologs of pic30 into plants or seeds. For instance, in some embodiments, the mutated gene is introduced by introducing a mutated transgene into the plant or seed. In some embodiments, the transgenic introduction occurs by a method that includes, without limitation, transferred DNA insertion, enhancer trap insertion, floral-dip transformation, tissue transformation, callus transformation, mobile genetic elements insertion, activation tagging insertion, fox hunting insertion, particle bombardment, and combinations thereof.

In some embodiments, the mutated gene is introduced into a plant or seed by floral-dip transformation. In some embodiments, the floral-dip transformation includes positioning the mutated gene in a recombinant vector, placing the recombinant vector in bacterial cells (e.g., *Agrobacterium tumefaciens*), and transforming the bacterial cells into the plant or seed.

In some embodiments, the mutated gene is introduced into a plant or seed by tissue or callus transformation. In some embodiments, the tissue or callus transformation occurs by utilizing bacterial cells (e.g., *Agrobacterium*).

In some embodiments, the mutated gene is introduced into the plant or seed by mutating an endogenous gene in the plant or seed. In some embodiments, the endogenous gene mutation occurs by methods that include, without limitation, chemical mutation, site directed mutagenesis, irradiation, and combinations thereof. In some embodiments, the mutation is introduced by the site-directed mutagenesis of the endogenous gene. In some embodiments, the mutation is introduced by a chemical mutation of the endogenous gene. In some embodiments, the chemical mutation includes exposure of the endogenous gene to a chemical. In some embodiments, the chemical includes, without limitation, ethyl methane sulfonate (EMS), aminopurine, nitrosoguanidine, bisulfite, and combinations thereof.

In some embodiments, the endogenous gene is mutated in the plant or seed by site directed mutagenesis. In some embodiments, the endogenous gene is mutated in the plant or seed by the utilization of Crispr/Cas9 techniques.

Mutated genes can be introduced into plants or seeds at various stages of the plant's or seed's development. For instance, in some embodiments, the mutated gene is introduced at a seedling stage of a plant. In some embodiments, the mutated gene is introduced at an adult stage of a plant.

Resistance to Herbicides

The modified plants and seeds of the present disclosure can have resistance to various types of herbicides. For instance, in some embodiments, the herbicide includes one or more picolinate herbicides. Picolinate herbicides generally refer to herbicides that contain pyridine-2-carboxylates. In some embodiments, the picolinate herbicide includes, without limitation, aminocyclopyrachlor, aminopyralid, clopyralid, tryclopyr, picloram, arylpicolinates (e.g., Arylex™ and Rinskor™), and combinations thereof. In some embodiments, the picolinate herbicide includes picloram. In some embodiments, the picolinate herbicide includes aminopyralid.

In some embodiments, the herbicide includes one or more herbicides that inhibit photosynthetic electron transport. Examples of such herbicides include, without limitation, paraquat, 3-(3,4-dichlorophenyl)-1,1-dimethylurea (DCMU), and combinations thereof.

In some embodiments, the herbicide includes one or more acetolactate synthase (ALS) inhibitors. Examples of ALS inhibitors include, without limitation, propoxycarbazone-sodium, bensulfuron-methyl, chlorimuron-ethyl, chlorsulfuron, foramsulfuron, halosulfuron-methyl, mesosulfuron-methyl, metsulfuron-methyl, nicosulfuron, primisulfuron-methyl, prosulfuron, rimsulfuron, sulfometuron-methyl, sulfosulfuron, thifensulfuron-methyl, triasulfuron, tribenuron-methyl, trifloxysulfuron-sodium, triflusulfuron-methyl, cloransulam-methyl, cloransulam-methyl, diclosulam, florasulam, flumetsulam, penoxsulam, pyroxsulam, and combinations thereof.

In some embodiments, the herbicide includes one or more broad-spectrum herbicides, such as dicamba. In some embodiments, the herbicide includes auxinic herbicides. In some embodiments, the auxinic herbicides include, without limitation, 2,4-dichlorophenoxyacetic acid (2,4-D), dicamba, picloram, and combinations thereof.

In some embodiments, the modified plants and seeds of the present disclosure are resistant to at least one herbicide when compared to a corresponding wild-type plant or seed. In some embodiments, the modified plants and seeds of the present disclosure are substantially resistant towards one or more herbicides. In some embodiments, the modified plants and seeds of the present disclosure are partially resistant towards one or more herbicides. In some embodiments, the modified plants and seeds of the present disclosure are selectively resistant towards one or more herbicides.

In some embodiments, the modified plants and seeds of the present disclosure are selectively resistant towards one or more picolinate herbicides. In some embodiments, the modified plants and seeds of the present disclosure are selectively resistant towards one or more picolinate herbicides but non-resistant towards other types of herbicides. In some embodiments, the modified plants and seeds of the present disclosure are selectively resistant towards picloram but non-resistant towards indole-3-acetic acid (IAA), 2,4-D and (1-Naphthaleneacetic acid 1-NAA).

In some embodiments, the root growth inhibition of the modified plants and seeds of the present disclosure by one or more herbicides is less than about 50% in root length. In some embodiments, the root growth inhibition of the modified plants and seeds of the present disclosure by one or more herbicides is less than about 40% in root length. In some embodiments, the root growth inhibition of the modified plants and seeds of the present disclosure by one or more herbicides is less than about 30% in root length. In some embodiments, the root growth inhibition of the modified plants and seeds of the present disclosure by one or more herbicides is less than about 20% in root length. In some embodiments, the root growth inhibition of the modified plants and seeds of the present disclosure by one or more herbicides is less than about 15% in root length. In some embodiments, the root growth inhibition of the modified plants and seeds of the present disclosure by one or more herbicides is less than about 15% in root length.

In some embodiments, the size of the modified plants of the present disclosure (e.g., as defined by height, leaf size, dry weight and combinations thereof) that have been exposed to one or more herbicides may be about the same size as the modified plants that have not been exposed to the one or more herbicides. In some embodiments, the size of the modified plants of the present disclosure that have been exposed to one or more herbicides may be at least about 90% of the size (e.g., in height) of the modified plants that have not been exposed to the one or more herbicides. In some embodiments, the size of the modified plants of the present disclosure that have been exposed to one or more herbicides may be at least about 75% of the size (e.g., in height) of the modified plants that have not been exposed to the one or more herbicides. In some embodiments, the size of the modified plants of the present disclosure that have been exposed to one or more herbicides may be at least about 50% of the size (e.g., in height) of the modified plants that have not been exposed to the one or more herbicides.

Without being bound by theory, it is envisioned that the modified plants and seeds of the present disclosure become resistant to one or more herbicides as a result of the expression of the one or more mutated genes of the present disclosure in the plants and seeds. In particular, it is envisioned that the products of the one or more mutated genes confer resistance to one or more herbicides by hampering the transport of the one or more herbicides into the plants and seeds.

For instance, as set forth in more detail in Example 1, Applicants have discovered that pic30 encodes a major facilitator transporter protein that is involved in picloram transport. As also set forth in more detail in Example 1, Applicants have discovered that proteins expressed by pic30 mutants hamper the transport of picloram into plant cells.

Resistance to Environmental Stress

In some embodiments, the modified plants and seeds of the present disclosure may also be resistant to one or more sources of environmental stress. In some embodiments, the one or more sources of environmental stress include, without limitation, drought, high temperature, UV radiation, microbial contamination (e.g., bacterial contamination), plant pathogenesis, biotic stress, abiotic stress, and combinations thereof.

Without being bound by theory, it is envisioned that the modified plants and seeds of the present disclosure also become resistant to one or more sources of environmental stress (e.g., both biotic stress and abiotic stress) as a result of the expression of the one or more mutated genes of the present disclosure in the plants and seeds. In particular, it is envisioned that the products of the one or more mutated genes confer resistance to one or more sources of environmental stress by hampering the transport of one or more chemicals that are associated with environmental stress (e.g., abscisic acid or salicylic acid).

Applications and Advantages

The present disclosure can provide various advantages. For instance, in some embodiments, the modified plants and seeds of the present disclosure demonstrate resistance to herbicides without demonstrating any adverse growth defects. Furthermore, the modified plants and seeds of the present disclosure can also show resistance to various sources of environmental stress, such as drought. Moreover, various methods of the present disclosure can be utilized to generate the modified plants and seeds of the present disclosure in a facile and cost-effective manner.

As such, the present disclosure can find numerous applications. For instance, in some embodiments, the modified plants and seeds of the present disclosure can be utilized to control the growth of weeds in a field. In some embodiments, such methods include applying at least one herbicide to a field that contains a modified plant or seed of the present disclosure that is resistant to the herbicide. In some embodiments, the modified plant or seed may also show resistance to environmental stress.

In some embodiments, the weed growth control methods of the present disclosure also include a step of applying the modified plants or seeds of the present disclosure to the field. In some embodiments, the applying of the modified plants or seeds to the field occurs before, during or after applying the herbicide to the field.

In some embodiments, the weed growth control methods of the present disclosure also include a step of growing a modified plant in the field. In some embodiments, the growing occurs before, during or after applying the herbicide to the field. In some embodiments, the growing occurs by growing the modified plant from a modified seed of the present disclosure.

In more specific embodiments illustrated in FIG. 1B, the weed growth control methods of the present disclosure include growing a modified plant of the present disclosure in a field (step 20) and applying at least one herbicide to the field (step 22) such that the modified plant shows resistance to the at least one herbicide (step 24). In some embodiments, the modified plant may also show resistance to environmental stress (e.g., abiotic stress and biotic stress) (step 26).

Furthermore, the modified plants and seeds of the present disclosure can be utilized to expand the use of many herbicides, such as picolinate herbicides (e.g., picloram) that act non-specifically against a broad range of plants or seeds (e.g., dicots). The aforementioned advantages address an unmet need because, while several herbicide resistant plants or seeds have been generated, no plants or seeds have been generated that are resistant to auxinic herbicides.

Furthermore, although some possible genetic modifications have been reported for 2,4-D resistance, and although the possibility of using several other genes for developing picloram resistance has been suggested (e.g., AFB4, AFB5 and SGT1b for picloram resistance, as indicated in U.S. Pat. No. 7,820,883 B2 to Walsh et al.), these internal targets are unable to prevent picloram or other picolinate herbicides from targeting more than one biochemical or physiological pathway. On the other hand, mutations in pic30 and their homologs can result in a more specific blocking of herbicide transport into modified plants or seeds.

Additional Embodiments

Reference will now be made to more specific embodiments of the present disclosure and experimental results that provide support for such embodiments. However, Applicants note that the disclosure herein is for illustrative purposes only and is not intended to limit the scope of the claimed subject matter in any way.

Example 1. *Arabidopsis* PIC30 Encodes a Major Facilitator Transporter Protein that is Involved in Picloram Transport In this Example, Applicants report the identification and characterization of PIC30, a novel *Arabidopsis* gene that is involved in transport of synthetic auxinic herbicide picloram. PIC30 is a member of major facilitator superfamily (MFS), and is an ortholog of previously characterized anion transporters. The PIC30 protein contains 12 putative transmembrane domains and selectively localizes to the plasma membrane. Results of in planta transport assays demonstrate that PIC30 specifically transports picloram but not indole-3-acetic acid (IAA). Consistent with the role of PIC30 as a picloram and nitrate transporter, three allelic pic30 mutants are selectively insensitive to picolinate herbicides, and pic30-3 mutant is highly insensitive to chlorate (a transport analog of nitrate) ions. Moreover, overexpression of PIC30 fully complements both picloram and chlorate insensitive phenotypes of pic30-3. Applicants have also observed in this Example that the pic30 mutants are semi-dominant.

Example 1.1. Plant Material and Growth Conditions

Wild type and mutant *Arabidopsis* seeds used in this Example were in Col-0 background. Seeds were surface sterilized with 2.4% sodium hypochlorite solution containing 0.01% triton X-100 and then rinsed thoroughly with sterile distilled water before plating onto the nutrient media.

Unless specified, *Arabidopsis thaliana* nutrient media with 1% sucrose (ATS, Lincoln et al. 1990) was used. To study the diurnal regulation of PIC30 gene expression, Col-0 seeds were plated on media and incubated at 21° C. under 12 hour light/12 hour dark cycles. Starting from the $7^{th}$ day, seedling samples were collected at 6-hour time intervals for indicated durations and frozen in liquid nitrogen. cDNA was prepared from total RNA extracted from the seedlings, and qRT-PCR was performed.

To study the effect of picloram on PIC30 expression, 5 day old $PIC30_{pro}$::PIC30-GUS seedlings were treated with 25 pM picloram in liquid media. They were incubated under continuous light at 21° C. without shaking, and samples were collected at different time intervals and frozen in liquid nitrogen. PIC30-GUS expression was determined through quantitative MUG assay.

For root growth inhibition assays, 4-5 day old seedlings were transferred to control media and media containing indicated concentrations of different auxins. Primary root lengths were measured after 4 days of incubation, and percentage root growth inhibition was calculated.

To test auxin induced DR5::GFP expression, 5 day-old seedlings were transferred to control media and media containing indicated concentrations of different auxins. Plates were incubated for 20 hours at 21° C. under continuous light. Confocal images were acquired after the incubation period.

Example 1.2. Construct Preparation and Plant Transformation

To prepare $PIC30_{pro}$::PIC30-GUS transgenic lines, full length PIC30 gene and a 2 kb region upstream of the ATG was amplified from wild type genomic DNA using the primers PIC30-PROMXho1-F: 5'-CACCCTCGAGGCA-GATTTACCGTACAGCAA-3'; and PIC30 BamH1-R: 5'-AATGGATCCCCCTCCTTTTCCTATTACTTTGC-3', using phusion DNA polymerase (NEB). The PCR product was cloned into pBluescript SK cloning vector, and then sub-cloned into the pBI101.1 vector carrying GUS reporter gene at the COOH-terminus. The recombinant vector was shuttled into *Agrobacterium* strain GV3101 and transformed into wild type plants using the floral dip method.

To prepare CaMV $35S_{pro}$::pic30-1-myc (pic30-1-OX) transgenic lines, full length pic30-1 coding region without the intron and stop codon was amplified using primers PIC30 BamH1-F: 5'-CACCG-GATCCCTCTCGACACACACACTT-3' and PIC30Xho1-R: 5'-TCTCGAGCCCTCC TTTTCCTATTACTTTGC-3' using phusion DNA polymerase (NEB). The PCR product was then cloned into modified pBluescript SK vector carrying 9× myc epitope DNA sequence in frame with the final codon from pic30-1. The pic30-1-myc fragment was released and sub-cloned into pROKII vector. The recombinant vector was shuttled into *Agrobacterium* strain GV3101 and transformed into wild type plants.

To prepare CaMV35S$_{pro}$::PIC30-GFP (PIC30-OX) transgenic lines, full length PIC30 gene including the intron was amplified without the stop codon, using the primers PIC30BamH1-F: 5'-CACCG-GATCCCTCTCGACACACACAC TT-3' and PIC30Xho1-R: 5'-TCTCGAGCCCTCC TTTTCCTATTACTTTGC-3'. The amplified gene was directionally cloned into the pENTR/D-TOPO vector (Invitrogen, Calif.) and transferred into the pB7WG2.0 gateway vector using LR clonase kit according to manufacturer's instructions (Invitrogen, Calif.). The recombinant pB7WG2.0 vector containing the PIC30 gene was shuttled into the *Agrobacterium* strain GV3101, and transgenic plants expressing PIC30-GFP were generated in the pic30-3 mutant background.

To prepare PM-RK/35S$_{pro}$::PIC30-GFP lines, PM-RK (CD3-1007) was obtained from *Arabidopsis* Resource center (ABRC, Ohio State University). PM-RK was shuttled into *Agrobacterium* strain GV3101 and transformed into transgenic plants carrying 35S$_{pro}$::PIC30-GFP.

Example 1.3. Qualitative and Quantitative GUS Expression Analysis

For histochemical GUS staining, seedlings or tissues were fixed and stained as described previously (Parry et al., *The Plant Cell* 18, 1590-15603, 2006). After staining, seedlings/tissues were transferred to 70% of ethanol to remove chlorophyll, then imaged using Nikon SMZ 1500 stereo microscope.

Quantification of GUS expression was performed by fluorometric MUG (4-methylumbelliferyl-beta-D-glucuronide) assay following protocol described elsewhere (Parry et al. *The Plant Cell* 18, 1590-15603, 2006) and the fluorescence was measured using a Fluorometer (Modulus, Turner Biosystems).

Example 1.4. Confocal Imaging

Confocal images were acquired using either 20× water immersion or 60× oil immersion lenses with Fluoview™ FV1000 laser scanning confocal microscope (Olympus). While making a quantitative comparison between one or more confocal images, similar laser intensity and transmittance light were used.

Example 1.5. In Planta Chlorate and Picloram Sensitivity Test

For chlorate sensitivity testing at the seedling stage, seeds were plated onto either control media or media containing 1-1.5 mM sodium chlorate. Plates were incubated under continuous light at 21° C. for 9 days. After the incubation, representative images were acquired using DSLR (PENTAX) camera.

For chlorate and picloram sensitivity testing at the adult stage, 7 day-old seedlings were transferred to soil (Fafard growing mix 2) and grown under continuous light for an additional 12 days. To test chlorate sensitivity, plants were then irrigated with 1 mM sodium chlorate solution on alternating days. Chlorate induced leaf bleaching were examined and imaged after 10-12 days. To test picloram sensitivity, plants were sprayed with 200 g/ha of picloram. Images were acquired 14-18 days after the treatment.

Example 1.6. SDS-PAGE and Immunoblotting

Total plant protein was extracted from 7 day-old seedlings in denaturation extraction buffer (125 mM Tris-HCl pH 8.8, 1% SDS, 10% glycerol, 50 mM Na$_2$S$_2$O$_5$), and the protein concentration was determined using Bradford's method. Total protein was separated using 10% SDS-PAGE and transferred to PVDF (Bio-rad, CA) membrane. Immunoblotting was performed using either anti-GFP (Invitrogen, Calif.) or anti-Myc (Covance, N.J.) primary antibody, followed by appropriate secondary antibody. Bands were observed by enhanced chemiluminescence 2 kit (Pierce, Ill.) as per manufacturer's instructions.

Example 1.7. In Planta Radioactive Transport Assay

In planta transport assays were performed according to a protocol described elsewhere (Ito and Gray, *Plant Physiology* 142, 63-74, 2006) with few modifications. 15 mm root sections (at root tip) from 9 day-old seedlings were excised and incubated in transport assay buffer (TAB, 20 mM MES-KOH, pH 5.6, 10 mM sucrose and 0.5 mM CaCl$_2$) for 30 minutes. Root sections were then transferred to the TAB containing 1.5 nM of $^{14}$C picloram and 10 pM of unlabeled picloram or 7.9 nM of $^3$H IAA and incubated for 1-6 hours at room temperature. Following thorough rinsing with cold TAB buffer, root sections were transferred to scintillation vials containing 1 ml of scintillation liquid. Radioactivity was measured using scintillation counter (Beckman Coulter, Calif.).

Example 1.8. Mutation in Pic30 Confers Insensitivity Against Auxinic Herbicide Picloram Approximately 70,000 ethyl methanesulfonate (EMS) mutagenized *Arabidopsis* seeds were screened for insensitivity of primary root growth to 10 pM picloram. Based on this mutant screen, Applicants have identified three independent mutants that were highly insensitive to picloram. All three mutations were mapped to the same genetic window between the gene ID numbers At2g39110 and At2g39260 to a region of 73 kb of the chromosome 2. Sequence analysis of the genes in this genetic window showed that all of them were allelic to the At2g39210 gene coding nucleotide sequence (FIG. 2A) and predicted protein sequence (FIG. 2B). These mutants were subsequently referred to as pic30-1, pic30-2 and pic30-3.

PIC30 is a member of the major facilitator superfamily and in silico protein analysis revealed that it contains a NODULIN-like (NOD) domain and a major facilitator (MFS) domain in its NH$_2$- and COOH- terminals, respectively. Mutations in both pic30-1 and pic30-3 were found to be within the NOD-domain.

The mutation in pic30-1 is a C$^{392}$T change in its first exon (FIG. 2C) resulting in an amino acid change from serine to leucine (S→L). The mutation in pic30-2 is a G$^{1501}$A change in its second exon that introduces a premature stop codon within the MFS domain. The mutation in pic30-3 is a G$^{698}$A change in its intron, altering the conserved G within the 3" splice site consensus sequence (FIG. 2C).

Of the three pic30 allelic mutants, the primary root growth of pic30-3 was slower than that of wild type, pic30-1 and pic30-2 (FIG. 2D). All three mutants were highly insensitive to picloram during seedling and adult stages as assessed by root growth inhibition assays on picloram and response to foliar treatment of picloram, respectively (FIGS. 2D-2E). Moreover, picloram insensitive root growth phenotype in pic30 mutants was inherited as a semi-dominant trait (FIG. 2F).

Example 1.9. The Pic30 Mutants are Selectively Insensitive to Picloram Class of Synthetic Herbicides Since pic30 allelic mutants were isolated in picloram insensitive screening, primary root growth response was tested on incremental doses of picloram. As shown in FIG. 3A, root growth of all three pic30 mutants was found to be highly insensitive to elevated levels of picloram. To test whether these mutants exhibit insensitivity to other auxins, root growth responses were also compared on the natural auxin IAA and the synthetic auxins 2,4-D, 1-NAA and aminopyralid. It was observed that root growth of pic30 mutants were also insensitive to aminopyralid (FIG. 3B) but not to IAA, 2,4-D or 1-NAA (FIGS. 3C-3E).

Since both picloram and aminopyralid belong to the picolinate class of synthetic herbicides, it is possible that mutations in pic30 selectively confer insensitivity against the picolinate class of auxinic herbicides. To gain further insight into picolinate specific insensitivity of pic30 mutant alleles, pic30-3 was crossed with the auxin sensor DR5::GFP. When these seedlings along with DR5::GFP seedlings were treated with different auxins, DR5::GFP expression in pic30-3 was upregulated exclusively by IAA and 2,4-D but not by either picloram or aminopyralid (FIG. 3F), demonstrating picolinate specific insensitivity of the pic30 mutant alleles.

Example 1.10. The Pic30-3 Mutation Disrupts Proper Splicing

As the mutation in pic30-3 disrupts the conserved G in the 3' splice site (FIG. 2C), Applicants hypothesized that the splicing of the pic30 transcript may be defective in pic30-3 mutant. To test this, RT-PCR was performed with PIC30 specific primers using cDNA synthesized from total RNA isolated from wild type and pic30-3 seedlings. Results indicate that the pic30 transcript in pic30-3 does not undergo splicing, resulting in a longer mature transcript compared to that of wild type PIC30 (FIG. 4A). Defective splicing introduces two premature in-frame stop codons in pic30-3.

To gain understanding into the accumulation of mutant transcripts, Applicants performed semiquantitative RT-PCR and quantitative real-time PCR (qRT-PCR) using cDNA synthesized from total RNA isolated from seedlings of three mutant lines and wild type. The data indicate that all three pic30 mutant lines have significantly lower amounts of pic30 transcript, with the lowest in pic30-3 compared to PIC30 transcript in wild type (FIG. 4B). Therefore, due to its resemblance to a genetically null mutant, pic30-3 was selected for most of the mutant characterizations presented here.

Several experimental evidences indicate that mutant transcripts with premature stop codons are subjected to degradation through nonsense-mediated mRNA decay (NMD) (Kurihara et al. 2009). NMD is a conserved surveillance pathway that exists in all eukaryotes and functions in destruction of aberrant mRNA transcripts carrying premature stop codons (Rayson et al. 2012). To test whether the lower abundance of pic30 transcript is due to the regulation by the NMD pathway, Applicants crossed pic30-3 with one of the NMD mutants, upf3-1, and a double homozygous mutant was obtained. The qRT-PCR analysis showed that pic30-3 transcript abundance was approximately four fold in pic30-3xupf3-1 double mutant than in pic30-3 (FIG. 4C).

Example 1.11. PIC30 is Localized to the Plasma Membrane

Members of MFS superfamily predominantly contain 12 transmembrane domains and localize either to the plasma membrane or organelle membranes. Since PIC30 is a member of MFS superfamily, Applicants hypothesized that PIC30 also localizes to either the plasma membrane or one or more organelle membranes. To determine the sub-cellular localization, PIC30 was fused in-frame with green fluorescent protein (GFP) to generate $35S_{pro}$::PIC30-GFP and was stably expressed inpic30-3 (PIC30-OX). Analysis of the co-localization pattern of PIC30-GFP and membrane tracker dye FM4-64 revealed that PIC30-GFP selectively localized to the plasma membrane in the root cells (FIGS. 5A-F). Moreover, plasma membrane marker fused to mCherry protein (PM-RK; CD3-1007) was stably expressed in the PIC30-OX transgenic line. As such, PIC30-GFP was found to be co-localized with PM-RK in root cells.

Example 1.12. Ectopic Expression of PIC30 Complements Picloram Insensitivity of Pic30-3

To determine if the wild type PIC30 gene complements the picloram insensitive root growth phenotype of the pic30-3 mutant, several PIC30-OX transgenic lines expressing PIC30-GFP recombinant protein (FIG. 6A) were obtained. To test for complementation of picloram insensitivity, a root growth inhibition assay was performed on media containing 10 pM picloram. While the primary root growth of wild type was inhibited by approximately 73% compared to 46% in pic30-3, root growths of all four PIC30-OX lines were inhibited by approximately 97-98% (FIG. 6B). Since PIC30-OX lines show hypersensitivity at micromolar concentrations of picloram, root growth inhibition was assayed on nanomolar concentrations of picloram. As shown in FIG. 6C, one media containing a mere 100 nM concentration of picloram, root growth inhibition of PIC30-OX lines was in the range of 87-89% compared to approximately 10% inhibition in both wild type and pic30-3.

Moreover, foliar treatment of adult plants with 100 g/ha of picloram also showed that PIC30-OX lines were hypersensitive to picloram. On the contrary, all four PIC30-OX lines displayed wild-type sensitivity to both IAA and 1-NAA.

Because overexpression of PIC30 makes plants hypersensitive to picloram, Applicants investigated whether overexpression of mutant pic30 in wild type background results in picloram insensitivity. Among the three pic30 allelic mutants, only the pic30-1 mutation results in the change of a single amino acid and therefore, pic30-1 was chosen for overexpression in wild type. When three independent homozygous lines of pic30-1-OX were tested on picloram, they displayed picloram insensitive primary root growth (FIGS. 6D-E). These results explicitly indicate that plant sensitivity to picloram can be regulated through the PIC30 gene and picloram resistance can be simply generated by overexpressing mutant gene due to the semi-dominant nature of the mutation.

Example 1.13. The Pic30-3 Gene is Defective in Picloram Uptake

Since PIC30 is categorized as a general substrate transporter and mutations in pic30 selectively confer insensitivity to the picolinate class of auxinic herbicides, the possibility of picloram transport through PIC30 was investigated using radiolabelled $^{14}C$-picloram. As high level of PIC30 expression was observed in primary root tips, 15 mm section of roots from the root tips of 9 day-old seedlings were used for in planta picloram transport assays. It was observed that picloram uptake was significantly lower in pic30-3 than in wild type root sections (FIG. 7A).

Furthermore, to verify whether PIC30 is selective for picloram uptake, an in planta IAA-'3 transport assay was performed using radiolabelled $^3$H-IAA with similar 15 mm apical root sections. In contrast to picloram uptake, no difference was detected in IAA uptake between wild type and pic30-3 (FIG. 7B), strongly indicating that PIC30 specifically transports picloram but not the natural auxin, IAA.

To test whether complementation of picloram phenotypes in PIC30-OX lines is due to restoration of picloram uptake ability, transport assay was performed with two of the four PIC30-OX lines tested for root growth responses. Picloram uptake in these two PIC30-OX lines was found to be approximately 26-30 times higher than that in wild type roots (FIG. 7C).

Example 1.14. The Pic30-3 but not the Pic30-1 and Pic30-2 May be Defective in Nitrate Transport To test the ability of pic30 mutants to transport nitrate into plants, in planta chlorate sensitivity assay was performed. Chlorate (a transport analog of nitrate) is transported into plants through several nitrate transporters, and wild type *Arabidopsis* plants are highly susceptible to chlorate induced leaf bleaching. Chlorate sensitivity assays were performed at both seedling and adult stages. While no difference was observed among wild type and the three pic30 mutants under control conditions, pronounced cotyledon and leaf bleaching was observed in wild type, pic30-1 and pic30-2 but not in pic30-3 (FIGS. 8A-B), indicating that pic30-3 mutant seedlings/plants are insensitive to the chlorate induced necrosis and leaf bleaching.

Complementation of chlorate sensitivity in PIC30-OX lines were also tested at both seedling and adult stages. As shown in FIG. 8C, similar to picloram hypersensitivity, all four PIC30-OX lines displayed hypersensitivity to chlorate at the seedling stage. Furthermore, three week-old adult PIC30-OX plants irrigated with chlorate solution displayed sensitivity to chlorate, even though hypersensitive response was not observed with any of the four PIC30-OX lines (FIG. 8D). These observations confirm that overexpression of PIC30 can restore chlorate/nitrate transport functions in pic30-3.

Example 1.15. Expression of PIC30 is Developmentally and Diurnally Regulated

To study the tissue/organ specific expression pattern of PIC30 gene, Applicants used a combination of qRT-PCR and histochemical GUS staining/fluorometric MUG assay with wild type and transgenic plants carrying the PIC30$_{pro}$:: PIC30-GUS reporter construct, respectively. Samples were collected at different developmental stages, and expression of PIC30 was examined.

As observed by qRT-PCR, PIC30 transcripts were detected at both seedling and adult stages of wild type plants (FIG. 9A). In 4 week-old plants, PIC30 transcripts were detected in root, shoot, flowers, rosette and cauline leaves (FIG. 9A). Histochemical GUS staining also revealed a similar pattern of expression (FIGS. 9B-F). Interestingly, PIC30 expression was stronger in old rosette leaves than in relatively younger leaves (FIG. 9D). Moreover, compared to higher level of PIC30 expression in mature flowers, relatively low level of expression was observed in both flower buds and immature flowers (FIG. 9E).

At the seedling stage, higher levels of PIC30 expression was observed in 8 day-old seedlings compared to 4 day-old seedlings (FIGS. 9B-C), suggesting that PIC30 gene expression may be developmentally regulated. To further study the developmental regulation of PIC30 gene expression, PIC30-GUS expression was tracked from the $1^{st}$ to $7^{th}$ day after germination, at 24 hour intervals. It was observed that the level of PIC30-GUS expression goes up with the age of the plant, at least within the tested period (FIG. 9G).

Since PIC30 was identified in a picloram based mutant screen, the effect of picloram treatment on PIC30 expression was tested. The results show that picloram did not have influence on the PIC30 gene expression (FIG. 9H). On the other hand, the expression of most genes involved in nitrate transport is diurnally regulated, and since PIC30 may also be a nitrate transporter, Applicants hypothesized that expression of PIC30 may also be subjected to diurnal regulation.

To test the aforementioned possibility, seedlings were grown in a 12 hour light/12 hour dark regime, and samples were collected at 6-hour time intervals. qRT-PCR analysis revealed that the expression of PIC30 was diurnally regulated with the highest expression during the dawn (FIG. 9I).

Example 1.16. PIC30 is an MFS and NOD Domain Containing Protein, Localized to the Plasma Membrane Despite some similarities in plant responses to various auxinic chemicals, many differences in responses to different auxinic chemicals have also been reported. While IAA, 2,4-D and 1-NAA interact with the same auxin co-receptors, TIR1, AFB1, AFB2 and AFB3, picloram interacts with AFB4 and AFB5, suggesting that the mode of action of picloram may be considerably different from other commonly used auxinic chemicals. Even with functional similarities, differences exist in transport of different auxinic chemicals.

In spite of the wide commercial use of picolinate herbicides, proteins involved in picloram transport into plant cells have never been described in the literature. As picloram is a completely synthetic chemical, it should be transported as a secondary substrate via a native transporter protein.

Applicants' results in this Example indicate that PIC30, which has been mapped to At2g39210 locus, encodes a transporter protein that contains a MFS and a NOD-domain. Applicants identified three allelic mutants of PIC30 (pic30-1, pic30-2 and pic30-3) containing point mutations in this locus (FIG. 2C). The following three experimental evidences indicate that the mutation in pic30 is responsible for the picloram related phenotypes. All three mutations are semi-dominant mutants (FIG. 2F) and confer picloram insensitivity (FIGS. 2D-E). In addition, overexpression of pic30-1 confers picloram insensitivity in wild type plants (FIG. 6E). Furthermore, ectopic expression of PIC30 in pic30-3 confers picloram hypersensitivity (FIG. 6C).

Since the mature pic30 transcript in pic30-3 contains premature in-frame stop codons (FIG. 4A), it may produce a highly truncated protein if translated. Therefore, the pic30-3 mutant was selected as an alternative for a knockout mutant in Applicants' studies. The three mutant alleles show both similar and variable phenotypes due to the positioning of point mutations, allowing Applicants to draw valuable information about the involvement of different domains in PIC30 function.

Several MFS proteins have been previously characterized. Most importantly, all the proteins identified in this family so far have been implicated as membrane localized transporter proteins. Co-localization of PIC30-GFP with two plasma membrane markers confirm that PIC30 is indeed localized to the plasma membrane, strongly supporting a putative transporter function.

Example 1.17. The Pic30 Mutation Causes Selective Insensitivity Against Picolinate Herbicides with a Semi-Dominant Trait All the previously characterized picolinate insensitive signaling mutants show recessive traits. For instance, several mutant alleles of SGT1 and AFB5 are specifically insensitive to picolinate herbicides. In a study using in vitro assays, it was suggested that AFB4 and AFB5 auxin receptor F-box proteins are the targets of picolinate herbicides.

In contrast, pic30 mutation shows a semi-dominant trait (FIG. 2F). This important characteristic of pic30 mutants, the selective insensitivity to picolinate herbicides and plasma membrane localization, collectively lead Applicants to the initial speculation that the PIC30 protein may be specifically involved in picloram transport rather than in signaling cascade. As a mutation in PIC30 results in picloram insensitivity, and the heterozygote confers partial insensitivity to picloram, it is logical to assume that the PIC30 protein may function in picloram influx.

The observed picloram related phenotypes of pic30 mutants are similar in certain ways to the semi-dominant gain-of-function mutant pdr9-1 in *Arabidopsis*. pdr9-1 contains a mutation in a pleiotropic drug resistant transporter gene that belongs to the ABC transporter superfamily, and is involved in the transport of natural (IBA) and synthetic (2,4-D) compounds out of cells. According to the same line of logic, PIC30 is also presumed to be involved in the transport of synthetic picloram as well as some natural compounds, as members of MFS family are often implicated as general transporters in plants.

Example 1.18. PIC30 Transports Picloram into the Cells

Many proteins containing MFS domains are known to transport solutes, amino acids, hormones and nutrients. Thus, Applicants investigated the possible transporter function(s) of PIC30, focusing on its ability to transport picloram and other naturally occurring substrates. All three pic30 mutants show specific insensitivity to the picolinate herbicides picloram and aminopyralid but demonstrate wild-type sensitivity to the other commonly used synthetic auxins 2,4-D and 1-NAA as well as the natural auxin IAA (FIGS. 3A-F). This observation is further supported by the picloram hypersensitivity (FIGS. 6B-6C) and normal IAA or 1-NAA sensitivity in lines that overexpress PIC30 in pic30-3 background. All these data indicate that PIC30 may be involved in transport of picolinate herbicides.

Using radiolabelled $^{14}C$ picloram, Applicants have confirmed that pic30-3 is defective in the uptake of picloram compared to wild type (FIG. 7A). While the evidence is indirect, the semi-dominant nature of the mutation and the plasma membrane localization of the protein strongly support the notion that PIC30 is involved in picloram influx. Another possibility is that PIC30 may be regulating another transporter protein, thereby indirectly regulating picloram transport. However, this is highly unlikely, because when the same radioactive picloram transport assay was performed using transgenic lines that overexpress PIC30 gene in pic30-3 background, all the overexpression lines showed very high accumulation of picloram in root tissues (FIG. 7C), strongly indicating that PIC30 is an influx transporter of picloram.

Example 1.19. Diurnal Regulation of PIC30 Expression and its Function in Nitrate Transport in *Arabidopsis*

Diurnal variation in gene expression is a major characteristic of many genes that are involved in either nitrate transport or metabolism. The expression of several genes involved in nitrate transport is elevated during day-time to bring in nitrate into the plant system and its subsequent loading into the appropriate tissues/organs. Expression of PIC30 gene is also regulated diurnally, with relatively higher expression during day-time than at night-time (FIG. 9I). Moreover, PIC30 strongly expresses in roots during both cotyledon and adult stages, implying that PIC30 might be involved in uploading nitrate (and other possible inorganic anions) into the roots during day-time.

Nitrate transporter proteins from different plant species have also been implicated in chlorate transport, rendering plants sensitive to exogenous applications of chlorate. However, mutants that are defective in nitrate influx show insensitivity to chlorate induced cotyledon and leaf bleaching, which have proven to be a simple, yet powerful screening tool to test mutants impaired in nitrate transport. In planta chlorate sensitivity assays demonstrated the chlorate insensitive phenotypes in pic30-3, both during seedling and adult stages (FIGS. 8A-B), implying that PIC30 functions as a nitrate transporter in *Arabidopsis*. However, both pic30-1 and pic30-2 mutations did not affect the nitrate transport function. This could be due to the nature and location of the mutations within the gene. Whereas mutation in pic30-1 replaces a single amino acid within the NOD-domain, the mutation in pic30-2 results in a truncated protein containing the full NOD-domain and a partial MFS-domain. It is possible that mutated proteins in pic30-1 and pic30-2 are still capable of functionally transporting nitrate into the plant. However, the mutation in pic30-3 that alters splicing may produce a highly truncated protein completely lacking biological functions. Thus, by using pic30-1 and pic30-2 mutations, it is possible to generate crop plants that are resistant to picloram without compromising the ability of nitrate transport, which is an important nutrient for plants.

The PIC30-OX lines show hypersensitivity to chlorate during the seedling stage but show wild-type sensitivity at the adult stage (FIGS. 8C-D). The same overexpression lines are hypersensitive to picloram at both seedling (FIG. 6B) and adult stages. The explanation for this difference in chlorate and picloram sensitivities is unclear. However, it is likely that transport of chlorate/nitrate may be a tightly regulated process to bring in optimum level of nitrate into the plant system.

Example 1.20. PIC30 Expression is Regulated by NMD Pathway

As described above, the transcript level of pic30 is significantly low in all three mutants than PIC30 transcripts in wild type (FIG. 4B). This appears to be due to the degradation of pic30 mutant transcripts through nonsense-mediated mRNA decay (NMD) machinery that predominantly destroys aberrant transcripts with premature stop codons (Chang et al. 2007; Kurihara et al. 2009).

Consistent with this, pic30 transcript abundance was significantly higher in the NMD mutant upf3-1 background than in pic30-3 mutant background (FIG. 4C). Among the three pic30 mutants, accumulation of pic30 transcript is lowest in pic30-3 compared to either pic30-1 or pic30-2. Possible reasons for this phenomenon are the nature and location of the mutation as well as splicing status of the transcripts. Unlike the pic30 transcripts in either pic30-1 or pic30-2, in pic30-3 background, pic30 transcript does not undergo splicing to remove an intron (FIG. 4A), resulting in the introduction of premature in-frame stop codons.

Similar to pic30-3, mutation in pic30-2 also results in a premature stop codon, but closer to the 3'end of the transcript. Therefore, the transcript may be less vulnerable to NMD. Consistent with this, pic30-1 mutant transcript is least subjected to mRNA degradation as it is a missense mutation that does not introduce a premature stop codon. Taken together, Applicants' results confirm the involvement of NMD in the regulation of pic30 transcript abundance in *Arabidopsis*, which should be taken into consideration during future manipulations of this gene.

Example 1.21. Potential Applications of PIC30 Gene in Genetic Engineering

Potential PIC30 orthologs are present in several commercially important crop plants, including soybean and maize. Therefore, present knowledge on the role of PIC30 in picloram/nitrate transport and the impact of different point mutations on PIC30 functions can be used for possible genetic manipulation of commercially important crops. Considering the facts that mutation in pic30-1 abolishes picloram transport function without disrupting its nitrate transport ability and that the overexpression of pic30-1 in wild type confers insensitivity to auxinic herbicide can be possibly used in genetic manipulation of picloram sensitivity in plants without altering the transport of nitrate.

Since picloram transport into the plant can be enhanced through overexpression of PIC30 in *Arabidopsis*, this aspect can be further explored for bioremediation efforts. It is a well known fact that the half-life of the picloram in soil ranges from a few months to several years depending on both soil and climate conditions. Agricultural land contaminated with picloram is generally not suitable for the cultivation of dicot crops. Therefore, plant species that are highly tolerant to picolinate herbicides can be generated by genetic modification to overexpress PIC30 and probably use for bioremediation of agricultural land contaminated with picolinate herbicides, prior to cultivation of dicot crops.

Additional experimental results are summarized in FIGS. 10-14.

Without further elaboration, it is believed that one skilled in the art can, using the description herein, utilize the present disclosure to its fullest extent. The embodiments described herein are to be construed as illustrative and not as constraining the remainder of the disclosure in any way whatsoever. While the embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

What is claimed is:

1. A modified plant or seed, wherein the modified plant or seed comprises a mutated pic30 gene, wherein the mutated pic30 gene comprises a nucleotide sequence selected from the group consisting of SEQ ID NO: 1, SEQ ID NO: 2, and SEQ ID NO: 3; and wherein the modified plant or seed is resistant to at least one herbicide.

2. The modified plant or seed of claim 1, wherein the modified plant or seed is a dicot selected from the group consisting of soybean, lettuce, tomato, potato, legumes, peas, beans, lentils, peanuts, and cotton.

3. The modified plant or seed of claim 1, wherein the mutated gene is a transgene.

4. The modified plant or seed of claim 1, wherein the modified plant or seed is also resistant to one or more sources of environmental stress, wherein the one or more sources of environmental stress are selected from the group consisting of drought, high temperature, UV radiation, microbial contamination, biotic stress, abiotic stress, plant pathogenesis, and combinations thereof.

5. A method of controlling the growth of weeds in a field, said method comprising: applying at least one herbicide to the field, and applying a modified plant or seed to the field, wherein the modified plant or seed comprises a mutated pic30 gene, wherein the mutated pic30 gene comprises a nucleotide sequence selected from the group consisting of SEQ ID NO: 1, SEQ ID NO: 2, and SEQ ID) NO: 3, and wherein the modified plant or seed is resistant to the at least one herbicide and one or more sources of environmental stress.

6. The method of claim 5, wherein the applying of the modified plant or seed to the field occurs before, during or after applying the herbicide to the field.

7. The method of claim 5, further comprising a step of growing the modified plant in the field.

8. The method of claim 7, wherein the growing occurs before, during or after applying the herbicide to the field.

9. The method of claim 5, wherein the at least one herbicide is a picolinate herbicide.

10. The method of claim 9, wherein the picolinate herbicide is selected from the group consisting of aminocyclopyrachlor, aminopyralid, clopyralid, tryclopyr, picloram, arylpicolinates, and combinations thereof.

11. The method of claim 5, wherein the one or more sources of environmental stress are selected from the group consisting of drought, high temperature, UV radiation, microbial contamination, biotic stress, abiotic stress, plant pathogenesis, and combinations thereof.

12. A method of developing a modified plant or seed that is resistant to at least one herbicide, wherein the method comprises: introducing a mutated pic30 gene into a plant or plant cell, wherein the mutated pic30 gene is selected from the group consisting of SEQ ID NO: 1, SEQ ID NO: 2, and SEQ ID NO: 3, and optionally collecting seeds that comprise the mutated pic30 gene from said plant.

13. The method of claim 12, wherein the introducing comprises transforming the plant or plant cell with the mutated pic30 gene.

14. The method of claim 13, wherein the transforming occurs by a method selected from the group consisting of floral-dip transformation, callus transformation, tissue transformation, particle bombardment, and combinations thereof.

15. The method of claim 13, wherein the introducing occurs by floral-dip transformation.

16. The method of claim 13, wherein the introducing comprises mutating an endogenous gene in a plant or seed.

17. The method of claim 16, wherein the mutating occurs by a method selected from the group consisting of chemical mutation, site directed mutagenesis, irradiation, and combinations thereof.

18. The method of claim 12, wherein the introducing occurs at a seedling stage or an adult stage of a plant.

19. The method of claim 12, wherein the introducing confers resistance of the plant or seed to one or more sources of environmental stress, wherein the one or more sources of environmental stress are selected from the group consisting of drought, high temperature, UV radiation, microbial contamination, biotic stress, abiotic stress, plant pathogenesis, and combinations thereof.

20. The method of claim 5, wherein the modified plant or seed expresses a mutated PIC30 protein, wherein the mutated PIC30 protein comprises an amino acid sequence selected from the group consisting of SEQ ID NO: 4, SEQ ID NO: 5, and SEQ ID NO: 6.

* * * * *

SEQUENCE LISTING

```
<160> NUMBER OF SEQ ID NOS: 6

<210> SEQ ID NO 1
<211> LENGTH: 1945
<212> TYPE: DNA
<213> ORGANISM: Arabidopsis thaliana

<400> SEQUENCE: 1
atggtggctg caagtcccgg tggctcaatg aagagcttaa ccatccaaat cctaaccgga      60
agatggttca tgttctttgg aagtctctta atcatgtcga cagctggagc cacttacatg     120
ttcggtatct actcaggcga tatcaaggaa accttaggct acgaccaaac cactcttaat     180
ctcctaagtt tcttcaaaga tctcggagcc aacgttggag tcctcgcggg tctactcaat     240
gaggtaactc ctccttggtt catcctcttg atcggagcca tccttaactt ctttggatac     300
ttcatgattt ggctcgccgt cacggaacgg atctcgaaac ctcaagtttg gcacatgtgt     360
ctctatatct gcgttggagc caactcgcag ttgttcgcta ataccggatc tctcgtcacg     420
tgcgttaaga acttcccgga gtcacgtggg gttgtcttgg ggattctcaa aggctacgtt     480
ggtcttagtg gcgccattat tacacagctc taccgtgcct tttatggtga agacacaaaa     540
gagctcatct tgatgattgg taagcacaat ttctaaaatt attcatgaga ctatatggtt     600
aatggcatga acagagtaaa acagagcaaa aacagagcaa aacagagtaa atcttggata     660
gaaacacata ctaattgtat gagtgattgt atttgtaggt tggttgccgg ctatagtctc     720
gtttgcgttt ttgagaacga taagaataat gaaagtgaaa agacagacaa acgaactaaa     780
```

```
ggtgttctat aacttcctct acatatcgct cgggcttgcg acgtttctca tggtggtcat    840
catcatcaac aaactctcgg gctttacaca aagcgagttt ggaggtagcg ccgcggtagt    900
gatcgtctta cttcttttgc ccattatagt cgtcatcttg aagagaaga  agctttggaa    960 ggagaaacaa gtcgccttaa acgatccagc acccatcaat gtcgtaactg agaaacccaa   1020
gttagattca tcagagttca aagatgatga tggtgaagag tcaaaggagg tagtggagaa   1080
ggtgaaaaca ccgtcgtgtt ggacgactgt gtttaatcca ccggagagag gagatgacta   1140
tacaatcttg caagcgttgt ttagcgtaga catgttgatt ttgttcttag caacgatatg   1200
tggcgtagga gggactttga cggcgataga caatttgggt caaatcggaa actcgttggg   1260
ttacccgaag agaagcgtaa gcacgtttgt gtcactcgta agcatatgga attactatgg   1320
tcgtgtggtt tcaggtgtgg tctctgagat cttcttgatc aaatacaaat ttccaaggcc   1380
tttaatgctc acgatggtcc tcctcttgtc ctgcgcgggt cacctcctca tcgcctttaa   1440
tgtccccggt ggactttatg tcgcatcggt catcataggg ttttgttttg gtgcgcaatg   1500
gcctcttcta tttgctataa tatctgagat tttcgggctt aagtactact cgacattgta   1560
taacttcggg tcagtcgcga gcccgatcgg gtcttacttg ctaaacgttc gggtcgcagg   1620
gtatttgtac gacgtggagg cgggtaagca atataaggca ttagggaaaa cgagagtaga   1680
agggcaagat ttgaattgca taggcacgtc ttgttttaag ttgtcttttta taataattgc   1740 cgctgtaact ttgttcggtg tattggtctc gatggttttg gtgatccgga ccaagaagtt   1800
ttacaagagt gatatctaca aaaagtttag agaaaaagcg ttagctgccg agatggagat   1860
ggcagcgccg gctgcagcca gatctaccgt ggctaaggaa gacaaggatg atgttaaagg   1920
caaagtaata ggaaaaggag ggtaa                                          1945
```

<210> SEQ ID NO 2
<211> LENGTH: 1945
<212> TYPE: DNA
<213> ORGANISM: Arabidopsis thaliana

<400> SEQUENCE: 2

```
atggtggctg caagtcccgg tggctcaatg aagagcttaa ccatccaaat cctaaccgga     60
agatggttca tgttctttgg aagtctctta atcatgtcga cagctggagc cacttacatg    120
ttcggtatct actcaggcga tatcaaggaa accttaggct acgaccaaac cactcttaat    180
ctcctaagtt tcttcaaaga tctcggagcc aacgttggag tcctcgcggg tctactcaat    240
gaggtaactc ctccttggtt catcctcttg atcggagcca tccttaactt ctttggatac    300
ttcatgattt ggctcgccgt cacggaacgg atctcgaaac tcaagtttg  gcacatgtgt    360 ctctatatct gcgttggagc caactcgcag tcgttcgcta ataccggatc tctcgtcacg    420
tgcgttaaga acttcccgga gtcacgtggg gttgtcttgg ggattctcaa aggctacgtt    480
ggtcttagtg gcgccattat tacacagctc taccgtgcct tttatggtga agacacaaaa    540
gagctcatct tgatgattgg taagcacaat ttctaaaatt attcatgaga ctatatggtt    600
aatggcatga acagagtaaa acagagcaaa acagagcaa  acagagtaa  atcttggata    660 gaaacacata ctaattgtat gagtgattgt atttgtaggt tggttgccgg ctatagtctc    720
gtttgcgttt ttgagaacga taagaataat gaaagtgaaa agacagacaa acgaactaaa    780
ggtgttctat aacttcctct acatatcgct cgggcttgcg acgtttctca tggtggtcat    840
catcatcaac aaactctcgg gctttacaca aagcgagttt ggaggtagcg ccgcggtagt    900
gatcgtctta cttcttttgc ccattatagt cgtcatcttg aagagaaga  agctttggaa    960
```

```
ggagaaacaa gtcgccttaa acgatccagc acccatcaat gtcgtaactg agaaacccaa    1020
gttagattca tcagagttca aagatgatga tggtgaagag tcaaaggagg tagtggagaa    1080
ggtgaaaaca ccgtcgtgtt ggacgactgt gtttaatcca ccggagagag agatgacta     1140 tacaatcttg caagcgttgt ttagcgtaga catgttgatt ttgttcttag caacgatatg    1200
tggcgtagga gggactttga cggcgataga caatttgggt caaatcggaa actcgttggg    1260
ttacccgaag agaagcgtaa gcacgtttgt gtcactcgta agcatatgga attactatgg    1320
tcgtgtggtt tcaggtgtgg tctctgagat cttcttgatc aaatacaaat ttccaaggcc    1380
tttaatgctc acgatggtcc tcctcttgtc ctgcgcgggt cacctcctca tcgcctttaa    1440
tgtccccggt ggactttatg tcgcatcggt catcataggg ttttgttttg gtgcgcaatg    1500
acctcttcta tttgctataa tatctgagat tttcgggctt aagtactact cgacattgta    1560
taacttcggg tcagtcgcga gcccgatcgg gtcttacttg ctaaacgttc gggtcgcagg    1620
gtatttgtac gacgtggagg cgggtaagca atataaggca ttagggaaaa cgagagtaga    1680
agggcaagat ttgaattgca taggcacgtc ttgttttaag ttgtctttta taataattgc    1740
cgctgtaact ttgttcggtg tattggtctc gatggttttg gtgatccgga ccaagaagtt    1800
ttacaagagt gatatctaca aaaagtttag agaaaaagcg ttagctgccg agatggagat    1860
ggcagcgccg gctgcagcca gatctaccgt ggctaaggaa gacaaggatg atgttaaagg    1920
caaagtaata ggaaaaggag ggtaa                                          1945
```

<210> SEQ ID NO 3
<211> LENGTH: 1945
<212> TYPE: DNA
<213> ORGANISM: Arabidopsis thaliana

<400> SEQUENCE: 3

```
atggtggctg caagtcccgg tggctcaatg aagagcttaa ccatccaaat cctaaccgga     60
agatggttca tgttctttgg aagtctctta atcatgtcga cagctggagc cacttacatg    120
ttcggtatct actcaggcga tatcaaggaa accttaggct acgaccaaac cactcttaat    180
ctcctaagtt tcttcaaaga tctcggagcc aacgttggag tcctcgcggg tctactcaat    240
gaggtaactc ctccttggtt catcctcttg atcggagcca tccttaactt ctttggatac    300
ttcatgattt ggctcgccgt cacggaacgg atctcgaaac ctcaagtttg cacatgtgt     360 ctctatatct gcgttggagc caactcgcag tcgttcgcta ataccggatc tctcgtcacg    420
tgcgttaaga acttcccgga gtcacgtggg gttgtcttgg ggattctcaa aggctacgtt    480
ggtcttagtg gcgccattat tacacagctc taccgtgcct tttatggtga agacacaaaa    540
gagctcatct tgatgattgg taagcacaat ttctaaaatt attcatgaga ctatatggtt    600
aatggcatga acagagtaaa acagagcaaa acagagcaa acagagtaa atcttggata      660 gaaacacata ctaattgtat gagtgattgt atttgtaagt tggttgccgg ctatagtctc    720
gtttgcgttt ttgagaacga taagaataat gaaagtgaaa agacagacaa acgaactaaa    780
ggtgttctat aacttcctct acatatcgct cgggcttgcg acgtttctca tggtggtcat    840
catcatcaac aaactctcgg gctttacaca aagcgagttt ggaggtagcg ccgcggtagt    900
gatcgtctta cttcttttgc ccattatagt cgtcatcttg aagagaaga agctttggaa     960 ggagaaacaa gtcgccttaa acgatccagc acccatcaat gtcgtaactg agaaacccaa   1020
gttagattca tcagagttca aagatgatga tggtgaagag tcaaaggagg tagtggagaa   1080
```

```
ggtgaaaaca ccgtcgtgtt ggacgactgt gtttaatcca ccggagagag gagatgacta   1140
tacaatcttg caagcgttgt ttagcgtaga catgttgatt ttgttcttag caacgatatg   1200
tggcgtagga gggactttga cggcgataga caatttgggt caaatcggaa actcgttggg   1260
ttacccgaag agaagcgtaa gcacgtttgt gtcactcgta agcatatgga attactatgg   1320
tcgtgtggtt tcaggtgtgg tctctgagat cttcttgatc aaatacaaat ttccaaggcc   1380
tttaatgctc acgatggtcc tcctcttgtc ctgcgcgggt cacctcctca tcgcctttaa   1440
tgtccccggt ggactttatg tcgcatcggt catcataggg ttttgttttg gtgcgcaatg   1500
gcctcttcta tttgctataa tatctgagat tttcgggctt aagtactact cgacattgta   1560
taacttcggg tcagtcgcga gcccgatcgg gtcttacttg ctaaacgttc gggtcgcagg   1620
gtatttgtac gacgtggagg cgggtaagca atataaggca ttagggaaaa cgagagtaga   1680
agggcaagat ttgaattgca taggcacgtc ttgttttaag ttgtctttta taataattgc   1740
cgctgtaact ttgttcggtg tattggtctc gatggttttg gtgatccgga ccaagaagtt   1800
ttacaagagt gatatctaca aaaagtttag agaaaaagcg ttagctgccg agatggagat   1860
ggcagcgccg gctgcagcca gatctaccgt ggctaaggaa gacaaggatg atgttaaagg   1920
caaagtaata ggaaaaggag ggtaa                                         1945
```

<210> SEQ ID NO 4
<211> LENGTH: 601
<212> TYPE: PRT
<213> ORGANISM: Arabidopsis thaliana

<400> SEQUENCE: 4

```
Met Val Ala Ala Ser Pro Gly Gly Ser Met Lys Ser Leu Thr Ile Gln
1               5                   10                  15

Ile Leu Thr Gly Arg Trp Phe Met Phe Gly Ser Leu Leu Ile Met
            20                  25                  30

Ser Thr Ala Gly Ala Thr Tyr Met Phe Gly Ile Tyr Ser Gly Asp Ile
        35                  40                  45

Lys Glu Thr Leu Gly Tyr Asp Gln Thr Thr Leu Asn Leu Leu Ser Phe
    50                  55                  60

Phe Lys Asp Leu Gly Ala Asn Val Gly Val Leu Ala Gly Leu Leu Asn
65                  70                  75                  80

Glu Val Thr Pro Pro Trp Phe Ile Leu Leu Ile Gly Ala Ile Leu Asn
                85                  90                  95

Phe Phe Gly Tyr Phe Met Ile Trp Leu Ala Val Thr Glu Arg Ile Ser
            100                 105                 110

Lys Pro Gln Val Trp His Met Cys Leu Tyr Ile Cys Val Gly Ala Asn
        115                 120                 125

Ser Gln Leu Phe Ala Asn Thr Gly Ser Leu Val Thr Cys Val Lys Asn
    130                 135                 140

Phe Pro Glu Ser Arg Gly Val Val Leu Gly Ile Leu Lys Gly Tyr Val
145                 150                 155                 160

Gly Leu Ser Gly Ala Ile Ile Thr Gln Leu Tyr Arg Ala Phe Tyr Gly
                165                 170                 175

Glu Asp Thr Lys Glu Leu Ile Leu Met Ile Gly Trp Leu Pro Ala Ile
            180                 185                 190

Val Ser Phe Ala Phe Leu Arg Thr Ile Arg Ile Met Lys Val Lys Arg
        195                 200                 205

Gln Thr Asn Glu Leu Lys Val Phe Tyr Asn Phe Leu Tyr Ile Ser Leu
    210                 215                 220
```

Gly Leu Ala Thr Phe Leu Met Val Ile Ile Asn Lys Leu Ser
225                 230                 235                 240

Gly Phe Thr Gln Ser Glu Phe Gly Gly Ser Ala Ala Val Val Ile Val
                245                 250                 255

Leu Leu Leu Leu Pro Ile Ile Val Val Ile Leu Glu Glu Lys Lys Leu
            260                 265                 270

Trp Lys Glu Lys Gln Val Ala Leu Asn Asp Pro Ala Pro Ile Asn Val
        275                 280                 285

Val Thr Glu Lys Pro Lys Leu Asp Ser Ser Glu Phe Lys Asp Asp Asp
    290                 295                 300

Gly Glu Glu Ser Lys Glu Val Val Glu Lys Val Lys Thr Pro Ser Cys
305                 310                 315                 320

Trp Thr Thr Val Phe Asn Pro Pro Glu Arg Gly Asp Asp Tyr Thr Ile
                325                 330                 335

Leu Gln Ala Leu Phe Ser Val Asp Met Leu Ile Leu Phe Leu Ala Thr
            340                 345                 350

Ile Cys Gly Val Gly Gly Thr Leu Thr Ala Ile Asp Asn Leu Gly Gln
        355                 360                 365

Ile Gly Asn Ser Leu Gly Tyr Pro Lys Arg Ser Val Ser Thr Phe Val
    370                 375                 380

Ser Leu Val Ser Ile Trp Asn Tyr Tyr Gly Arg Val Val Ser Gly Val
385                 390                 395                 400

Val Ser Glu Ile Phe Leu Ile Lys Tyr Lys Phe Pro Arg Pro Leu Met
                405                 410                 415

Leu Thr Met Val Leu Leu Leu Ser Cys Ala Gly His Leu Leu Ile Ala
            420                 425                 430

Phe Asn Val Pro Gly Gly Leu Tyr Val Ala Ser Val Ile Ile Gly Phe
        435                 440                 445

Cys Phe Gly Ala Gln Trp Pro Leu Leu Phe Ala Ile Ile Ser Glu Ile
    450                 455                 460

Phe Gly Leu Lys Tyr Tyr Ser Thr Leu Tyr Asn Phe Gly Ser Val Ala
465                 470                 475                 480

Ser Pro Ile Gly Ser Tyr Leu Leu Asn Val Arg Val Ala Gly Tyr Leu
                485                 490                 495

Tyr Asp Val Glu Ala Gly Lys Gln Tyr Lys Ala Leu Gly Lys Thr Arg
            500                 505                 510

Val Glu Gly Gln Asp Leu Asn Cys Ile Gly Thr Ser Cys Phe Lys Leu
        515                 520                 525

Ser Phe Ile Ile Ile Ala Ala Val Thr Leu Phe Gly Val Leu Val Ser
    530                 535                 540

Met Val Leu Val Ile Arg Thr Lys Lys Phe Tyr Lys Ser Asp Ile Tyr
545                 550                 555                 560

Lys Lys Phe Arg Glu Lys Ala Leu Ala Ala Glu Met Glu Met Ala Ala
                565                 570                 575

Pro Ala Ala Ala Arg Ser Thr Val Ala Lys Glu Asp Lys Asp Asp Val
            580                 585                 590

Lys Gly Lys Val Ile Gly Lys Gly Gly
        595                 600

<210> SEQ ID NO 5
<211> LENGTH: 453
<212> TYPE: PRT
<213> ORGANISM: Arabidopsis thaliana

```
<400> SEQUENCE: 5

Met Val Ala Ala Ser Pro Gly Gly Ser Met Lys Ser Leu Thr Ile Gln
1               5                   10                  15

Ile Leu Thr Gly Arg Trp Phe Met Phe Phe Gly Ser Leu Leu Ile Met
            20                  25                  30

Ser Thr Ala Gly Ala Thr Tyr Met Phe Gly Ile Tyr Ser Gly Asp Ile
        35                  40                  45

Lys Glu Thr Leu Gly Tyr Asp Gln Thr Thr Leu Asn Leu Leu Ser Phe
    50                  55                  60

Phe Lys Asp Leu Gly Ala Asn Val Gly Val Leu Ala Gly Leu Leu Asn
65                  70                  75                  80

Glu Val Thr Pro Pro Trp Phe Ile Leu Ile Gly Ala Ile Leu Asn
                85                  90                  95

Phe Phe Gly Tyr Phe Met Ile Trp Leu Ala Val Thr Glu Arg Ile Ser
                100                 105                 110

Lys Pro Gln Val Trp His Met Cys Leu Tyr Ile Cys Val Gly Ala Asn
            115                 120                 125

Ser Gln Ser Phe Ala Asn Thr Gly Ser Leu Val Thr Cys Val Lys Asn
        130                 135                 140

Phe Pro Glu Ser Arg Gly Val Val Leu Gly Ile Leu Lys Gly Tyr Val
145                 150                 155                 160

Gly Leu Ser Gly Ala Ile Ile Thr Gln Leu Tyr Arg Ala Phe Tyr Gly
                165                 170                 175

Glu Asp Thr Lys Glu Leu Ile Leu Met Ile Gly Trp Leu Pro Ala Ile
            180                 185                 190

Val Ser Phe Ala Phe Leu Arg Thr Ile Arg Ile Met Lys Val Lys Arg
        195                 200                 205

Gln Thr Asn Glu Leu Lys Val Phe Tyr Asn Phe Leu Tyr Ile Ser Leu
    210                 215                 220

Gly Leu Ala Thr Phe Leu Met Val Val Ile Ile Asn Lys Leu Ser
225                 230                 235                 240

Gly Phe Thr Gln Ser Glu Phe Gly Gly Ser Ala Ala Val Val Ile Val
                245                 250                 255

Leu Leu Leu Leu Pro Ile Ile Val Ile Leu Glu Glu Lys Lys Leu
                260                 265                 270

Trp Lys Glu Lys Gln Val Ala Leu Asn Asp Pro Ala Pro Ile Asn Val
            275                 280                 285

Val Thr Glu Lys Pro Lys Leu Asp Ser Ser Glu Phe Lys Asp Asp Asp
        290                 295                 300

Gly Glu Glu Ser Lys Glu Val Val Glu Lys Val Lys Thr Pro Ser Cys
305                 310                 315                 320

Trp Thr Thr Val Phe Asn Pro Pro Glu Arg Gly Asp Asp Tyr Thr Ile
                325                 330                 335

Leu Gln Ala Leu Phe Ser Val Asp Met Leu Ile Leu Phe Leu Ala Thr
            340                 345                 350

Ile Cys Gly Val Gly Gly Thr Leu Thr Ala Ile Asp Asn Leu Gly Gln
        355                 360                 365

Ile Gly Asn Ser Leu Gly Tyr Pro Lys Arg Ser Val Ser Thr Phe Val
    370                 375                 380

Ser Leu Val Ser Ile Trp Asn Tyr Tyr Gly Arg Val Val Ser Gly Val
385                 390                 395                 400

Val Ser Glu Ile Phe Leu Ile Lys Tyr Lys Phe Pro Arg Pro Leu Met
                405                 410                 415
```

-continued

```
Leu Thr Met Val Leu Leu Leu Ser Cys Ala Gly His Leu Leu Ile Ala
            420                 425                 430

Phe Asn Val Pro Gly Gly Leu Tyr Val Ala Ser Val Ile Ile Gly Phe
            435                 440                 445

Cys Phe Gly Ala Gln
        450

<210> SEQ ID NO 6
<211> LENGTH: 191
<212> TYPE: PRT
<213> ORGANISM: Arabidopsis thaliana

<400> SEQUENCE: 6

Met Val Ala Ala Ser Pro Gly Gly Ser Met Lys Ser Leu Thr Ile Gln
1               5                   10                  15

Ile Leu Thr Gly Arg Trp Phe Met Phe Phe Gly Ser Leu Leu Ile Met
            20                  25                  30

Ser Thr Ala Gly Ala Thr Tyr Met Phe Gly Ile Tyr Ser Gly Asp Ile
            35                  40                  45

Lys Glu Thr Leu Gly Tyr Asp Gln Thr Thr Leu Asn Leu Leu Ser Phe
        50                  55                  60

Phe Lys Asp Leu Gly Ala Asn Val Gly Val Leu Ala Gly Leu Leu Asn
65                  70                  75                  80

Glu Val Thr Pro Pro Trp Phe Ile Leu Leu Ile Gly Ala Ile Leu Asn
                85                  90                  95

Phe Phe Gly Tyr Phe Met Ile Trp Leu Ala Val Thr Glu Arg Ile Ser
            100                 105                 110

Lys Pro Gln Val Trp His Met Cys Leu Tyr Ile Cys Val Gly Ala Asn
            115                 120                 125

Ser Gln Ser Phe Ala Asn Thr Gly Ser Leu Val Thr Cys Val Lys Asn
        130                 135                 140

Phe Pro Glu Ser Arg Gly Val Val Leu Gly Ile Leu Lys Gly Tyr Val
145                 150                 155                 160

Gly Leu Ser Gly Ala Ile Ile Thr Gln Leu Tyr Arg Ala Phe Tyr Gly
                165                 170                 175

Glu Asp Thr Lys Glu Leu Ile Leu Met Ile Gly Lys His Asn Phe
            180                 185                 190
```